United States Patent
Cox et al.

(10) Patent No.: US 10,653,752 B2
(45) Date of Patent: May 19, 2020

(54) METHODS AND USE OF GROWTH HORMONE SUPERGENE FAMILY PROTEIN ANALOGS FOR TREATMENT OF RADIATION EXPOSURE

(71) Applicant: Bolder Biotechnology, Inc., Boulder, CO (US)

(72) Inventors: George N. Cox, Louisville, CO (US); Christie M. Orschell, Indianapolis, IN (US)

(73) Assignee: Bolder Bio Technology, Inc., Boulder, CO (US)

( * ) Notice: Subject to any disclaimer, the term of this patent is extended or adjusted under 35 U.S.C. 154(b) by 0 days.

(21) Appl. No.: 15/997,406

(22) Filed: Jun. 4, 2018

(65) Prior Publication Data

US 2018/0339021 A1 Nov. 29, 2018

Related U.S. Application Data

(62) Division of application No. 15/073,246, filed on Mar. 17, 2016, now Pat. No. 10,016,485, which is a division of application No. 13/471,293, filed on May 14, 2012, now Pat. No. 9,320,777.

(60) Provisional application No. 61/486,169, filed on May 13, 2011, provisional application No. 61/527,320, filed on Aug. 25, 2011.

(51) Int. Cl.
*A61K 38/20* (2006.01)
*A61K 47/60* (2017.01)
*A61K 38/27* (2006.01)
*A61K 38/19* (2006.01)

(52) U.S. Cl.
CPC ........ *A61K 38/2073* (2013.01); *A61K 38/193* (2013.01); *A61K 38/27* (2013.01); *A61K 47/60* (2017.08)

(58) Field of Classification Search
None
See application file for complete search history.

(56) References Cited

U.S. PATENT DOCUMENTS

| | | | |
|---|---|---|---|
| 4,810,643 A | 3/1989 | Souza | |
| 5,437,863 A | 8/1995 | Williams et al. | |
| 6,066,317 A | 5/2000 | Yang et al. | |
| 6,555,660 B2 | 4/2003 | Nissen et al. | |
| 6,608,183 B1 | 8/2003 | Cox, III | |
| 6,753,165 B1 | 6/2004 | Cox et al. | |
| 7,148,333 B2 | 12/2006 | Cox, III | |
| 7,214,779 B2 | 5/2007 | Cox, III | |
| 7,232,885 B2 | 6/2007 | Cox, III | |
| 7,253,267 B2 | 8/2007 | Cox, III | |
| 7,306,931 B2 | 12/2007 | Rosendahl et al. | |
| 7,309,781 B2 | 12/2007 | Cox, III | |
| 7,371,370 B2 | 5/2008 | Sarkar et al. | |
| 7,495,087 B2 | 2/2009 | Cox, III | |
| 7,754,855 B1 | 7/2010 | Cox, III et al. | |
| 7,994,124 B2 | 8/2011 | Cox | |
| 8,133,480 B2 | 3/2012 | Cox, III | |
| 8,748,392 B2 | 6/2014 | Cox, III | |
| 8,841,249 B2 | 9/2014 | Johansen et al. | |
| 9,320,777 B2 | 4/2016 | Cox et al. | |
| 1,001,648 A1 | 7/2018 | Cox et al. | |
| 2003/0064480 A1* | 4/2003 | Lauffer | C07K 14/505 435/69.7 |
| 2006/0286069 A1 | 12/2006 | Nissen et al. | |
| 2010/0183543 A1 | 7/2010 | Yonehiro et al. | |
| 2017/0080055 A1 | 3/2017 | Cox et al. | |

FOREIGN PATENT DOCUMENTS

| | | |
|---|---|---|
| WO | WO 01/87925 | 11/2001 |
| WO | WO 2005/027978 | 3/2005 |
| WO | WO 2010/033884 | 3/2010 |

OTHER PUBLICATIONS

Waselenko et al, Annals of Internal Medicine, 2004; vol. 140, pp. 1037-1051.*
Aagaard et al., "RNAi therapeutics: Principles, prospects and challenges," Advanced Drug Delivery Reviews, 2007, vol. 59, Iss. 2-3, pp. 75-86.
Bowie et al., "Deciphering the message in protein sequences: tolerance to amino acid substitutions," Science, 1990, vol. 247, Iss. 4948, pp. 1306-1310.
Brown et al. "Tolerance of single, but not multiple, amino acid replacements in antibody VH CDR 2: a means of minimizing B cell wastage from somatic hypermutation?," Journal of Immunology, 1996, vol. 156, Iss. 9, pp. 3285-3291.
Burgess et al., "Possible dissociation of the heparin-binding and mitogenic activities of heparin-binding (acidic fibroblast) growth factor-1 from its receptor-binding activities by site-directed mutagenesis of a single lysine residue," Journal of Cell Biology, 1990, vol. 111, Iss. 5, pp. 2129-2138.
Lazar et al., "Transforming growth factor alpha: mutation of aspartic acid 47 and leucine 48 results in different biological activities," Molecular and Cellular Biology, 1988, vol. 8, Iss. 3, pp. 1247-1252.

(Continued)

*Primary Examiner* — Bridget E Bunner
*Assistant Examiner* — Fozia Hamud
(74) *Attorney, Agent, or Firm* — Sheridan Ross P.C.

(57) ABSTRACT

Methods and compositions for the use of long-acting hematopoietic factor protein analogs for accelerating hematopoietic recovery in subjects who have been or will be exposed to radiation are disclosed.

20 Claims, 12 Drawing Sheets
Specification includes a Sequence Listing.

(56) References Cited

OTHER PUBLICATIONS

Medhora et al., "Mitigation of Radiation-Induced Injuries to Multiple Organs in Rats by FDA-Approved Drugs and Supportive Care," International Journal of Radiation Oncology, Biology, Physics, 2014, vol. 90, Iss.1 Suppl., Abstract 3527, pp. S809-S810.

Plett et al., "PEGylated G-CSF (BBT-015), GM-CSF (BBT-007), and IL-11 (BBT-059) Analogs Enhance Survival and Hematopoietic Cell Recovery in a Mouse Model of the Hematopoietic Syndrome of the Acute Radiation Syndrome," Health Physics, 2014, vol. 106, Iss. 1, pp. 7-20.

Vajdos et al., "Comprehensive Functional Maps of the Antigen-binding Site of an Anti-ErbB2 Antibody Obtained with Shotgun Scanning Mutagenesis," Journal of Molecular Biology, 2002, vol. 320, Iss. 2, pp. 415-428.

Warzocha et al., "Antisense Strategy: Biological Utility and Prospects in the Treatment of Hematological Malignancies," Leukemia and Lymphoma, 2009, vol. 24. Iss. 3-4, pp. 267-281.

Abdel-Meguide et al., "Three-dimensional structure of a genetically engineered variant of porcine growth hormone," Proc. Natl. Acad. Sci. USA, 1987, vol. 84, pp. 6434-6437.

Arakawa et al., "Cysteine 17 of recombinant human granulocyte colony-stimulating factor is partially solvent-exposed," J. Protein Chem., 1993, vol. 12, pp. 525-531.

Bazan, "Haemopoietic receptors and helical cytokines," Immunology Today, 1990, vol. 11, pp. 350-354.

Bertho et al., "Comparison of autologous cell therapy and granulocyte-colony-stimulating factor (G-CS) injection vs. G-CSF injection alone for the treatment of acute radiation syndrome in a non-human primate model," Int. J. Radiation Oncology Biol. Phys., 2005, vol. 63, pp. 911-920.

Blumberg et al., "Interleukin 20: Discovery, Receptor Identification, and Role in Epidermal Function," Cell, 2001, vol. 104, pp. 9-19.

Boerma et al. "Local administration of interleukin-11 ameliorates intestinal radiation injury in rats," Cancer Res., 2007, vol. 67, pp. 9501-9506.

Booth et al., "Protection against mucosal injury by growth factors and cytokines," J National Cancer Institute Monographs, 2001, vol. 29, pp. 16-20.

Bork, "Powers and Pitfalls in Sequence Analysis: The 70% Hurdle," Genome Research, 2000, vol. 10, Iss. 4, pp. 398-400.

Bowen et al., "Relationship between molecular mass and duration of activity of polyethylene glycol conjugated granulocyte colony-stimulating factor mutein," Exp. Hematol., 1999, vol. 27, pp. 425-432.

Cairo, "Dose reductions and delays: limitations of myelosuppressive chemotherapy," Oncology, 2000, vol. 14, pp. 21-31.

Cairo et al., "Modulation of neonatal rat myeloid kinetics resulting in peripheral neutrophilia by single pulse administration of Rh granulocyte-macrophage colony-stimulating factor and Rh granulocyte colony-stimulating factor," Biol. Neonate, 1991, vol. 59, pp. 13-21.

Cantrell et al., "Cloning, sequence, and expression of a human granulocyte/macrophage colony-stimulating factor," Proc. Natl Acad. Sci. USA, 1985, vol. 85, pp. 6250-6254.

Carlo-Stella et al., "Use of recombinant human growth hormone (rhGH) plus recombinant human granulocyte colony-stimulating factor (rhG-CSF) for the mobilization and collection of CD34+ cells in poor mobilizers," Blood, 2004, vol. 103, pp. 3287-3295.

Charrier et al., "Inhibition of angiotensin I-converting enzyme induces radioprotection by preserving murine hematopoietic short-term reconstituting cells," Blood, 2004, vol. 104, Iss. 4 pp. 978-985.

Chen et al., "Growth hormone mitigates against lethal irradiation and enhances hematologic and immune recovery in mice and non-human primates," PLoS One (www.plosone.org), 2010, vol. 5(6), e11056, 12 pages.

Cox et al., "A long-acting, monoPEGylated human growth hormone analog is a potent stimulator of weight gain and bone growth in hypophysectomized rats," Endocrinology, 2007, vol. 148, pp. 1590-1597.

Cox et al., "Enhanced circulating half-life and hematopoietic properties of a human granulocyte colony-stimulating factor (G-CSF)-immunoglobulin fusion protein," Exp. Hematol., 2004, vol. 32, pp. 441-449.

Dainiak et al., "The Hematologist and Radiation Casualties," Am. Soc. Hematology, 2003, pp. 473-496.

Davis et al. "Timing of captopril administration determines radiation protection or radiation sensitization in a murine model of total body irradiation," Experimental Hematology, 2010, vol. 38, Iss. 4, pp. 270-281.

De Vos et al., "Human Growth Hormone and Extracellular Domain of Its Receptor: Crystal Structure of the Complex," Science, 1992, vol. 255, pp. 306-312.

DiCarlo et al., "Radiation injury after a nuclear detonation: medical consequences and the need for scarce resource allocation," Disaster Med Public Health Prep, 2011, vol. 5(Suppl. 1), pp. S32-S44.

Doerks et al., "Protein annotation: detective work for function prediction," Trends in Genetics, 1998, vol. 14, Iss. 6, pp. 248-250.

Doherty et al., "Site-Specific PEGylation of Engineered Cysteine Analogues of Recombinant Human Granulocyte-Macrophage Colony-Stimulating Factor," Bioconjugate Chemistry, 2005, vol. 16, pp. 1291-1298.

Drouet et al., "Cytokines in combination to treat radiation-induced myelosuppression: evaluation of Scf + glycosylated EPO + PEGylated G-CSF as an emergency treatment in highly irradiated monkeys," Hematologica, 2008, vol. 93, pp. 465-466.

Du et al., "A bone marrow stromal-derived growth factor, Interleukin-11, stimulates recovery of small intestinal mucosal cells after cytoablative therapy," Blood, 1994, vol. 83, pp. 33-37.

Du et al., Interleukin-11: review of molecular, cell biology and clinical use. Blood, 1997, vol. 89, pp. 3897-3908.

Ersoy et al., "Effect of Growth Hormone on small intestinal homeostasis relation to cellular mediators IGF-I and IGFBP-3," World J Gastroenterol, 2009, vol. 15, pp. 5418-5424.

Fares et al., "Design of a long-acting follitropin agonist by fusing the C-terminal sequence of the chorionic gonadotropin β subunit to the follitropin β subunit," Proceedings of the National Academy of Sciences of the United States of America, 1992, vol. 89, Iss. 10, pp. 4304-4308.

Ghosh et al. "Renin-Angiotensin System Suppression Mitigates Experimental Radiation Pneumonitis," International Journal of Radiation Oncology*Biology*Physics, 2009, vol. 75, Iss. 5, pp. 1528-1536.

Glaspy, "Hematopoietic management in oncology practice. Part 1. Myeloid growth factors," Oncology, 2003, vol. 17, pp. 1593-1603.

Goeddel et al., "Direct expression in *Escherichia coli* of a DNA sequence coding for human growth hormone," Nature, 1979, vol. 281(5732), pp. 544-548.

Goldman, "Preclinical biology of Interleukin-11: a multifunctional hematopoietic cytokine with potent thrombopoietic activity," Stem Cells, 1995, vol. 13, pp. 462-471.

Goodson et al., "Site-Directed Pegylation of Recombinant Interleukin-2 at its Glycosylation Site," Biotechnology, 1990, vol. 8, pp. 343-346.

Gordon et al. "A phase I trial of recombinant human interleukin-11 (neumega rhIL-11 growth factor) in women with breast cancer receiving chemotherapy," Blood, 1996, vol. 87, Iss. 9, pp. 3615-3624.

Hao et al., "Effects of Recombinant Human Interleukin 11 on Thrombocytopenia and Neutropenia in Irradiated Rhesus Monkeys," Radiation Res., 2004, vol. 162, pp. 157-163.

Howarth et al., "Effects of insulin-like growth factor-I administration on radiation enteritis in rats," Scand J Gastroenterol, 2003, vol. 32, pp. 1118-1124.

Howarth, "Insulin-like growth factor-I and the gastrointestinal system: therapeutic indications and safety implications," J. Nutr., 2003, vol. 133, pp. 2109-2112.

Ihle et al., "Signaling Through the Hematopoietic Cytokine Receptors," Annu. Rev. Immunol., 1995, vol. 13, pp. 369-398.

Kawashima et al., "Molecular cloning of cDNA encoding adipogenesis inhibitory factor and identity with Interleukin-11," FEBS Letts., 1991, vol. 283, pp. 199-202.

(56) References Cited

OTHER PUBLICATIONS

Kiessling et al., "Functional expression of the Interleukin-11 receptor alpha chain and evidence of antiapoptotic effects in human colonic epithelial cells," J. Biol. Chem., 2004, vol. 279:, pp. 10304-10315.
Kitamura et al., "Establishment and characterization of a unique human cell line that proliferates dependently on GM-CSF, IL-3, or erythropoietin," J.Cell. Physiol., 1989, vol. 140, 323-334.
Kubota et al., "Structural characterization of natural and recombinant human granulocyte colony-stimulating factors," J. Biochem., 1990, vol. 107, pp. 486-492.
Lee et al., "Isolation of cDNA for a human granulocyte-macrophage colony-stimulating factor by functional expression in mammalian cells," Proc. Natl. Acad. Sci. USA, 1985, vol. 82, pp. 4360-4364.
Leonard et al., "Recombinant human interleukin-11 stimulates multilineage hematopoietic recovery in mice after a myelosuppressive regimen of sublethal irradiation and carboplatin," Blood, 1994, vol. 83, pp. 1499-1506.
Lu et al., "Disulfide and secondary structures of recombinant human granulocyte colony-stimulating factor," Arch. Biochem. Biophys., 1989, vol. 268, pp. 81-92.
Macvittie, "Defining the full therapeutic potential of recombinant growth factors in the post radiation-accident environment: the effect of supportive care plus administration of G-CSF," Health Phys., 2005, vol. 89, pp. 546-555.
Martial et al., "Human growth hormone: complementary DNA cloning and expression in bacteria," Science, 1979, vol. 205(4406), pp. 602-607.
Mayer et al., "Efficacy of recombinant human granulocyte-macrophage colony-stimulating factor in rhesus monkeys," Ann N Y Acad Sci, 1987, vol. 511, pp. 17-29.
Mayer et al., "In vitro and in vivo activity of human recombinant granulocyte-macrophage colony-stimulating factor in dogs," Exp. Hematol., 1990, vol. 18, pp. 1026-1033.
Mayer et al., "Recombinant human GM-CSF induces leukocytosis and activates peripheral blood polymorphonuclear neutrophils in nonhuman primates," Blood, 1987, vol. 70, pp. 206-213.
Mayer et al., "Recombinant murine granulocyte-macrophage colony-stimulating factor augments neutrophil recovery and enhances resistance to infections in myelosuppressed mice," J. Infect. Dis., 1991, vol. 163, pp. 584-590.
Molteni et. al., "Control of radiation-induced pneumopathy and lung fibrosis by angiotensin-converting enzyme inhibitors and an angiotensin II type 1 receptor blocker," International Journal of Radiation Biology, 2000, vol. 76, Iss. 4, pp. 523-532.
Mott et al., "Four-helix bundle growth factors and their receptors: protein-protein interactions," Current Opinion in Structural Biology, 1995, vol. 5, pp. 114-121.
Moulder et al., "Captopril and Losartan for Mitigation of Renal Injury Caused by Single-Dose Total-Body Irradiation," Radiation Research, 2011, vol. 175, Iss. 1, pp. 29-36.
Moulder et al., "Re: Davis et al., "Timing of captopril administration determines radiation protection or radiation sensitization in a murine model of total body irradiation"," Experimental Hematology, 2011, vol. 39, Iss. 5, pp. 521-524.
Mylonas et al., "Growth Hormone and insulin-like growth factor I protect intestinal cells from radiation induced apoptosis," Mol Cell Endocrinol., 2000, vol. 160, pp. 115-122.
Nagata et al., "Molecular cloning and expression of cDNA for human granulocyte colony-stimulating factor," Nature, 1986, vol. 319(6052), pp. 415-418.
Nagata et al., "The chromosomal gene structure and two mRNAs for human granulocyte colony-stimulating factor," EMBO J., 1986, vol. 5, pp. 575-581.
Neta et al., "Cytokines in radiation injury," Blood, 1988, vol. 72, pp. 1093-1095.
Neta et al., "Interdependence of the radioprotective effects of human recombinant interleukin-1 alpha, tumor necrosis factor, granulocyte colony-stimulating factor, and murine recombinant granulocyte-macrophage colony-stimulating factor," J. Immunol, 1988, vol. 140, pp. 108-111.
Paul et al., "Molecular cloning of a cDNA encoding interleukin 11, a stromal cell-derived lymphopoietic and hematopoietic cytokine," Proc. Natl. Acad. Sci. USA, 1990, vol. 87, pp. 7512-7516.
Picken et al., "Nucleotide sequence of the gene for heat-stable enterotoxin II of *Escherichia coli*," Infect. Immun., 1983, vol. 42, pp. 269-275.
Potten, "Interleukin-11 protects the clonogenic stem cells in murine small-intestinal crypts from impairment of their reproductive capacity by radiation," Int. J. Cancer, 1995, vol. 62, pp. 356-361.
Potten, "Protection of the small intestinal clonogenic stem cells from radiation-induced damage by pretreatment with interleukin-11 also increases murine survival time," Stem Cells, 1996, vol. 14, pp. 452-459.
Raguso et al., "Protective effects of recombinant growth hormone on intestinal mucosa in rats receiving abdominal radiotherapy," Clin Nutr., 2002, vol. 21, pp. 487-490.
Redlich et al., "IL-11 enhances survival and decreases TNF production after radiation-induced thoracic injury," J Immunology, 1996, vol. 157, pp. 1705-1710.
Rosendahl et al., "Site-specific protein PEGylation: application to cysteine analogs of recombinant human granulocyte colony-stimulating factor," BioProcess International, 2005, vol. 3, pp. 52-62.
Schuening et al., "Effect of recombinant human granulocyte colony-stimulating factor on hematopoiesis of normal dogs and on hematopoietic recovery after otherwise lethal total body irradiation," Blood, 1989, vol. 74, pp. 1308-1313.
Schwertschlag et al., "Hematopoietic, immunomodulatory and epithelial effects of interleukin-11," Leukemia, 1999, vol. 13, pp. 1307-1315.
Sirohi et al., "Use of physiological doses of human growth hormone in haematological patients receiving intensive chemotherapy promotes haematopoietic recovery: a double blind randomized, placebo-controlled study," Bone Marrow Transplant., 2007, vol. 39, pp. 115-120.
Sitaraman et al., "Oprelvekin. Genetics Institute," Curr. Opin. Investig. Drugs, 2001, vol. 2, pp. 1395-1400.
Skolnick et al., "From genes to protein structure and function: novel applications of computational approaches in the genomic era," Trends in Biotechnology, 2000, vol. 18, Iss. 1, pp. 34-39.
Sonis et al., "Defining mechanisms of action of interleuikin-11 on the progression of radiation-induced oral mucositis in hamsters," Oral Oncology, 2000, vol. 36, pp. 373-381.
Souza et al., "Recombinant Human Granulocyte Colony-Stimulating Factor: Effects on Normal and Leukemic Myeloid Cells," Science, 1986, vol. 232, pp. 61-65.
Stribling et al., "Aerosol gene delivery in vivo," Proceedings of the National Academy of Sciences of the United States of America, 1992, vol. 89, Iss. 23, pp. 11277-11281.
Takagi et al., "Enhanced pharmacological activity of recombinant human interleukin-11 (rhIL-11) by chemical modification with polyethylene glycol," J. Controlled Research, 2007, vol. 119, pp. 271-278.
Tokuriki et al., "Stability effects of mutations and protein evolvability," Current Opinion in Structural Biology, 2009, vol. 19, Iss. 5, pp. 596-604.
Uckun et al., "In vivo radioprotective effects of recombinant human granulocyte colony-stimulating factor in lethally irradiated mice," Blood, 1990, vol. 75, pp. 638-645.
Van Der Meeren et al., "Administration of recombinant human interleukin-11 after supralethal radiation exposure promotes survival in mice: interactive effect with thrombopoietin," Radiat. Res., 2002, vol. 157, pp. 642-649.
Waddick et al., "Comparative Analysis of the in vivo Radioprotective Effects of Recombinant Granulocyte Colony-Stimulating Factor (G-CSF), Recombinant Granulocyte-Macrohage CSF, and Their Combination," Blood, 1991, vol. 77, pp. 2364-2371.
Wells, "Additivity of mutational effects in proteins," Biochemistry, 1990, vol. 29, Iss. 37, pp. 8509-8517.

(56) References Cited

OTHER PUBLICATIONS

Wen et al., "Erythropoietin Structure-Function Relationships," J Biol. Chem., 1994, vol. 269, pp. 22839-22846.

Yang, "Interleukin-11 (IL-11) and its receptor: Biology and potential clinical applications in thrombocytopenic states," Chapter 13 of Cytokines: Interleukins and Their Receptors, Kurzrock et al., eds., Academic Publishers, Norwell, MA, 1995, pp. 321-340.

Zhang et al., "Effects of human growth hormone on hematopoietic recovery of rats receiving chemotherapy," Chemotherapy, 2008, vol. 54, pp. 447-455.

Official Action for U.S. Appl. No. 13/471,293 dated Mar. 26, 2013, 17 pages.

Official Action for U.S. Appl. No. 13/471,293 dated Oct. 31, 2013, 13 pages.

Official Action for U.S. Appl. No. 13/471,293 dated May 20, 2014, 13 pages.

Official Action for U.S. Appl. No. 13/471,293 dated Mar. 16, 2015, 16 pages.

Notice of Allowance for U.S. Appl. No. 13/471,293 dated Dec. 21, 2015, 9 pages.

Official Action for U.S. Appl. No. 15/073,246 dated Jul. 17, 2017, 15 pages.

Notice of Allowance for U.S. Appl. No. 15/073,246 dated Mar. 8, 2018, 8 pages.

Farese et al. "The Ability of Filgrastim to Mitigate Mortality Following LD50/60 Total-body Irradiation Is Administration Time-Dependent," Health Physics, 2014, vol. 106, Iss. 1, pp. 39-47.

Farese et al., "Filgrastim Improves Survival in Lethally Irradiated Nonhuman Primate," Radiation Research, 2013, 179, Iss. 1, pp. 89-100.

Farese et al. "Combination Protocols of Cytokine Therapy With Interleukin-3 and Granulocyte-Macrophage Colony-Stimulating Factor in a Primate Model of Radiation-Induced Marrow Aplasia," Blood, Nov. 1993, vol. 82, No. 10, pp. 3012-3018.

Barshishat-Kupper et al., "Captopril modulates hypoxia-inducible factors and erythropoietin responses in a murine model of total body irradiation", Experimental Hematology, 2011, vol. 39, Iss. 3, pp. 293-304.

\* cited by examiner

METHODS AND USE OF GROWTH HORMONE SUPERGENE FAMILY PROTEIN ANALOGS FOR TREATMENT OF RADIATION EXPOSURE

CROSS-REFERENCE TO RELATED APPLICATIONS

This application is a divisional application of U.S. application Ser. No. 15/073,246, filed Mar. 17, 2016, now U.S. Pat. No. 10,016,485, which is a divisional application of U.S. application Ser. No. 13/471,293, filed May 14, 2014, now U.S. Pat. No. 9,320,777 which claims the benefit of priority under 35 U.S.C. § 119(e) from each of U.S. Provisional Application No. 61/486,169, filed May 13, 2011 and U.S. Provisional Application No. 61/527,320, filed Aug. 25, 2011. U.S. application Ser. Nos. 15/073,246 and 13/471,293, U.S. Provisional Application Nos. 61/486,169 and 61/527,320 are each incorporated herein by reference in its entirety.

GOVERNMENT SUPPORT

This invention was made with government support under grant numbers AI084288, AI084301, and AI088928, each awarded by the National Institutes of Health. The government has certain rights in the invention.

REFERENCE TO A SEQUENCE LISTING

This application contains a Sequence Listing submitted electronically as a text file by EFS-Web. The text file, named "4152-20_Sequence_Listing_ST25" has a byte size of 9 KB, and was recorded on May 14, 2012. The information contained in the text file is incorporated herein by reference in its entirety pursuant to 37 CFR § 1.52(e)(5).

FIELD OF THE INVENTION

The present invention generally relates to methods and compositions for use of growth hormone supergene family protein analogs to treat subjects who have been exposed to radiation.

BACKGROUND OF THE INVENTION

Exposure to high radiation doses causes a well characterized set of radiation dose-dependent and time-dependent organ malfunctions (Acute Radiation Syndrome or ARS), which can lead to severe morbidity and death. Different tissues differ in their sensitivities to radiation exposure, primarily due to differences in the number and turnover of stem cells within each tissue. Bone marrow is one of the most radiation-sensitive tissues, and one of the first signs of acute radiation exposure is bone marrow aplasia. Patients exposed to acute, high dose radiation typically develop severe neutropenia, anemia, thrombocytopenia and lymphopenia within 2-3 weeks of exposure, and many patients die from hematopoietic failure. Patients that survive the early hematopoietic complications of acute radiation exposure may develop gastrointestinal and lung problems over the ensuing months and years. Patients may be exposed to high radiation doses in a hospital setting as a means of treating disease, e.g., cancer, as a result of detonation of a nuclear device, or leakage of radioactivity from a facility containing radioactive substances, e.g., a nuclear power plant. Complications of radiation exposure often limit the amount of radiation treatment cancer patients receive, which reduces effectiveness of the radiation treatment and reduces overall patient survival.

Hematopoietic growth factors have been shown to increase the survival of myelosuppressed animals, because they counteract the complications that result from neutropenia and thrombocytopenia, such as hemorrhages and infections. However, most hematopoietic growth factors are unable to protect animals from lethal doses of radiation (Van der Meeren, 2002). Many hematopoietic factors (proteins that stimulate growth, proliferation and differentiation of blood cells and bone marrow cells) are members of the growth hormone (GH) supergene family of proteins (Bazan (1990); Mott and Campbell (1995); Silvennoinen and Ihle (1996); Blumberg et al. (2001)), which include the following proteins: growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, IL-19, IL-20, IL-21, MDA-7, IL-TIF, AK-155, oncostatin M, ciliary neurotrophic factor, leukemia inhibitory factor, alpha interferon, beta interferon, gamma interferon, omega interferon, tau interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). It is anticipated that additional members of this gene family will be identified in the future through gene cloning and sequencing. Members of the GH supergene family have similar secondary and tertiary structures, despite the fact that they generally have limited amino acid or DNA sequence identity. The shared structural features allow new members of the gene family to be readily identified.

Recombinant granulocyte colony-stimulating factor (G-CSF) is a 19 kDa protein that stimulates proliferation and differentiation of bone marrow cells into granulocytes (neutrophils, eosinophils and basophils). Recombinant G-CSF has been used to ameliorate neutropenia following myelosuppressive chemotherapy (Glaspy, 2003) and has also been used to accelerate hematopoietic recovery following bone marrow transplantation and to mobilize blood progenitor cells for transplantation (Glaspy, 2003). Recombinant G-CSF has a short half-life in humans and typically is administered by daily injection for 15-21 days following chemotherapy. The requirement for daily administration limits the attractiveness of G-CSF to chemotherapy patients and for the treatment of patients that have been exposed to radiation, such as ARS patients. Although useful doses and dosing regimens of G-CSF for treating chemotherapy-related neutropenia are known, it is not known however if such treatments with G-CSF also provide therapeutic benefits e.g., improved survival and hematopoietic recovery, to patients that have been exposed to radiation, such as ARS patients.

Recombinant granulocyte-macrophage colony-stimulating factor (GM-CSF) is a 14 kDa cytokine that regulates proliferation, differentiation and functional activities of a variety of hematopoietic cells of the granulocyte and macrophage lineages, including neutrophils, eosinophils, basophils, monocytes, macrophages, and dendritic cells. Recombinant human GM-CSF is used in a variety of hematopoietic disorders, including reducing the severity of chemotherapy-induced neutropenia, accelerating hematopoietic recovery following bone marrow transplantation and mobilizing blood progenitor cells for transplantation. Recombinant GM-CSF has a short half-life in humans and typically is administered by daily injection for 15-21 days following chemotherapy. The requirement for daily administration also limits the attractiveness of GM-CSF to chemotherapy patients and for the treatment of patients that have been exposed to radiation, such as ARS patients.

Recombinant interleukin-11 (IL-11) is a 19 kDa cytokine that stimulates the proliferation and differentiation of megakaryocytes into platelets (Yang, 1995; Goldman 1995). Recombinant IL-11 is used to ameliorate thrombocytopenia following myelosuppressive chemotherapy in cancer patients (Sitaraman and Gewirtz, 2001). IL-11 administration results in higher platelet nadirs and accelerates platelet recovery in cancer patients receiving chemotherapy. IL-11 has a short half-life in humans and requires daily administration for maximum effectiveness. IL-11 typically is administered to cancer patients by daily injection for 14-21 days following chemotherapy to ameliorate thrombocytopenia. The requirement for daily administration limits the attractiveness of IL-11 to chemotherapy patients and for the treatment of patients that have been exposed to radiation, such as ARS patients.

Growth Hormone (GH) is a 22 kDa protein that may prove useful for treating ARS. Bone marrow stem cells and intestinal cells express receptors for GH and preclinical and clinical studies have shown that GH treatment stimulates expansion and recovery of hematopoietic cells following chemotherapy (Zhang et al., 2008; Sirohi et al., 2007; Carlo-Stella et al., 2004), synergizes with G-CSF to mobilize CD34+ hematopoietic cells in patients who respond poorly to G-CSF alone, and protects intestinal cells from cell death following radiation exposure (Raguso et al., 2002; Howarth, 2003; Howarth et al., 1997; Mylonas et al., 2000; Ersoy et al., 2009).

Whether treatment with a hematopoietic factor protein, such as a long-acting recombinant G-CSF, GM-CSF, GH, or IL-11 can provide a therapeutic benefit such as accelerated hematopoietic recovery or survival benefit to subjects that have been exposed to radiation, such as ARS patients, is not known.

SUMMARY OF THE INVENTION

One embodiment of the invention relates to a method to accelerate hematopoietic recovery comprising administering to a subject who has been exposed to radiation, an effective dose of a long-acting hematopoietic factor protein analog. In one aspect, the long-acting hematopoietic factor protein can be selected from a long-acting G-CSF analog, a long-acting GM-CSF analog, a long-acting growth hormone (GH) analog, a long-acting IL-11 analog and combinations thereof.

Hematopoietic recovery can result in accelerated recovery of the subject's blood cell type levels selected from platelet levels, red blood cell levels, neutrophil levels, lymphocyte levels, white blood cell levels and combinations thereof. In one aspect, hematopoietic recovery results in accelerated recovery of the subject's platelet levels. In another aspect, hematopoietic recovery results in accelerated recovery of the subject's red blood cell levels. In still yet another aspect, hematopoietic recovery results in accelerated recovery of the subject's platelet levels and red blood cell levels. In still another aspect, hematopoietic recovery results in accelerated recovery of the subject's platelet levels, red blood cell levels and neutrophil levels.

In another aspect of the invention, the subject has been diagnosed as having Acute Radiation Syndrome (ARS).

In yet another aspect of the invention, the long acting hematopoietic factor protein analog is modified with polyethylene glycol (PEG).

In still another aspect, the long acting hematopoietic factor protein analog is fused to a second protein to create a fusion protein. The second protein can be selected from immunoglobulin domains, albumin, transferrin, transferrin receptors, elastin and elastin-like proteins.

In still further aspects, the hematopoietic factor protein analog is a recombinant human G-CSF protein analog comprising one or more cysteine substitutions or additions. In another aspect, the recombinant G-CSF protein analog comprises a cysteine residue substituted for A141 of human G-CSF (SEQ ID NO:1) and a non-cysteine amino acid residue substituted for C17 of human G-CSF (SEQ ID NO:1). In still another aspect, the G-CSF protein analog comprising A141 and C17 amino acid substitutions is further modified with PEG.

In still another aspect of the invention, the long acting hematopoietic factor protein analog is a recombinant human GM-CSF protein analog comprising one or more cysteine substitutions or additions. In another aspect, the recombinant GM-CSF protein analog comprises a cysteine residue substituted for A3 of human GM-CSF (SEQ ID NO:2). In still another aspect, the human GM-CSF protein analog comprising an A3C substitution is further modified with PEG.

In another aspect, the subject can be administered an effective dose of the long acting hematopoietic factor protein analog in a single dose that provides accelerated hematopoietic recovery. In one aspect, the single dose can be at least about 0.1 µg to 5 mg per kg of the subject to which the long-acting hematopoietic factor analog is administered. Preferably, the single dose can be at least about 5 µg/kg to about 1 mg/kg, and more preferably 50 µg/kg to about 300 µg/kg.

In still another aspect, the subject is administered one or more single doses of the long-acting hematopoietic factor protein analog. In another aspect, the subject is administered a single dose of the long-acting hematopoietic factor protein analog one to nine times following the subject's exposure to radiation. In yet another aspect, the subject is administered a single dose of the long-acting hemaptopoietic factor protein analog one to three times following the subject's exposure to radiation. In still another aspect, the subject is administered one single dose of the long-acting hematopoietic factor protein analog.

In another aspect, one or more single doses of the long acting hematopoietic factor protein analog is administered to the subject within 24 hours following the subject's exposure to the radiation. In still another aspect, the subject is administered one or more single doses of the long acting hematopoietic factor protein analog using an every other day dosing regimen. In yet another aspect, the subject is administered one or more single doses of the long acting hematopoietic factor protein analog beginning at least 24 hours following the subject's exposure to the radiation followed by an every other day regimen.

Another embodiment of the invention relates to a method for improving survival of a subject who has been exposed to radiation, by administering to the subject an effective dose of a long-acting hematopoietic factor protein analog. In one aspect, the long-acting hematopoietic factor protein analog can be selected from a G-CSF analog, a GM-CSF analog, a GH analog and an IL-11 analog and combinations thereof.

A further embodiment of the invention relates to a pharmaceutical composition comprising one or more long-acting hematopoietic factor protein analog selected from the group consisting of a long-acting G-CSF analog, a long-acting GM-CSF analog, a long-acting GH analog, a long-acting IL-11 analog and combinations thereof and a pharmaceutical acceptable carrier.

DETAILED DESCRIPTION OF THE INVENTION

Figure 1:
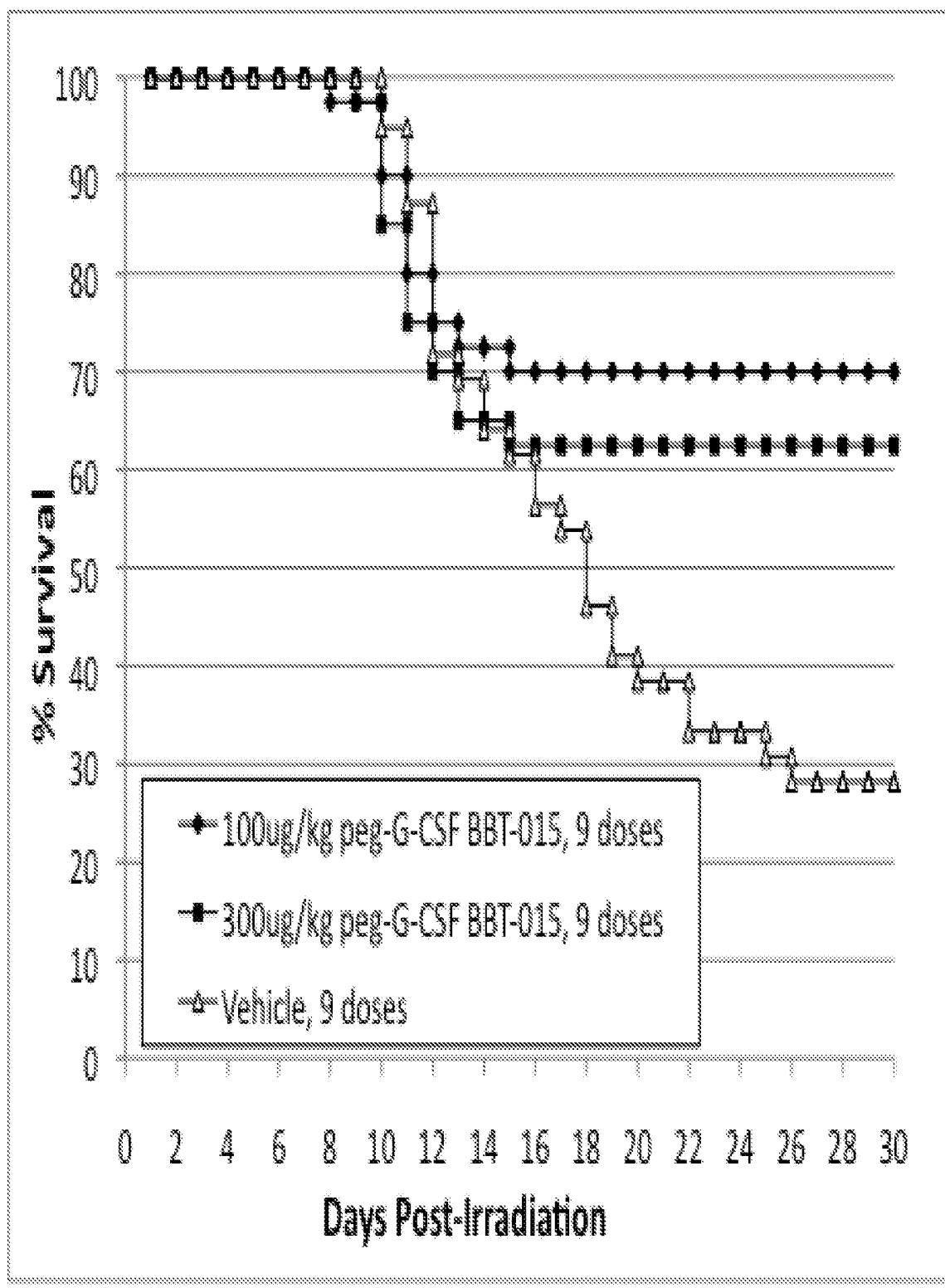
FIG. 1. Kaplan-Meier Survival Curves; pooled data from both radiation dose groups (776+796cGy). Mice were exposed to 776cGy or 796cGy and injected subcutaneously with either 100 µg/kg/day or 300 µg/kg/day peg-G-CSF analog BBT-015 for 9 doses (every other day from day 1 (d1) to day 17 (d17); filled symbols). Control mice were similarly injected but with vehicle (open symbols). Thirty-day survival (p<0.001) and overall survival time (p≤0.022) were significantly increased in mice treated with either dose of peg-G-CSF analog BBT-015. Mice were not treated with antibiotics. N=40 mice per group.

The present invention is directed toward methods to accelerate hematopoietic recovery and improve survival in a subject that has been or will be exposed to radiation. The invention includes administering an effective dose of a long-acting hematopoietic factor protein analog or combinations thereof to the subject either following the subject's exposure to radiation or prior to the subject's exposure to radiation.

Accelerated hematopoietic recovery generally refers to accelerated recovery of a subject's blood cell count or level of various blood cell types including but not limited to white blood cell levels, neutrophil levels, lymphocyte levels, monocyte levels, macrophage levels, eosinophil levels, basophil levels, dendritic cell levels, T lymphocyte levels, B lymphocyte levels, red blood cell levels, platelet levels and combinations thereof, after the subject has been exposed to radiation compared to levels of the same blood cell type from subjects who have not been exposed to radiation (non-exposed or control subjects). Accelerated hematopoietic recovery can also refers to accelerated recovery of a subject's hemoglobin and hematocrit levels compared to these levels from a control. Hemoglobin is a major protein component of red blood cells and changes in hemoglobin levels typically correlate with changes in red blood cell levels. Hematocrit or packed cell volume is a measure of the blood volume that is comprised of red blood cells, thus changes in hematocrit levels typically correlate with changes in a subject's red blood cell levels.

Hematopoietic recovery can be complete, i.e., to levels comparable to levels from non-exposed (control) subjects, or incomplete, i.e., to levels greater than the blood cell nadir but below levels seen in non-exposed (control) subjects. Accelerated hematopoietic recovery generally refers to hematopoietic recovery that occurs sooner compared to subjects that have been exposed to radiation but have not been administered an effective dose of a long acting hemapoietic factor protein analog of the present invention. In one embodiment of the invention, the subject's platelet level recovers to levels comparable to levels from a non-exposed subject (control). In another embodiment, a subject's red blood cell level recovers comparable to levels from a non-exposed subject. In still another embodiment, the subject's platelet level and red blood cell level recovery to levels comparable to levels from a non-exposed subject. In another embodiment of the invention the subject's white blood cell level recovers to levels comparable to levels from a non-exposed subject (control). In another embodiment of the invention the subject's neutrophil level recovers to levels comparable to levels from a non-exposed subject (control). In another embodiment of the invention the subject's lymphocyte level recovers to levels comparable to levels from a non-exposed subject (control). In still another embodiment, the subject's neutrophil level, platelet level and red blood cell level recover to levels comparable to levels from a non-exposed subject. In still another embodiment, the subject's neutrophil level, lymphocyte level, platelet level and red blood cell level recover to levels comparable to levels from a non-exposed subject. In still another embodiment, the subject's neutrophil level, white blood cell level, lymphocyte level, platelet level and red blood cell level recover to levels comparable to levels from a non-exposed subject.

Methods of the invention may be used to accelerate hematopoietic recovery in a variety of subjects that have been exposed to radiation. In one embodiment, the subject has been diagnosed as having ARS. In another embodiment, the subject has been diagnosed as having complications of therapeutic radiation treatment. In another embodiment, the subject includes all animals and preferably, any member of the Vertebrate class, Mammalia, including, without limitation, primates, rodents, livestock and domestic pets. Livestock include mammals to be consumed or that produce useful products (e.g., sheep for wool production). Preferred mammals include humans, dogs, cats, mice, rats, sheep, cattle, horses and pigs, with humans being particularly preferred.

In one embodiment of the invention, the subject has been exposed to high and/or lethal radiation doses that typically results in the subject developing a set of well characterized radiation dose-dependent and time-dependent organ malfunctions including but not limited to bone marrow aplasia, severe neutropenia, anemia, thrombocytopenia, and lymphopenia, within 2-3 weeks of radiation exposure. Subjects can be exposed to high and/or lethal radiation doses for example in a hospital setting, such as for treating diseases with therapeutic radiation (e.g., cancer), as a result of detonation of a nuclear device, or leakage of radioactive substances, e.g., from a nuclear power plant. Therapeutic radiation treatment is radiation treatment given to a patient to affect a therapeutic outcome such as killing cancer cells or slowing the growth of cancer cells.

The hematopoietic factor protein analogs of the present invention are members of the growth hormone supergene family of proteins and include but are not limited to G-CSF analogs, GM-CSF analogs, GH analogs, IL-11 analogs and EPO analogs. Long-acting hematopoietic factor protein analogs include but are not limited to cysteine muteins, polymer modified analogs and fusion protein analogs of the growth hormone supergene family of proteins. Long-acting G-CSF, long-acting GM-CSF, long-acting interleukin-11, long acting GH, long acting EPO protein analogs as well as other Growth Hormone supergene family protein analogs have been created by using various fusion protein and polymer modification technologies, including site-specific PEGylation technology. G-CSF, GM-CSF, IL-11 and GH cysteine analogs are described in U.S. Pat. Nos. 6,608,183, 6,753,165, 7,306,931, 7,309,781, 7,232,885, 7,306,931, 7,214,779, 7,148,333, 7,495,087, 7,253,267, and 8,133,480, all of which are incorporated herein by reference. Site-specific PEGylation permits the rational design of homogeneous PEG-protein conjugates with defined structures and preserved biological activities (Goodson and Katre, 1990). Site-specific PEGylation is accomplished by covalent attachment of cysteine-specific PEGs (maleimide- or vinyl-sulfone-PEGs) to engineered cysteine residues in proteins. At near neutral pH, these PEG reagents selectively attach to the thiol groups of "free" cysteine residues, i.e., cysteine residues not involved in disulfide bonds. The resulting conjugates are hydrolytically stable. Site-specific PEGylation overcomes the problems of product heterogeneity and loss of bioactivity that often occurs when proteins are modified using amine-reactive PEGylation technology and reagents. For example, in vitro biological activities of the site-specific PEGylated G-CSF cysteine analog, G-CSF (A141C; alanine at position 141 changed to cysteine; long-acting), are comparable to that of G-CSF, and 50-fold better than that of G-CSF proteins modified by conventional amine PEGylation technologies (Bowen et al., 1999; U.S. Pat. No. 7,306,931). The PEG-G-CSF (A141C) protein has an 8- to 10-fold longer half-life than G-CSF in rodents. PEG-G-CSF (A141C) also stimulated greater and longer lasting increases in neutrophils and white blood cells than unmodified G-CSF in normal rats. PEG-G-CSF (A141C) accelerated recovery from neutropenia following a single injection in chemotherapy (cyclophosphamide)-treated rats whereas unmodified G-CSF was ineffective as a single injection.

G-CSF is a pluripotent cytokine that stimulates the proliferation, differentiation and function of granulocytes. The protein is produced by activated monocytes and macrophages. The amino acid sequence of G-CSF (SEQ ID NO: 1) is given in Souza et al. (1986), Nagata et al. (1986a, b) and U.S. Pat. No. 4,810,643 all incorporated herein by reference. The human protein is synthesized as a preprotein of 204 or 207 amino acids that is cleaved to yield mature proteins of 174 or 177 amino acids. The larger form has lower specific activity than the smaller form. The protein contains 5 cysteine residues, 4 of which form two disulfide bonds. The fifth cysteine residue, cysteine-17, is unpaired or "free". C17 causes G-CSF to be unstable and aggregate at physiological pH and at 37° C. (Lu et al., 1989; Arakawa et al., 1993). Preferred embodiments of the present invention are G-CSF analogs and PEG-G-CSF analogs that do not contain C17, i.e., the preferred G-CSF analogs contain a non-cysteine amino acid, preferable alanine or serine, substituted for C17. G-CSF analogs containing a non-cysteine amino acid at position 17 are more stable than G-CSF at physiological pH and at 37° C. However, the present invention encompasses G-CSF analogs and PEG-G-CSF analogs that do contain C17 and G-CSF analogs and PEG-G-CSF analogs that contain a non-cysteine amino acid, preferably alanine or serine, substituted for C17. In one embodiment, the long-acting G-CSF protein analog contains A141C and C17S amino acid substitutions and is further modified with a 40 kDa-PEG (this analog is referred to as "BBT-0015"). Additional sites for the introduction of cysteine residues in human G-CSF are: T1, P2, L3, G4, P5, A6, S7, S8, L9, P10, Q11, S12, T38, K40, S53, G55, W58, A59, P60, S62, S63, P65, S66, Q67, A68, Q70, A72, Q90, A91, E93, G94, S96, E98, G100, G125, M126, A127, A129, Q131, T133, Q134, G135, A136, A139, A141, 5142, A143, Q145, Q173 and P174. Most preferred cysteine substitution positions are: T1, P2, L3, A6, S7, W58, A68, E93, A129, Q131, T133, Q134, A136, A139, A141 and Q173. Cysteine residues also can be added preceding the first amino acid of the mature protein, i.e., preceding T1, or following the last amino acid in the mature protein, i.e., following P174.

GM-CSF stimulates the proliferation and differentiation of various hematopoietic cells, including neutrophil, monocyte, eosinophil, erythroid, and megakaryocyte cell lineages. The amino acid sequence of human GM-CSF (SEQ ID NO: 2) is given in Cantrell et al. (1985) and Lee et al (1985) both incorporated herein by reference. GM-CSF is produced as a 144 amino acid preprotein that is cleaved to yield a mature 127 amino acid protein. The mature protein has two sites for N-linked glycosylation. One site is located at the C-terminal end of Helix A; the second site is in the A-B loop.

In another embodiment of the method of the present invention, a recombinant long-acting human GM-CSF protein analog comprises an A3C amino acid substitution. In another aspect the human long acting GM-CSF comprises an A3C amino acid substitution and is further modified with a 40 kDa-PEG (this analog is referred to as "BBT-007"). In still another aspect, the long acting GM-CSF protein analog is a human GM-CSF protein analog comprising one or more cysteine substitutions or additions. Additional sites for the introduction of cysteine residues in human GM-CSF are: A1, P2, A3, R4, S5, P6, S7, P8, S9, T10, Q11, N27, L28, S29, R30, D31, T32, A33, A34, E35, N37, E38, T39, E41, S44, E45, D48, Q50, E51, T53, Q64, G65, R67, G68, S69, L70, T71, K72, K74, G75, T91, E93, T94, S95, A97, T98, T102, I117, D120, E123, V125, Q126 and E127. Most preferred cysteine substitution positions are: A1, A3, S5, S7, N27, T32, A33, E51, R67, S69, E93, T94, T98, Q99, T102, E123, V125, Q126, and E127. Cysteine residues also can be added preceding the first amino acid of the mature protein, i.e., preceding A1, or following the final amino acid of the mature protein, i.e., following E127.

Human and rodent GM-CSF proteins perform similar functions in their respective species. Human and rodent GM-CSF proteins share 50-60% amino acid identity, but there is no cross species cross-reactivity in terms of biological activity or receptor binding. It is possible to use the significant amino acid identity between human and rodent GM-CSF proteins to construct murine GM-CSF hematopoietic factor protein analogs that are analogues of human GM-CSF hematopoietic factor protein analogs. The murine GM-CSF analogs can be expressed, purified and PEGylated using procedures similar to those described for human GM-CSF and in PCT Application No. PCT/US01/16088 (WO 01/87925).

In still another embodiment, the GM-CSF protein analog is a murine GM-CSF protein analog (SEQ ID NO:6) comprising one or more cysteine substitutions or additions. In another embodiment, the murine GM-CSF protein analog comprises a T3C amino acid substitution. In still another aspect, the murine GM-CSF protein analog comprising a T3C substitution is further modified with a 40 kDa-PEG (this analog is referred to as "murine BBT-007"). Methods for making the murine GM-CSF protein analogs are described in U.S. Pat. No. 7,994,124.

IL-11 is a pleiotropic cytokine that stimulates hematopoiesis, lymphopoeisis and acute phase responses. IL-11 shares many biological effects with IL-6. The amino acid sequence of human IL-11 (SEQ ID NO: 3) is given in Kawashima et al. (1991) and Paul et al. (1990) both incorporated herein by reference. IL-11 is synthesized as a precursor protein of 199 amino acids that is cleaved to yield a mature protein of 178 amino acids. Cleavage results in removal of the amino-terminal 21 amino acid signal sequence required for secretion. There are no N-linked glycosylation sites in the protein.

In still another embodiment of the method of the present invention, the recombinant long-acting human IL-11 protein analog comprises a cysteine residue added following the carboxy-terminal amino acid of the mature IL-11 protein. In another embodiment, the long acting human IL-11 protein analog comprises a cysteine residue added following the carboxy-terminal amino acid of the mature human IL-11 protein and is further modified with a 40 kDa-PEG (referred to BBT-059 or IL-11 (*200C)). The long-acting IL-11 analogs of the present invention may or may not contain the amino-terminal proline-22 amino acid of native mature human IL-11 (IL-11 in which the 21 amino acid signal sequence has been removed). The long-acting IL-11 analogs of the present invention may have glycine-23 as the amino-terminal amino acid. In still another embodiment, the long acting human IL-11 protein analog comprises one or more cysteine substitutions or additions. Additional sites for the introduction of cysteine residues in human IL-11 are: P22, G23, P24, P25, P26, G27, P28, P29, R30, V31, S32, P33, D34, P35, R36, A37, D38, L39, R54, Q55, L56, A57, A58, Q59, L60, R61, D62, K63, F64, P65, A66, D67, G68, D69, H70, N71, L72, D73, S74, L75, P76, T77, L78, A79, M80, S81, A82, G83, A84, L85, G86, A87, L88, Q89, L90, P91, G92, V93, L94, W110, L111, R112, E125, L126, G127, 5145, R146, L147, A148, L149, P150, Q151, P152, P153, P154, D155, P156, P157, A158, P159, P160, L161, A162, P163, P164, S165, S166, A167, W168, G169, G170, I171, R172, A173, A174, H175, L194, L195, K196, T197, R198, and L199. Most preferred cysteine substitution positions are: P22, G23, P24, P25, G27, E38, L39, D69, L72, S74, T77, A114, S117, E123, A148, Q151, A158, A162, and S165. Cysteine residues also can be added preceding the first amino acid of the mature protein, i.e., preceding P22, or following the final amino acid of the mature protein, i.e., following L199.

The sequence of human GH is well known (see, e.g., Martial et al. 1979; Goeddel et al. 1979 which are incorporated herein by reference; SEQ ID NO:4). GH is closely related in sequence to prolactin and placental lactogen and these three proteins were considered originally to comprise a small gene family. The primary sequence of GH is highly conserved among animal species (Abdel-Meguid et al., 1987), consistent with the protein's broad species cross-reactivity. The three dimensional folding pattern of porcine GH has been solved by X-ray crystallography (Abdel-Meguid et al., 1987). The protein has a compact globular structure, comprising four amphipathic alpha helical bundles joined by loops. Human GH has a similar structure (de Vos et al., 1992). The four alpha helical regions are termed A-D beginning from the N-terminus of the protein. The loop regions are referred to by the helical regions they join, e.g., the A-B loop joins helical bundles A and B. The A-B and C-D loops are long, whereas the B-C loop is short. GH contains four cysteine residues, all of which participate in disulfide bonds. The disulfide assignments are cysteine53 joined to cysteine165 and cysteine182 joined to cysteine189. In another embodiment of the method of the present invention, a recombinant long-acting human GH protein analog comprises a P133C amino acid substitution. In yet another embodiment, the long acting human GH protein analog comprises a P133C amino acid substitution and is further modified with a 40 kDa-PEG. In another embodiment of the method of the present invention, a recombinant long-acting human GH protein analog comprises a T3C amino acid substitution. In still another embodiment, the long-acting human GH protein analog comprises a T3C amino acid substitution and is further modified with a 40 kDa-PEG. In still another embodiment, the long acting human GH protein analog comprises one or more cysteine substitutions or additions Additional sites for the introduction of cysteine residues in human GH are: F1, T3, P5, E33, A34, Y35, K38, E39, Q40, S43, Q46, N47, P48, Q49, T50, S51, S55, T60, A98, N99, S100, G104, A105, S106, E129, D130, G131, S132, P133, T135, G136, Q137, K140, Q141, T142, S144, K145, D147, T148, N149, S150, H151, N152, D153, S184, E186, G187, S188, and G190. Most preferred cysteine substitution positions are: P2C, T3C, P5C, K38C, Q40C, S55C, S57, N99C, L101C, V102C, Y103C, S132C, P133C, R134C, Q137C, K140C, Q141, Y143, S144C, D147C, T148C, N149, E186C and G187C. Cysteine residues also can be added preceding the N-terminal amino acid of the mature protein, i.e., preceding the F1 amino acid, or following the last amino acid in the mature protein, i.e., following F191.

EPO is the hormone primarily responsible for stimulating erythropoiesis or red blood cell formation. EPO acts on immature red blood cell precursors to stimulate their further proliferation and differentiation into mature red blood cells. A commercial pharmaceutical version is available from Amgen, Inc. Human EPO is a 35-39 kDa glycoprotein secreted by the adult kidney. The mature human protein contains 166 amino acids and is heavily glycosylated. The sequence of human EPO (SEQ ID NO: 5) is shown in Lin et al 1985 and Jacobs et al. 1985, which are incorporated herein by reference. The primary sequence of EPO is highly conserved among species (greater than 80% identity; Wen et al., 1994). Sugar groups account for greater than 40% of the protein's mass. Human EPO contains three N-linked glycosylation sites and one O-linked glycosylation site. Certain amino acids in EPO are non-essential for biological activity and can be mutated to cysteine residues without altering the normal disulfide binding pattern and overall conformation of the molecule. These amino acids are located in the A-B loop (amino acids 23-58 of the mature protein sequence), the B-C loop (amino acids 77-89 of the mature protein sequence), the C-D loop (amino acids 108-131 of the mature protein sequence), proximal to helix A (amino acids 1-8) and distal to helix D (amino acids 153-166 of the mature protein sequence).

In one embodiment of the method of the present invention a dose of long acting EPO protein analog is administered to the subject. Sites for cysteine substitutions are the O-linked glycosylation site (serine-126) and the amino acids comprising the three N-linked glycosylation sites (N24, I25, T26, N38, I39, T40, N83, S84, S85). Other preferred sites for cysteine substitutions in these regions are: A1, P2, P3, R4, D8, S9, T27, G28, A30, E31, H32, S34, N36, D43, T44, K45, N47, A50, K52, E55, G57, Q58, G77, Q78, A79, Q86, W88, E89, T107, R110, A111, G113, A114, Q115, K116, E117, A118, S120, P121, P122, D123, A124, A125, A127, A128, T132, K154, T157, G158, E159, A160, T163, G164, D165 and R166. Cysteine residues also can be introduced proximal to the first amino acid of the mature protein, i.e., proximal to A1, or distal to the final amino acid in the mature protein, i.e., distal to D165 or R166. Other variants in which cys-29 or cys-33 have been replaced with other amino acids, preferably serine or alanine, also are provided.

In one embodiment, long-acting hematopoietic factor protein analogs are fused to a second protein selected from albumin, transferrin, transferrin receptors, or elastin and elastin-like proteins. Fusion protein analogs can be long-acting fusion proteins comprising long-acting G-CSF, long-acting GM-CSF, long-acting IL-11 and long-acting GH fused to immunoglobulin domains (described in U.S. Pat. No. 7,754,855). In another embodiment, long-acting hematopoietic factor protein analogs are fused to any second protein that confers a longer half-life to the hematopoietic factor fusion protein compared to the non-fused hematopoietic factor. The hematopoietic factor protein can be fused to the amino-terminus of the second protein, to the carboxy-terminus of the second protein, or in between two amino acids of the second protein. The hematopoietic factor may be fused to the second protein via an intervening peptide linker or it may be fused to the second protein directly, i.e., without an intervening peptide linker. Examples of joining two proteins as direct fusion proteins and as fusion proteins with peptide linkers are provided in U.S. Pat. No. 7,754,855.

In still other embodiments of the present invention, a polymer can be used for modifying the hematopoietic factor protein. The polymer can be any polymer that confers a half-life that is longer than the half-life of the non-polymer-modified hematopoietic factor protein in animals.

In still other embodiments of the present invention, the polymer used for modifying the protein can be PEG. The PEG can be any PEG that confers a half-life that is longer than the half-life of the unPEGylated protein in animals.

In still other embodiments of the present invention, the polymer used for modifying the protein can be any polymer that confers a half-life that is longer than the half-life of the non-polymer-modified protein in animals.

In still other embodiments of the present invention, the fusion protein used for modifying the protein can be any fusion protein that confers a half-life that is longer than the half-life of the non-fusion protein-modified protein in animals.

Peptides that bind and activate cellular receptors for G-CSF, GM-CSF, GH, IL-11, other members of the growth hormone supergene family and other hematopoietic factors have been described in the literature. The methods described herein also may be applied to using these peptides and long-acting analogs of these peptides for accelerating hematopoietic recovery and improving survival in subjects who have been exposed to radiation.

In embodiments of the present invention, the long-acting hematopoietic factor protein analog is administered to the subject in a dose that provides therapeutic benefits to the subject. Therapeutic benefits include but are not limited to accelerated hematopoietic recovery and/or survival benefits (improved survival) to subjects. Survival benefits include an increase in life expectancy of a subject that has been exposed to radiation.

According to the present invention, an effective administration protocol (i.e., administering the hematopoietic factor protein analog in an effective manner) comprises suitable dose parameters and modes of administration that result in the desired effect in the subject (e.g., acceleration of hematopoietic recovery).

In accordance with the present invention, a suitable single dose size is a dose that results in the desired therapeutic effect in the subject, when administered one or more times over a suitable time period. Doses can vary and one of skill in the art can readily determine appropriate single dose sizes for a given subject based on the size of a patient and the route of administration.

In one aspect of the invention, a suitable single dose of the long acting hematopoietic factor protein analog of the present invention is an amount that, when administered by any route of administration, provides a therapeutic effect in the subject as described above, as compared to a patient which has not been administered the long acting hematopoietic factor protein analog of the present invention (i.e., a control), as compared to the subject prior to administration of the long-acting hematopoietic factor protein analog.

In one aspect of the invention an appropriate single dose of the long-acting hematopoietic factor protein analog is at least about 0.1 µg per kg of the subject to which the long acting hematopoietic factor protein analog is administered, and in other aspects, at least about 0.5 µg/kg, at least about 1.0 µg/kg, at least about 1.5 µg/kg, at least about 2.0 µg/kg, at least about 2.5 µg/kg, at least about 3.0 µg/kg, at least about 3.5 µg/kg, at least about 4.0 µg/kg, at least about 4.5 µg/kg, at least about 5.0 µg/kg, at least about 5.5 µg/kg, at least about 6.0 µg/kg, at least about 6.5 µg/kg, at least about at least about 7.0 µg/kg, at least about 8.0 µg/kg, at least about 9.0 µg/kg, at least about 10 µg/kg, at least about 15 µg/kg, at least about 20 µg/kg, at least about 25 µg/kg, at least about 30 µg/kg, at least about 35 µg/kg, at least about 40 µg/kg, at least about 45 µg/kg, at least about 50 µg/kg, at least about 55 µg/kg, at least about 60 µg/kg, at least about 65 µg/kg, at least about 70 µg/kg, at least about 75 µg/kg, at least about 80 µg/kg, at least about 85 µg/kg, at least about 90 µg/kg, at least about 95 µg/kg, at least about 100 µg/kg, at least about 110 µg/kg, at least about 120 µg/kg, at least about 130 µg/kg, at least about 140 µg/kg, at least about 150 µg/kg, at least about 160 µg/kg, at least about 170 µg/kg, at least about 180 µg/kg, at least about 190 µg/kg, at least about 200 µg/kg, at least about 210 µg/kg, at least about 220 µg/kg, at least about 230 µg/kg, at least about 240 µg/kg, at least about 250 µg/kg, at least about 260 µg/kg, at least about 270 µg/kg, at least about 280 µg/kg, at least about 290 µg/kg, at least about 300 µg/kg, at least about 310 µg/kg, at least about 320 µg/kg, at least about 330 µg/kg, at least about 340 µg/kg, at least about 350 µg/kg, at least about 360 µg/kg, at least about 370 µg/kg, at least about 380 µg/kg, at least about 390 µg/kg, at least about 400 µg/kg, at least about 420 µg/kg, at least about 440 µg/kg, at least about 460 µg/kg, at least about 480 µg/kg, at least about 500 µg/kg, at least about 600 µg/kg, at least about 700 µg/kg, at least about 800 µg/kg, at least about 900 µg/kg, at least about 1.0 mg/kg, at least about 1.5 mg/kg, at least about 2.0 mg/kg, at least about 2.5 mg/kg, at least about 3.0 mg/kg, at least about 3.5 mg/kg, at least about 4.0 mg/kg, at least about 4.5 mg/kg, at least about 5.0 mg/kg, at least about 5.5 mg/kg, at least about 6.0 mg/kg, at least about 6.5 mg/kg, at least about 10 mg/kg, or any dose within this range.

In still another aspect, the effective dose of the long-acting hematopoietic factor protein analog may be administered to the subject one time following the subject's exposure to radiation. In another embodiment, the effective dose may be administered to the subject more than one time following exposure to radiation. For example, the dose may be administered to the subject two times, three times, four times, five times, six times, seven times, eight times, nine times, ten times, or up to thirty times following radiation exposure. In still another aspect, the long-acting hematopoietic factor protein analog can be administered to the subject from one to nine times following radiation exposure, more preferably from one to three times following radiation exposure and most preferably one time following radiation exposure.

In another embodiment of the invention, the step of administering the long acting hematopoietic factor protein analog is conducted after exposure to radiation. In some embodiments, the step of administering is conducted shortly after the exposure. For example, the step of administering can be conducted immediately after radiation exposure or within about 2 hours, within about 4 hours, within about 10 hours, within about 20 hours, within about 24 hours, or within about 30 hours after exposure. In another embodiment, the step of administering is conducted after about 24 hours after radiation exposure. In still another aspect of the invention the long-acting hematopoietic factor can be administered to a subject immediately after radiation exposure or up to 30 days following radiation exposure. More preferably the long-acting hematopoietic factor is administered to a subject immediately after radiation exposure or up to 7 days following radiation exposure. In one preferred aspect, the long acting hematopoietic factor protein analog is administered to the subject within four hours following the subject's exposure to the radiation. In another embodiment, the step of administering is initiated at about 24 hours after exposure. In a preferred embodiment, the step of administering is initiated at about 24 hours after exposure, followed by additional administration of a long acting hematopoietic factor protein analog using an every other day dosing regimen. For example an every other day dosing regimen can be administration of the long-acting hematopoietic factor at 1 day, 3 days, 5 days, 7 days, 9 days, 11 days, 13 days, 15 days and 17 days after radiation exposure. In another embodiment, the step of administering is initiated at about 24 hours after exposure followed by additional administration of a long acting hematopoietic factor protein analog using a once per week dosing regimen. For example a once per week dosing regimen can be administration of a single dose of the long-acting hematopoietic factor at about 24 hours after exposure, followed by another dose one week after exposure, followed by another dose the second week after exposure, followed by another dose the third week after exposure, followed by another dose the fourth week after exposure, and followed by another dose the fifth week after exposure. The per week dosing regimen can occur for about two weeks, three weeks, four weeks, five weeks, six weeks, seven weeks, eight weeks, nine weeks or ten weeks. In another embodiment, the dose may be administered once every two weeks following exposure to radiation. In still another embodiment, the dose may be administered once every three weeks following exposure to radiation. In yet another embodiment, the dose may be administered once every four weeks following exposure to radiation. In still other embodiments, more than one dose weekly may be administered.

Doses may be administered to the subject until hematopoietic recovery is achieved. This includes for example, a return of the subject's red blood cell level, platelet level and/or both levels to levels found in subjects that have not been exposed to radiation (e.g. normal levels for a subject of the same gender and similar age group and weight range). This also includes for example, a return of the subject's neutrophil level, red blood cell level, platelet level and/or any combination of two or more of these blood cell levels to levels found in subjects that have not been exposed to radiation (e.g. normal levels for a subject of the same gender and similar age group and weight range). This also includes for example, a return of the subject's neutrophil level, white blood cell level, lymphocyte level and/or any combination of two or more of these blood cell levels to levels found in subjects that have not been exposed to radiation (e.g. normal levels for a subject of the same gender and similar age group and weight range). This also includes for example, a return of the subject's neutrophil level, red blood cell level, platelet level, lymphocyte level and/or any combination of two or more of these blood cell levels to levels found in subjects that have not been exposed to radiation (e.g. normal levels for a subject of the same gender and similar age group and weight range).

In still further embodiments of the invention, the dose may be administered to the subject until several days after the subject's blood cell nadir occurs (low point of blood counts). The nadir time typically occurs between days 10-30 following exposure to radiation and is dependent upon the blood cell type (white blood cells, red blood cells, platelets, neutrophils, etc.). For instance, the nadirs for neutrophils, white blood cells, lymphocytes and platelets typically are about 10-20 days following radiation exposure. The time to reach the neutrophil and white blood cell nadir typically is longer in ARS subjects (15 days or more) than in chemotherapy-treated subjects (about 7 days). Red blood cell nadirs, hematocrit nadirs and hemoglobin nadirs typically occur later, between days 20-30 following radiation exposure, due to the longer half-life of red blood cells in the body.

In another embodiment, the method of the present invention is directed toward the administration of one or more single effective doses of a long-acting hematopoietic factor protein prior to a subject's radiation exposure to reduce the severity of radiation-related complications. In one aspect, the prior administration of the long-acting hematopoietic factor protein analog may prevent radiation-related complications. In another aspect, the administration of an effective dose of a long-acting hematopoietic factor protein analog prior to a subject's radiation exposure accelerates hematopoietic recovery after the subject is exposed to radiation. In one embodiment, one or more single effective doses of the long-acting hematopoietic factor protein analog may be administered to the subject at least about 24 hours prior to exposure. In still another aspect, one or more single effective doses of the long-acting hematopoietic factor protein analog will be administered to the subject at least about 2 days, 5 days, 7 days, 15 days, 30 days, 45 days, 60 days, up to 6 months prior to the subject's exposure to radiation. In still another embodiment, the subject is administered one or more single effective doses of a long-acting hematopoietic factor protein analog at least about 20 hours, 10 hours or 5 hours prior to exposure to radiation. Effective dose amounts of the long-acting hematopoietic factor protein analog that are administered to the subject prior to the subject's exposure to radiation are similar to the effective dose amounts administered to a subject following exposure to radiation as discussed above. A single effective dose is at least about 0.1 µg per kg of the subject to which the long acting hematopoietic factor protein analog is administered, up to an including at least about 10 mg/kg, or any dose within this range. Doses may also be given to a subject following an every other day dosing regimen wherein one or more single doses are given over a period of time every other day prior to the subject's exposure to radiation. Doses may also be given to a subject following a once per week dosing regimen over a period of time prior to exposure to radiation.

Suitable administration protocols include any in vivo or ex vivo administration protocol. preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue. Routes useful for deliver to mucosal tissues include, bronchial, intradermal, intramuscular, intranasal, other inhalatory, rectal, subcutaneous, topical, transdermal, vaginal and urethral routes. Combinations of routes of delivery can be used and in some instances, may enhance the therapeutic effects of the composition. Particularly preferred routes of delivery include subcutaneous and intravenous delivery.

Ex vivo administration refers to performing part of the regulatory step outside of the patient, such as administering a composition of the present invention to a population of cells removed from a patient under conditions such that the composition contacts and/or enters the cell, and returning the cells to the patient. Ex vivo methods are particularly suitable when the target cell type can easily be removed from and returned to the patient.

Many of the above-described routes of administration, including intravenous, intraperitoneal, intradermal, and intramuscular administrations can be performed using methods standard in the art. Aerosol (inhalation) delivery can also be performed using methods standard in the art (see, for example, Stribling et al., *Proc. Natl. Acad. Sci. USA* 189: 11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering a composition to a cell or tissue that is accessible by surgery, and particularly, on or near the surface of the body. Administration of a composition locally within the area of a target cell refers to injecting the composition centimeters and preferably, millimeters from the target cell or tissue.

The present invention is also directed toward a pharmaceutical composition comprising one or more long-acting hematopoietic factor protein analogs and a pharmaceutical acceptable carrier. In one embodiment, the protein analog is selected from a long-acting G-CSF analog, a long-acting GM-CSF analog, a long-acting GH analog or a long-acting IL-11 analog. In still another embodiment, the pharmaceutical composition is administered to the patient following radiation exposure.

Long acting hematopoietic factor protein analogs of the present invention are preferably administered in a composition. Compositions can include a long acting hematopoietic factor protein analog of the invention and any other suitable pharmaceutically acceptable carrier, as well as, in some aspects, additional components that may be useful in the treatment of radiation exposure. According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably any site where the long acting hematopoietic factor protein analog will provide a detectable effect as compared to in the absence of the long acting hematopoietic factor protein analog. Preferred pharmaceutically acceptable carriers are capable of maintaining the long acting hematopoietic factor protein analog of the present invention in a form that, upon arrival of the analog at the cell target in a culture or in a subject, the analog is capable of interacting with its target (e.g., hematopoietic cell for GM-CSF).

Suitable excipients of the present invention include excipients or formularies that transport or help transport, but do not specifically target a composition to a cell or area (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Compositions of the present invention can be sterilized by conventional methods and/or lyophilized.

One type of pharmaceutically acceptable carrier includes a controlled release formulation that is capable of slowly releasing a composition of the present invention into a subject or culture. As used herein, a controlled release formulation comprises a cysteine mutein of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other carriers of the present invention include liquids that, upon administration to a subject, form a solid or a gel in situ. Preferred carriers are also biodegradable (i.e., bioerodible). In the event that a long acting hematopoietic factor protein analog of the invention is administered as a recombinant nucleic acid molecule encoding the analog (e.g., gene therapy or genetic immunization), suitable carriers include, but are not limited to liposomes, viral vectors or other carriers, including ribozymes, gold particles, poly-L-lysine/DNA-molecular conjugates, and artificial chromosomes. Natural lipid-containing carriers include cells and cellular membranes. Artificial lipid-containing carriers include liposomes and micelles.

A carrier of the present invention can be modified to target to a particular site in a subject, thereby targeting and making use of a compound of the present invention at that site. A pharmaceutically acceptable carrier which is capable of targeting can also be referred to herein as a "delivery vehicle" or "targeting carrier". Suitable modifications include manipulating the chemical formula of the lipid portion of the delivery vehicle and/or introducing into the vehicle a targeting agent capable of specifically targeting a delivery vehicle to a preferred site or target site, for example, a preferred cell type. A "target site" refers to a site in a patient to which one desires to deliver a composition. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One delivery vehicle of the present invention is a liposome. A liposome is capable of remaining stable in an animal for a sufficient amount of time to deliver a nucleic acid molecule or protein described in the present invention to a preferred site in the animal. A liposome, according to the present invention, comprises a lipid composition that is capable of delivering a nucleic acid molecule or protein to a particular, or selected, site in a patient. A liposome according to the present invention comprises a lipid composition that is capable of fusing with the plasma membrane of the targeted cell to deliver a nucleic acid molecule or protein into a cell. Suitable liposomes for use with the present invention include any liposome. Preferred liposomes of the present invention include those liposomes commonly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule or protein of the present invention can be achieved using methods standard in the art.

Another type of delivery vehicle, when the long acting hematopoietic factor protein analog is administered as a nucleic acid encoding the analog, comprises a viral vector. A viral vector includes an isolated nucleic acid molecule, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

The data presented in the following examples, demonstrate the use of PEG-G-CSF (BBT-015) and PEG-GM-CSF (BBT-007) to serve as effective medical countermeasures against high radiation exposure via increasing hematopoietic recovery and subject survival. Unexpectedly, the inventors discovered that these proteins accelerate recovery of multiple hematopoietic cell lineages including neutrophils, white blood cells, lymphocytes, red blood cells, and platelets following radiation exposure. The inventors discovered that these proteins also accelerate recovery of hemoglobin and hematocrit levels following radiation exposure. Surprisingly, previous studies with G-CSF and GM-CSF analogs suggested that treatment with these proteins had no effect or decreased platelet and red blood cell levels (see for example Cox et al., 2004), which is contrary to the findings of the present invention.

The following experimental results are provided for purposes of illustration and are not intended to limit the scope of the invention.

EXAMPLES

Hematopoietic Screening Assay:

The Test Articles (TA) were PEG-G-CSF analog BBT-015 or PEG-GM-CSF analog BBT-007 (the murine BBT-007 GM-CSF homolog T3C modified with a 40 kDa-PEG was used for the mouse irradiation experiments described in the Examples). The Test Article and Control Article (CA; vehicle solutions) were administered by subcutaneous injection beginning 24+4/−0 hr after irradiation, then on days 3, 5, 7, 9, 11, 13, 15, and 17 for 9 doses. The test articles doses tested were 100 µg/kg=2.0 µg/20 gm mouse and 300 µg/kg=6.0 µg/20 gm mouse. The proteins were diluted in their respective vehicle solutions, which was 10 mM sodium acetate, pH 4.5, 140 mM NaCl for BBT-015 PEG-G-CSF analog and 10 mM sodium acetate, pH 4.8, 140 mM NaCl for the BBT-007 PEG-GM-CSF analog. The volume of injection per mouse was about 100 µL. Mice are weighed during the acclimation period and an average weight of all females and all males was calculated separately. All females were dosed based on the average weight of the females, and all males were dosed based on the average weight of the males. The volume of Test Article was adjusted to deliver a dose of approximately 2.0 µg or 6.0 µg to each mouse, slightly less than 100 µL to the females, and slightly more than 100 µL to the males. Weights were not to be taken again during the study; mice continued to be dosed based on the weight taken during the acclimation period.

Mice: Mus musculus/C57BL/6 strain, aged 10-12 weeks upon study initiation were used for these studies. The weight range for the females was 15 gm to 21.5 gm and for the males was 19 gm to 28 gm. There were 19-20 animals per group, 50% males and 50% females. Each study had 6 test groups as indicated below. An LD50/30 is the dose of radiation expected to cause death to 50% of an exposed population within 30 days. An LD 70/30 is the dose of radiation expected to cause death to 70% of an exposed population within 30 days. In general, the number immediately following the LD refers to the expected mortality, whereas the number following the slash refers to the timeframe over which one observes the mortality.

Group 1. Test Article, 100 µg/kg, 24+4/−0 hr after LD50/30 irradiation, then on days 3, 5, 7, 9, 11, 13, 15, and 17 for 9 doses (10 Female (F), 10 Male (M))

Group 2. Test Article, 300 µg/kg, 24+4/−0 hr after LD50/30 irradiation, then on days 3, 5, 7, 9, 11, 13, 15, and 17 for 9 doses (10F, 10M)

Group 3. Control Article, 24+4/−0 hr after LD50/30 irradiation, then on days 3, 5, 7, 9, 11, 13, 15, and 17 for 9 doses (10F, 10M)

Group 4. Test Article, 100 µg/kg, 24+4/−0 hr after LD70/30 irradiation, then on days 3, 5, 7, 9, 11, 13, 15, and 17 for 9 doses (10F, 10M)

Group 5. Test Article, 300 µg/kg, 24+4/−0 hr after LD70/30 irradiation, then on days 3, 5, 7, 9, 11, 13, 15, and 17 for 9 doses (10F, 10M)

Group 6. Control Article, 24+4/−0 hr after LD70/30 irradiation, then on days 3, 5, 7, 9, 11, 13, 15, and 17 for 9 doses (10F, 10M)

After the mice were received, they were placed in cages by sex (up to 5 mice per cage) and a sequentially numbered tattoo was applied to each mouse as well as a specific cage marking. Cages were randomized to either LD50/30 (grps. 1,2,3) or LD70/30 (grps. 4,5,6) doses of radiation. Mice were individually randomized to one of the three Test Article and Control Article groups within each radiation exposure group, with no more than 2 mice per group randomized into each cage. Mice were provided acidified water (pH 2.0-3.0) in bottles and fed certified commercial extruded laboratory animal chow (HARLAN 2018SXC) throughout the study. On day 4 post-exposure, mice were provided acidified autoclaved water in bottles and also in wetted chow (HARLAN 2018SXC) in a petri dish set in the bottom of the cage.

Complete Blood Cell Counts (CBCs) with differential and peripheral smears were performed at baseline and on study days 10, 20, 25, and 30. Two randomly selected mice/group in different cages were bled on day −3 to day −1 for a total of 12 baseline CBCs. Four randomly selected mice/group were be bled on days 10, 20, 25, and 30 for a total of eight TA-100 µg mice, eight TA-300 µg mice, and eight CA mice (four mice per radiation dose group) at each time point. When possible, the same number of males and females in each group and in separate cages were selected for bleeding. Each mouse was bled a maximum of two times during the study and bleeds were at least 14 days apart. Therefore, mice bled at baseline were not be eligible for bleeding until day 20, and mice bled on day 10 were not be eligible until day 25. Efforts were made to select mice at each time point that had not been previously bled. CBCs with differentials and peripheral smears also were performed on four non-irradiated age-matched control mice/time point as hematology controls.

Radiation Parameters: A dose of radiation equal to the LD50/30 or LD70/30 was delivered as a single uniform total body dose of gamma radiation from a $^{137}$Cs radiation source (GAMMACELL 40; Nordion International, Kanata, Ontario, Canada) at an exposure rate of 65-69 cGy/minute+/−2.5 cGy. Pilot studies determined the LD50/30 dose of radiation to be 776cGy and LD70/30 to be 796cGy. Each group of mice irradiated together in the same irradiation pie was roughly divided among all groups to ensure that each group received the same irradiation exposure conditions.

Experimental Design: The efficacy of the TA to increase 30 day survival was tested at two different doses of TA (100 µg/kg and 300 µg/kg) and at two different doses of radiation, the LD50/30 and LD70/30. Mice were monitored for survival once/day until signs of early euthanasia appear, then twice/day until day 30. Endpoints for the study were 30 day overall survival, mean survival time (MST) and CBC analyses.

Statistics: The proportion of mice that survive for 30-days were presented for each treatment and radiation dose group and by treatment group, radiation dose and gender. Logistic Regression was used to compare overall 30-day survival between each treatment group and the control, adjusted for radiation dose. The model also included gender. MST among decedents was presented by group. MST comparisons between each treatment group and the control was performed using analysis of variance (ANOVA) including radiation dose as a factor. Kaplan-Meier Survival Curves were used to present survival data by group. A time-to-event analysis was also performed on the survival data using a Cox proportional hazards regression model to compare the time to death of the treatment groups with radiation dose as a covariate. CBC results were compared among treatments using three-way ANOVA with treatment, bleed day and radiation dose as factors. If individual mice were bled more than once, then a random mouse effect was included in the model. Pair-wise follow-up comparisons of each treatment to the control were also performed. Thirty day mortality and Cox regression analyses for treatment comparisons were carried out using a one-tailed 5% significance level. All other tests were conducted as two-sided.

Example 1: Hematopoietic Screening Assay for Radiomitigating Activity of Subcutaneously Administered PEG-G-CSF Analog BBT-015

This example demonstrates that the dose of PEG-G-CSF analog BBT-015 (100 µg/kg/day or 300 µg/kg/day), administered every other day for a total of 9 doses beginning 24 hr after exposure to lethal doses of ionizing radiation, is efficacious to increase 30 day survival and overall survival time of C57BL/6 mice. The data also indicate that PEG-G-CSF analog BBT-015 is efficacious at accelerating recovery of multiple types of hematopoietic cells, including neutrophils, white blood cells, lymphocytes, red blood cells and platelets, compared to vehicle solution, following exposure to radiation. The data also indicate that PEG-G-CSF analog BBT-015 is more efficacious at accelerating recovery of hemoglobin and hematocrit levels than vehicle solution following exposure to radiation.

Radiation Exposure:

Groups 1, 2, and 3 were exposed to 776cGy of radiation delivered as 62.296cGy/min (12 min 28 sec exposure); this radiation dose was estimated to be the LD50/30 without antibiotics.

Groups 3, 4, and 5 were exposed to 796cGy of radiation delivered as 62.296cGy/min (12 min 47 sec exposure); this radiation dose was estimated to be the LD70/30 without antibiotics.

Mice were irradiated between 8:50 am and 11:37 am in groups of 10-15 mice.

The average weights (grams) of the male mice were 24.9±1.5; range=19.6-27.8 and the average weights of the female mice were 18.3±1.0; range=16.6-20.3. There was no statistical evidence of a cage effect observed in this study.

One control mouse in Group 6 was administered an incorrect compound and was excluded from the analysis.

Thirty Day Survival Results (Table 1 and FIG. 1)

Pooled Data from Both Radiation Dose Groups Combined (776+796cGy)

Thirty day survival of mice treated with 100 µg/kg/day of PEG-G-CSF analog BBT-015 every other day for 9 doses between days 1-17 was significantly increased (70.0% survival) compared to vehicle-treated mice (28.2% survival, p<0.001). Thirty day survival of mice treated similarly with 300 µg/kg/day PEG-G-CSF analog BBT-015 was also significantly increased (62.5% survival) compared to vehicle (28.2% survival, p<0.001). Thirty day survival of female mice was significantly increased compared to males (p<0.001, data not shown). Thirty day survival of female mice was greater than males for both BBT-105 dose groups and the control group.

Figure 2:
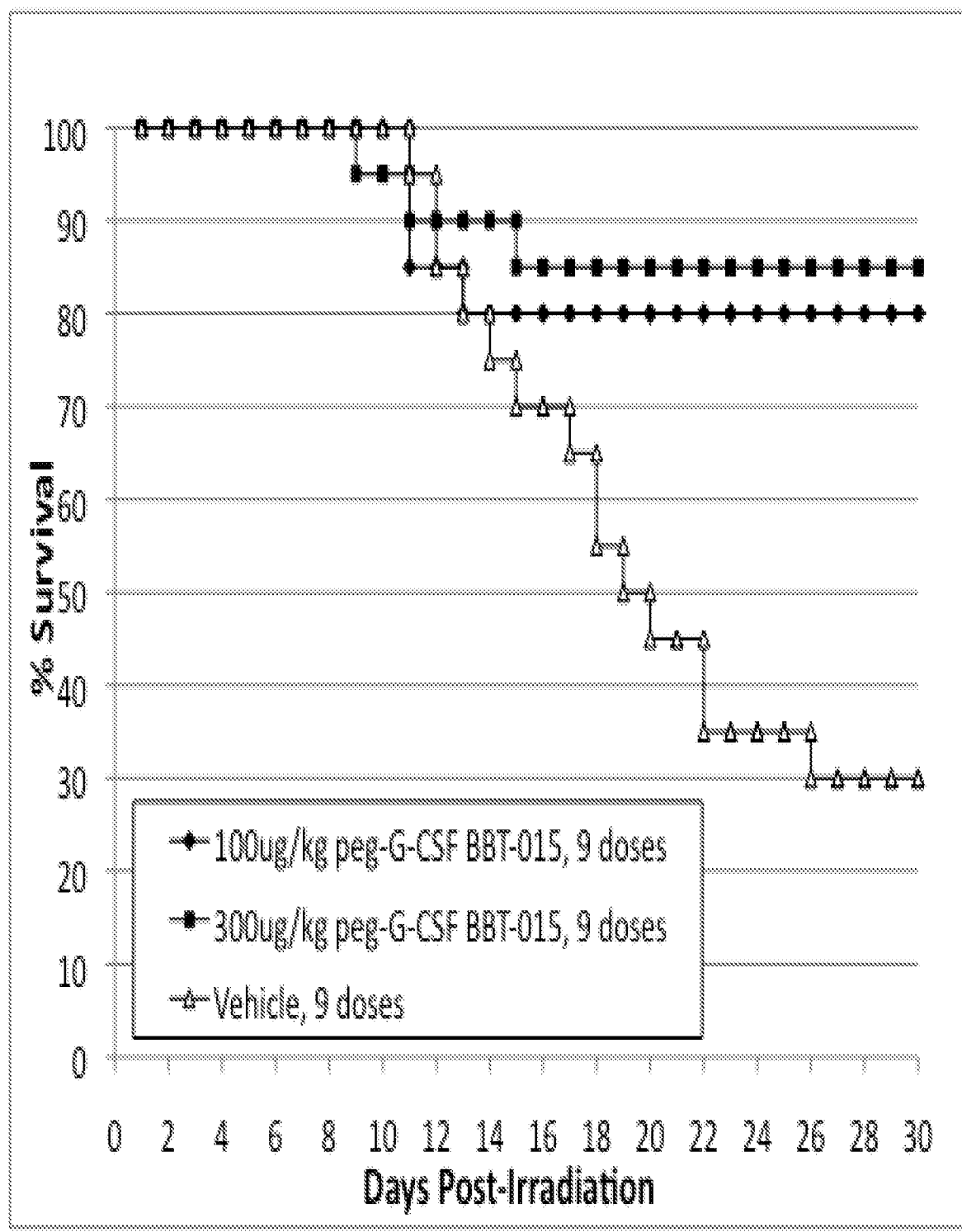
FIG. 2. Kaplan-Meier Survival Curves; 776cGy dose groups only. Mice were exposed to 776cGy and injected subcutaneously with either 100 µg/kg/day or 300 µg/kg/day peg-G-CSF analog BBT-015 for 9 doses (every other day from d1 to d17; filled symbols). Control mice were similarly injected but with vehicle (open symbols). Mice were not treated with antibiotics. N=20 mice per group.

776cGy Radiation Dose Groups Only (Table 1, FIG. 2):

Thirty day survival of mice exposed to 776cGy and treated with 9 doses of 100 µg/kg of PEG-G-CSF analog BBT-015 was 80%, whereas similar treatment with 300 µg/kg resulted in 85% survival. Thirty day survival of controls was lower at 30%.

Figure 3:
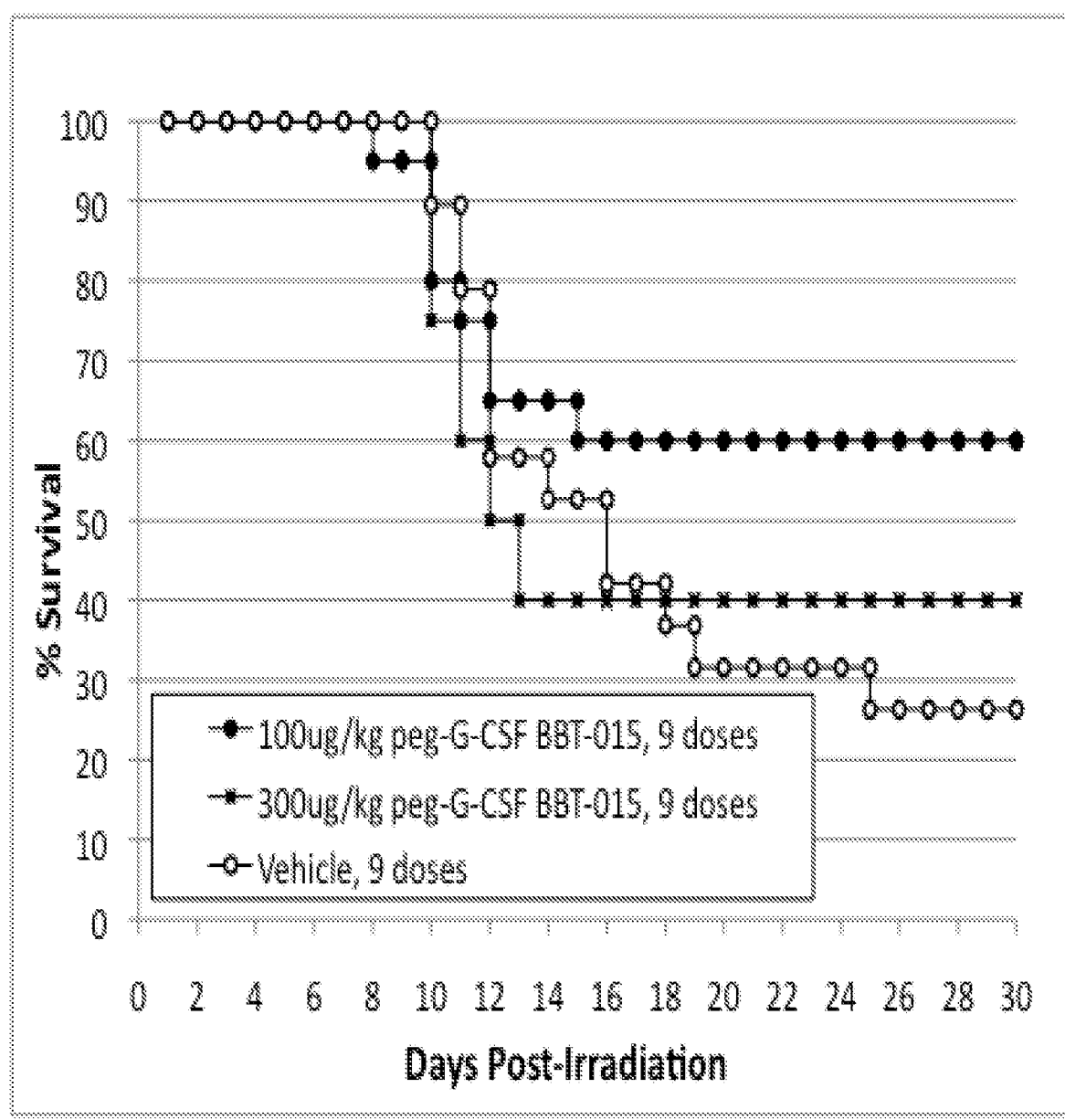
FIG. 3. Kaplan-Meier Survival Curves; 796cGy dose groups only. Mice were exposed to 796 cGy and injected subcutaneously with either 100 µg/kg/day or 300 µg/kg/day peg-G-CSF analog BBT-015 for 9 doses (every other day from d1 to d17; filled symbols). Control mice were similarly injected but with vehicle (open symbols). Mice were not treated with antibiotics. N=20 mice per group.
Figure 4:
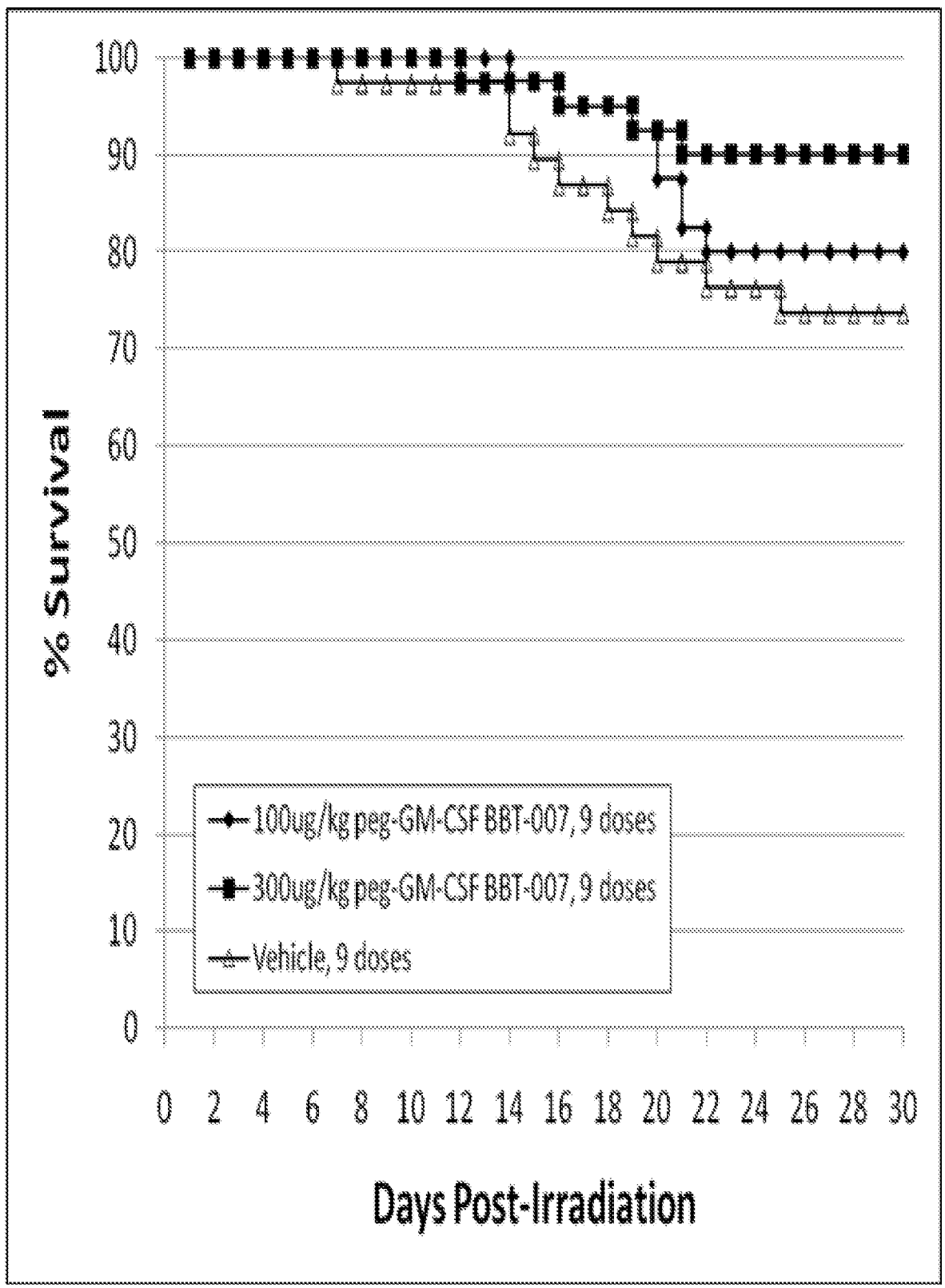
FIG. 4. Kaplan-Meier Survival Curves; pooled data from both radiation dose groups (776+796cGy). Mice were exposed to 776cGy or 796cGy and injected subcutaneously with either 100 µg/kg/day or 300 µg/kg/day peg-GM-CSF analog BBT-007 for 9 doses (every other day from d1 to d17; filled symbols). Control mice were similarly injected but with vehicle (open symbols). Thirty-day survival (p=0.343) and overall survival time (p=0.233) were not significantly different in mice treated with 100 µg/kg/day of peg-GM-CSF analog BBT-007. However, thirty-day survival of mice treated with 300 µg/kg/day of peg-GM-CSF analog BBT-007 was marginally increased (p=0.050), and overall survival time (p=0.037) was significantly increased, compared to controls. Mice were not treated with antibiotics. N=40 mice per group.

796cGy Radiation Dose Groups Only (Table 1, FIG. 3):

Thirty day survival of mice exposed to 796cGy and treated with 9 doses of 100 µg/kg of PEG-G-CSF analog BBT-015 was 60%, whereas 300 µg/kg resulted in 40% survival. Survival in control mice was 26.3%.

TABLE 1

Thirty Day Survival, Mean Survival Time (MST), and Overall Survival Time

| Group Description | Rad Dose in cGy | No. of Survivors/ Total | 30 day Survival (%) | MST of Decedents (days) | 30 d Survival (p value vs. Vehicle) | MST (p value vs. Vehicle) | Overall Survival Time (p value vs. Vehicle) |
| --- | --- | --- | --- | --- | --- | --- | --- |
| PEG-G-CSF analog BBT-015 (100 µg/kg/day × 9 doses) | 776 796 | 16/20 12/20 | 80 60 | 11.5 11.0 | <0.001 | <0.001 | 0.003 |
| PEG-G-CSF analog BBT-015 (300 µg/kg/day × 9 doses) | 776 796 | 17/20 8/20 | 85 40 | 11.7 11.1 | <0.001 | 0.001 | 0.022 |
| Sodium acetate/NaCl control (9 doses) | 776 796 | 6/20 5/19 | 30 26.3 | 17.1 14.1 | | | |

Mean Survival Time (MST) of Decedent Mice; Pooled Data from Both Radiation Dose Groups Combined (776+796cGy, Table 1)

The MST of decedent mice treated with either dose of PEG-G-CSF analog BBT-015 was significantly less compared to controls (100 µg/kg/day MST=11.2 days, 300 µg/kg/day MST=11.2 days, and control MST=15.6 days, p<0.001 and 0.001, respectively, Table 1), which is a common finding when granulocytic growth factors are used as radiomitigators. Thirty day survival was higher for females compared to males when data were pooled (p<0.001).

Overall Survival Time; Pooled Data from Both Radiation Dose Groups Combined (776+796cGy, Table 1):

Cox Regression analysis of overall survival time of mice treated with 100 µg/kg/day PEG-G-CSF analog BBT-015 was significantly increased compared to controls (p=0.003; Table 1), as was the overall survival time of mice treated with 300 µg/kg/day of PEG-G-CSF analog BBT-015 (p=0.022; Table 1). The overall survival time of female mice was significantly longer compared to males (p<0.001, data not shown).

CBC Analyses: Days −3, 10, 20, 25, and 30 Days Post-Exposure (Table 2):

Peripheral blood obtained from mice on days −3, 10, 20, 25, and 30 was analyzed for Complete Blood Count (CBC) by HEMAVET. Blood from age-matched non-irradiated mice was likewise analyzed. Many CBC parameters were significantly increased in mice treated with PEG-G-CSF BBT-015 compared to controls, as described below and shown in Table 2, particularly on days 20 and 25 post-irradiation, indicating accelerated hempatopoietic recovery in the BBT-015 treated mice compared to controls.

Significant overall differences were found in the white blood cell (WBC) count (p=0.001), absolute neutrophil count (ANC) (p<0.001), red blood cell (RBC) count (p=0.003), hemoglobin (p<0.001), hematocrit level (p<0.001), and platelet count (p=0.001). The mean WBC for the Control Article was significantly lower compared to Test Article, 100 µg/kg, and Test Article, 300 µg/kg (p=0.003, p<0.001). The mean ANC for the Control Article was significantly lower compared to Test Article, 100 µg/kg, and Test Article, 300 µg/kg (p<0.001, p<0.001). The mean RBC for the Control Article was significantly lower compared to Test Article, 100 µg/kg, and Test Article, 300 µg/kg (p<0.001, p=0.022). The mean hemoglobin level for the Control Article was significantly lower compared to Test Article, 100 µg/kg and Test Article, 300 µg/kg (p<0.001, p<0.001). The mean hematocrit level for the Control Article was significantly lower compared to Test Article, 100 µg/kg, and Test Article, 300 µg/kg (p=<0.001, p=0.001). The mean platelet count for the Control Article was significantly lower compared to Test Article, 100 µg/kg, and Test Article, 300 µg/kg (p<0.001, p=0.003).

The Complete Blood Cell (CBC) parameters for this example are shown in Table 2. CBCs were performed at baseline (day −3) and on study days 10, 20, 25, and 30 from randomly selected male and female mice exposed to 776 or 796cGy ionizing radiation and treated with 100 or 300 µg/kg/day PEG-G-CSF analog BBT-015 every other day for a total of 9 doses. Data are presented as mean±SD. Abbreviations used are WBC (white blood cells; thousands per microliter); NE (neutrophils; thousands per microliter); Ly (lymphocytes; thousands per microliter); RBC (red blood cells; millions per microliter); Hb (hemoglobin, g/dL); Hct (hematocrit; percent); Plt (platelet, thousand per microliter). Control-NI are non-irradiated control mice.

accelerating recovery of multiple types of hematopoietic cells, including neutrophils, white blood cells, red blood cells, lymphocytes, and platelets, and for accelerating recovery of hemoglobin and hematocrit levels. The 100 µg/kg/day dosing regimen did not increase 30 survival time when data from both radiation doses were pooled, but did accelerate recovery of some hematopoietic cells. More mice receiving 100 µg/kg/day PEG BBT-007 survived for 30 days than did mice receiving the Control Article in the lower radiation dose (90% survival with PEG BBT-007 versus 74% survival to the Control Article group), indicating that PEG BBT-007 confers a survival benefit at this radiation dose. Doses of 100 µg/kg and 300 µg/kg in a mouse approximately correspond to doses of 8 µg/kg and 24 µg/kg, respectively in a human, adjusting for body weight differences between mice and humans.

General study information: Groups 1, 2, and 3 were exposed to radiation doses of 776cGy delivered as 62.177cGy/min (12 min 29 sec exposure), estimated to be the LD50/30 without antibiotics. Groups 4, 5, and 6 were exposed to radiation doses of 796cGy delivered as 62.177cGy/min (12 min 48 sec exposure), estimated to be the LD70/30 without antibiotics. The average weight (grams) of the male mice was 25.4±1.3; range=21.4-28.2. The average weight (grams) of the female mice was 18.3±1.0; range=17.5-21.5. There was no statistical evidence of a cage effect in this study.

CBC PARAMETERS TABLE 2

| Group | Day | WBC mean | WBC SD | NE mean | NE SD | Ly mean | Ly SD | RBC mean | RBC SD | Hb mean | Hb SD | Hct mean | Hct SD | Plt mean | Plt SD |
|---|---|---|---|---|---|---|---|---|---|---|---|---|---|---|---|
| Control-NI | −3 | 17.81 | 3.14 | 4.55 | 1.20 | 11.52 | 1.98 | 10.56 | 0.80 | 14.1 | 1.1 | 50.0 | 3.3 | 986 | 325 |
| group 1 | 10 | 0.30 | 0.09 | 0.06 | 0.04 | 0.18 | 0.02 | 6.43 | 1.12 | 7.0 | 1.5 | 28.6 | 5.8 | 73 | 25 |
| group 2 | 10 | 0.35 | 0.11 | 0.09 | 0.06 | 0.20 | 0.05 | 6.49 | 0.59 | 7.0 | 0.8 | 28.4 | 2.6 | 78 | 23 |
| group 3 | 10 | 0.31 | 0.09 | 0.09 | 0.01 | 0.23 | 0.04 | 5.18 | 1.70 | 5.4 | 2.0 | 22.5 | 7.6 | 45 | 28 |
| group 4 | 10 | 0.29 | 0.06 | 0.08 | 0.01 | 0.22 | 0.06 | 5.07 | 0.43 | 5.3 | 0.4 | 21.4 | 1.5 | 48 | 31 |
| group 5 | 10 | 0.33 | 0.10 | 0.08 | 0.02 | 0.22 | 0.10 | 4.20 | 0.73 | 4.3 | 0.9 | 17.8 | 3.4 | 41 | 17 |
| group 6 | 10 | 0.33 | 0.12 | 0.08 | 0.02 | 0.25 | 0.09 | 5.73 | 0.79 | 6.0 | 0.9 | 24.8 | 3.9 | 48 | 25 |
| Control-NI | 10 | 10.77 | 5.47 | 2.36 | 1.22 | 7.72 | 3.75 | 7.26 | 3.56 | 8.1 | 4.3 | 33.3 | 16.7 | 625 | 324 |
| group 1 | 20 | 9.50 | 12.03 | 1.89 | 0.57 | 6.72 | 11.35 | 6.84 | 1.15 | 10.7 | 1.9 | 38.5 | 6.4 | 405 | 153 |
| group 2 | 20 | 7.58 | 3.35 | 3.93 | 3.46 | 2.56 | 1.24 | 7.70 | 1.04 | 12.0 | 1.7 | 42.6 | 6.0 | 469 | 55 |
| group 3 | 20 | 1.99 | 1.05 | 0.50 | 0.41 | 1.35 | 0.86 | 3.58 | 1.38 | 5.1 | 2.4 | 19.1 | 8.7 | 193 | 104 |
| group 4 | 20 | 3.78 | 1.41 | 1.74 | 0.66 | 1.49 | 0.66 | 7.34 | 1.12 | 11.1 | 1.9 | 39.5 | 7.1 | 451 | 192 |
| group 5 | 20 | 7.87 | 6.65 | 4.25 | 5.61 | 3.04 | 3.96 | 5.11 | 2.21 | 8.0 | 3.2 | 29.0 | 11.4 | 402 | 149 |
| group 6 | 20 | 0.89 | 0.38 | 0.24 | 0.10 | 0.53 | 0.22 | 2.15 | 0.70 | 2.6 | 0.9 | 9.2 | 3.5 | 113 | 57 |
| Control-NI | 20 | 17.78 | 1.48 | 3.66 | 0.81 | 12.40 | 1.07 | 10.52 | 0.65 | 14.6 | 0.9 | 48.4 | 2.7 | 963 | 165 |
| group 1 | 25 | 6.81 | 0.55 | 4.87 | 0.16 | 1.35 | 0.32 | 9.01 | 1.22 | 12.6 | 1.9 | 44.7 | 5.8 | 685 | 207 |
| group 2 | 25 | 11.30 | 11.32 | 3.42 | 0.82 | 7.08 | 11.57 | 7.96 | 1.96 | 11.8 | 2.5 | 42.6 | 6.0 | 559 | 160 |
| group 3 | 25 | 4.13 | 4.24 | 2.68 | 3.88 | 1.19 | 0.66 | 3.93 | 3.63 | 5.7 | 5.7 | 21.2 | 21.0 | 333 | 384 |
| group 4 | 25 | 5.03 | 2.31 | 3.48 | 1.89 | 1.14 | 0.42 | 8.54 | 0.33 | 12.7 | 0.8 | 45.0 | 2.2 | 597 | 127 |
| group 5 | 25 | 4.28 | 2.54 | 2.82 | 2.18 | 0.98 | 0.37 | 8.23 | 1.41 | 12.3 | 2.3 | 44.7 | 7.2 | 422 | 184 |
| group 6 | 25 | 5.21 | 2.93 | 1.81 | 2.06 | 3.01 | 2.18 | 8.56 | 4.55 | 10.4 | 3.9 | 47.5 | 25.8 | 460 | 422 |
| Control-NI | 25 | 15.33 | 3.93 | 3.23 | 0.88 | 10.70 | 2.58 | 10.55 | 0.71 | 14.4 | 1.1 | 48.1 | 4.1 | 1057 | 239 |
| group 1 | 30 | 6.25 | 3.38 | 3.25 | 1.34 | 2.20 | 1.80 | 7.98 | 2.79 | 11.6 | 4.4 | 41.0 | 14.3 | 458 | 213 |
| group 2 | 30 | 6.55 | 2.03 | 3.22 | 0.73 | 2.17 | 0.75 | 9.88 | 2.36 | 12.1 | 1.2 | 50.5 | 11.6 | 588 | 208 |
| group 3 | 30 | 3.11 | 1.23 | 2.13 | 1.12 | 0.86 | 0.15 | 7.98 | 1.04 | 11.6 | 1.9 | 43.1 | 3.4 | 502 | 234 |
| group 4 | 30 | 6.26 | 1.99 | 3.68 | 1.36 | 2.00 | 1.27 | 9.39 | 1.76 | 11.0 | 3.1 | 46.3 | 7.9 | 571 | 278 |
| group 5 | 30 | 4.38 | 1.51 | 3.15 | 1.37 | 0.81 | 0.27 | 7.25 | 2.89 | 10.4 | 3.7 | 37.8 | 16.0 | 554 | 294 |
| group 6 | 30 | 5.65 | 0.52 | 3.82 | 0.38 | 1.28 | 0.11 | 9.17 | 2.48 | 11.6 | 1.1 | 51.4 | 13.8 | 604 | 238 |
| Control-NI | 30 | 17.42 | 4.05 | 3.69 | 0.92 | 11.55 | 2.66 | 10.89 | 0.32 | 15.1 | 0.4 | 52.0 | 3.0 | 1232 | 269 |

Example 2: Hematopoietic Screening Assay for Radiomitigating Activity of Subcutaneously Administered PEG-GM-CSF Analog BBT-007

This example demonstrates that 300 µg/kg/day of PEG-GM-CSF analog BBT-007, administered every other day for a total of 9 doses beginning 24 hr after exposure to lethal ionizing radiation, is efficacious for increasing 30 day survival and overall survival time of C57BL/6 mice, and for Two control mice (one in each radiation dose group) were inadvertently administered an incorrect compound and were excluded from the analysis.

Figure 5:
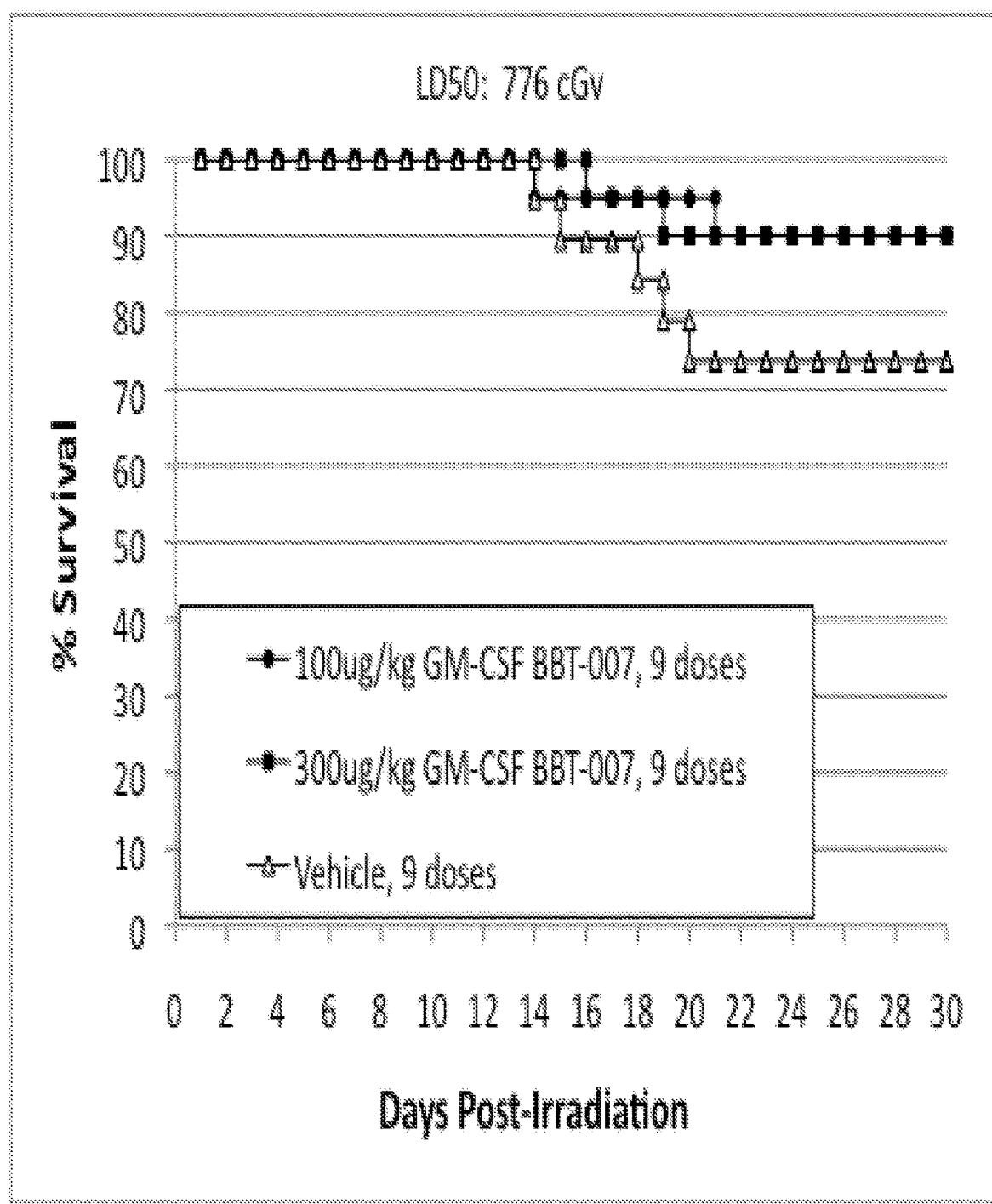
FIG. 5. Kaplan-Meier Survival Curves; 776cGy dose groups only. Mice were exposed to 776 cGy and injected subcutaneously with either 100 µg/kg/day or 300 µg/kg/day peg-GM-CSF analog BBT-007 for 9 doses (every other day from d1 to d17; filled symbols). Control mice were similarly injected but with vehicle (open symbols). Mice were not treated with antibiotics. N=20 mice per group.

Thirty Day Survival (Table 3 and FIG. 5)
Pooled Data from Both Radiation Dose Groups Combined (776+796cGy):

Thirty day survival of mice treated with 300 µg/kg/day of peg-GM-CSF analog BBT-007 every other day for 9 doses between days 1-17 was increased (90.0% survival) compared to vehicle-treated mice (73.7% survival, p=0.050). Thirty day survival of mice treated similarly with 100 µg/kg/day peg-GM-CSF analog BBT-007 was higher than controls (80% vs. 73.7% survival, respectively), but the difference was not statistically significant (p=343). Thirty day survival of female mice was significantly increased compared to males (p=0.002, data not shown).

Figure 6:
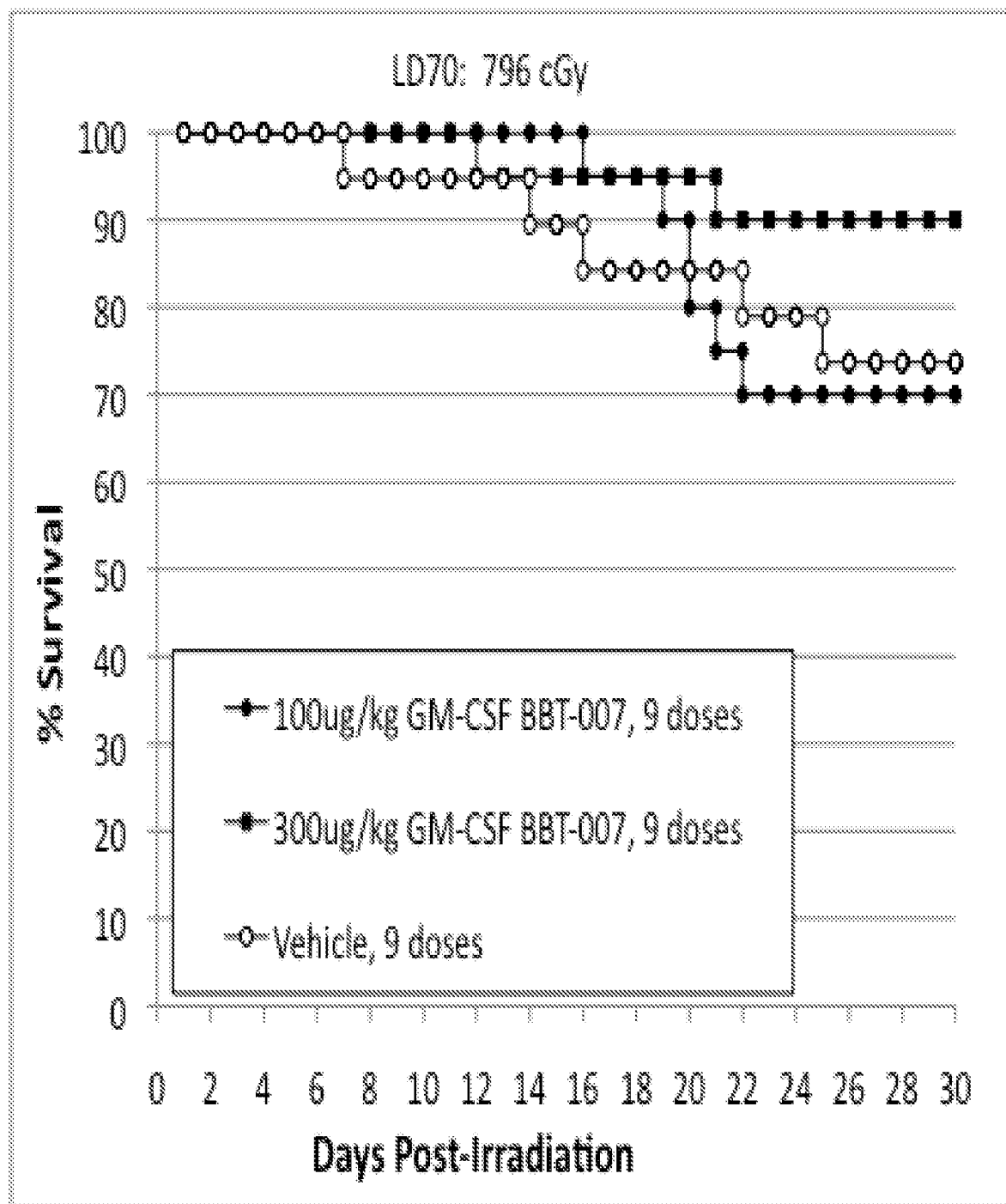
FIG. 6. Kaplan-Meier Survival Curves; 796cGy dose groups only. Mice were exposed to 796 cGy and injected subcutaneously with either 100 µg/kg/day or 300 µg/kg/day peg-GM-CSF analog BBT-007 for 9 doses (every other day from d1 to d17; filled symbols). Control mice were similarly injected but with vehicle (open symbols). Mice were not treated with antibiotics. N=20 mice per group.

776cGy Radiation Dose Groups Only (Table 3, FIG. 6)

Thirty day survival of mice exposed to 776cGy and treated with 9 doses of either 100 µg/kg or 300 µg/kg of peg-GM-CSF analog BBT-007 was 90%, which was higher than thirty day survival of controls (73.7%).

Figure 7:
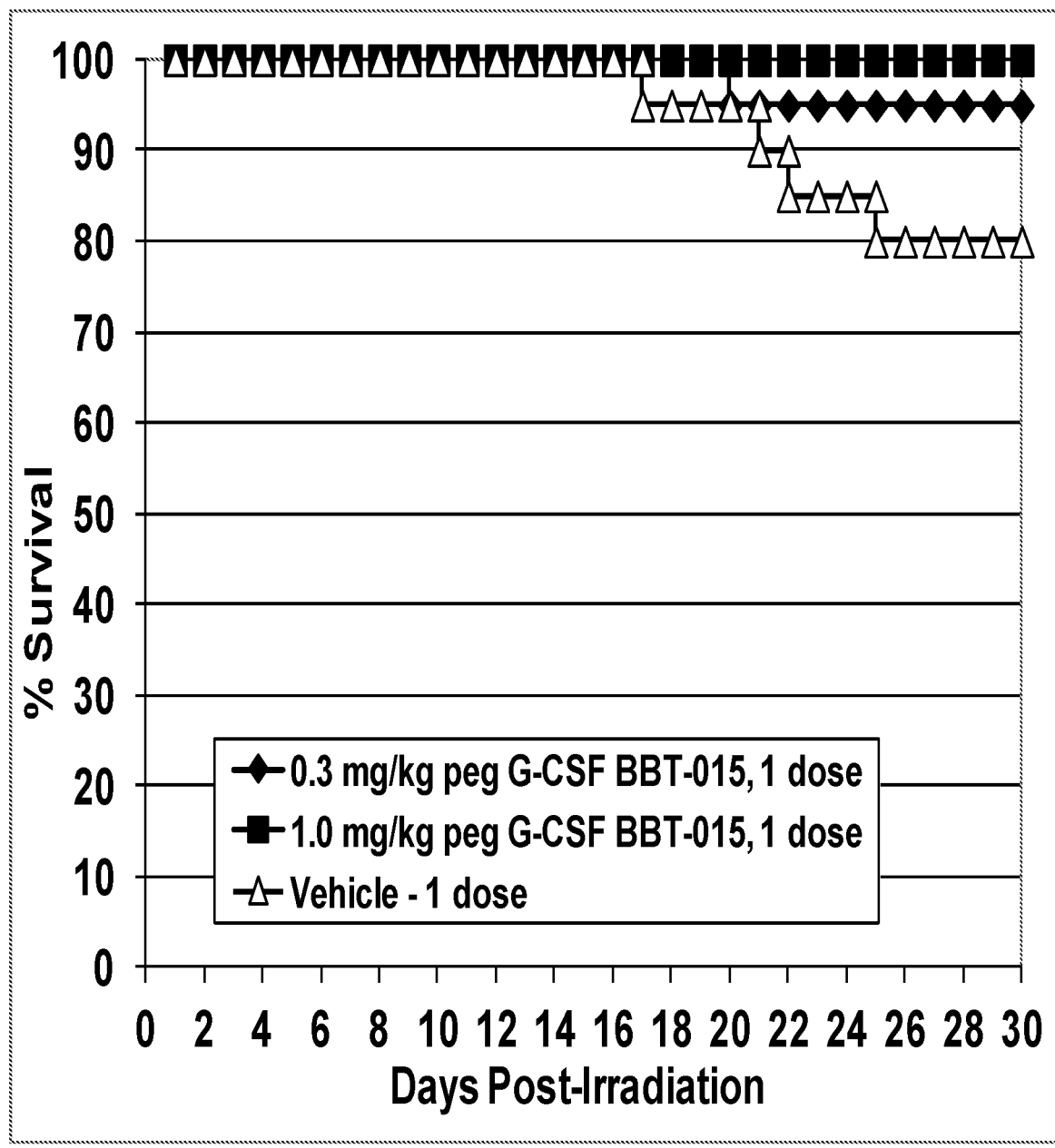
FIG. 7. Kaplan-Meier Survival Curves; pooled data from both radiation dose groups (786+810 cGy). Mice were exposed to 786 cGy or 810 cGy and injected subcutaneously with either 0.3 mg/kg or 1.0 mg/kg PEG-G-CSF analog BBT-015 on d1 after irradiation (filled symbols). Control mice were similarly injected but with vehicle (open symbols). Thirty-day survival was significantly increased in both groups of mice treated with 0.3 mg/kg or 1.0 mg/kg of PEG-G-CSF analog BBT-015 (p=0.001 and p>0.001, respectively). N=40 mice per group.

796cGy Radiation Dose Groups Only (Table 3, FIG. 7)

Thirty day survival of mice exposed to 796cGy and treated with 9 doses of 100 µg/kg of peg-GM-CSF analog BBT-007 was 70%, whereas 300 ug/kg resulted in 90% survival. Survival in control mice was 73.7%.

were significantly increased in mice treated with PEG-GM-CSF analog BBT-007 compared to controls, as described below and shown in Table 4.

There were significant overall treatment group differences in the white blood cell (WBC) count (p<0.001), absolute neutrophil count (ANC) (p<0.001), and absolute lymphocyte count (LY) (p=0.016). Marginally significant differences were found in red blood cell count (RBC) (p=0.063), hemoglobin (p=0.072), hematocrit (p=0.086), and platelet count (p=0.067). The mean WBC was significantly lower for the Control Article when compared to Test Article, 100 ug/kg and Test Article, 300 µg/kg (p<0.001, p<0.001). The mean ANC was significantly lower for the Control Article when compared to Test Article, 100 µg/kg and Test Article, 300 µg/kg (p<0.001, p<0.001). The mean LY was significantly lower for the Control Article when compared to Test Article, 100 µg/kg and Test Article, 300 µg/kg (p=0.015,

TABLE 3

Thirty Day Survival, Mean Survival Time (MST), and Overall Survival Time

| Group Description | Rad Dose in cGy | No. of Survivors/ Total | 30 day Survival (%) | MST of Decedents (days) | 30 d Survival (p value vs. Vehicle) | MST (p value vs. Vehicle) | Overall Survival Time (p value vs. Vehicle) |
|---|---|---|---|---|---|---|---|
| PEG-GM-CSF analog BBT-007 (100 µg/kg/day × 9 doses) | 776 | 18/20 | 90 | 17.5 | 0.343 | 0.332 | 0.233 |
|  | 796 | 14/20 | 70 | 19.7 |  |  |  |
| PEG-GM-CSF analog BBT-007 (300 µg/kg/day × 9 doses) | 776 | 18/20 | 90 | 17.5 | 0.050 | 1.000 | 0.037 |
|  | 796 | 18/20 | 90 | 16.5 |  |  |  |
| Sodium acetate/NaCl control (9 doses) | 776 | 14/19 | 73.7 | 17.2 |  |  |  |
|  | 796 | 14/19 | 73.7 | 16.8 |  |  |  |

Mean Survival Time (MST) of Decedent Mice; Pooled Data from Both Radiation Dose Groups Combined (776+796cGy, Table 3):

The MST of decedent mice treated with either dose of peg-GM-CSF analog BBT-007 was not significantly different compared to controls (100 µg/kg/day MST=19.1 days, 300 ug/kg/day MST=17.0 days, and control MST=17.0 days, p=0.332 and 1.000, respectively, Table 3).

Overall Survival Time; Pooled Data from Both Radiation Dose Groups Combined (776+796cGy, Table 3):

Cox Regression analysis of overall survival time of mice treated with 300 µg/kg/day PEG-GM-CSF analog BBT-007 was significantly increased compared to controls (p=0.037; Table 3). Overall survival time of mice treated with 100 µg/kg/day of PEG-GM-CSF was not different than controls (p=0.233; Table 3). The overall survival time of female mice was significantly longer compared to males (p=0.004, data not shown).

CBC Analyses: Days −1, 10, 20, 25, and 30 Days Post-Exposure (Table 4):

Peripheral blood obtained from the mice on days −1, 10, 20, 25, and 30 was analyzed for Complete Blood Count (CBC) by HEMAVET. Blood from age-matched non-irradiated mice was likewise analyzed. Many CBC parameters p=0.008). The mean RBC was significantly lower for the Control Article when compared to Test Article, 300 µg/kg (p=0.028). The mean hemoglobin level was significantly lower for the Control Article when compared to Test Article, 300 µg/kg (p=0.022). The mean hematocrit was significantly lower for the Control Article when compared to Test Article, 300 µg/kg (p=0.045). The mean platelet count was significantly lower for the Control Article when compared to Test Article, 300 µg/kg (p=0.034). Bleed day was significant for every complete blood count variable (p<0.001 for each variable).

The Complete Blood Cell (CBC) parameters for this example are shown in Table 4. CBCs were performed at baseline (day −1) and on study days 10, 20, 25, and 30 from randomly selected male and female mice exposed to 776 or 796cGy ionizing radiation and treated with 100 or 300 µg/kg/day PEG-GM-CSF analog BBT-007 every other day for a total of 9 doses. Data are presented as mean±SD. Abbreviations used are WBC (white blood cells; thousands per microliter); NE (neutrophils; thousands per microliter); Ly (lymphocytes; thousands per microliter); RBC (red blood cells; millions per microliter); Hb (hemoglobin, g/dL); Hct (hematocrit; percent); Plt (platelet, thousand per microliter). Control-NI are non-irradiated control mice.

CBC PARAMETERS TABLE 4

| Group | Day | WBC mean | WBC SD | NE mean | NE SD | Ly mean | Ly SD | RBC mean | RBC SD | Hb mean | Hb SD | Hct mean | Hct SD | Plt mean | Plt SD |
|---|---|---|---|---|---|---|---|---|---|---|---|---|---|---|---|
| Control-NI | −1 | 18.00 | 4.29 | 4.09 | 2.39 | 12.03 | 3.39 | 10.06 | 2.16 | 14.2 | 3.2 | 48.3 | 10.6 | 821 | 230 |
| group 1 | 10 | 0.40 | 0.07 | 0.11 | 0.01 | 0.23 | 0.05 | 6.30 | 1.90 | 8.1 | 2.4 | 28.1 | 9.0 | 55 | 15 |
| group 2 | 10 | 0.53 | 0.12 | 0.16 | 0.05 | 0.27 | 0.05 | 6.86 | 1.00 | 9.0 | 1.2 | 30.3 | 4.2 | 79 | 31 |
| group 3 | 10 | 0.34 | 0.07 | 0.09 | 0.01 | 0.25 | 0.05 | 5.90 | 1.26 | 7.3 | 1.4 | 26.2 | 5.7 | 68 | 32 |
| group 4 | 10 | 0.32 | 0.04 | 0.10 | 0.03 | 0.19 | 0.03 | 6.02 | 1.40 | 7.7 | 2.0 | 26.0 | 6.3 | 52 | 20 |
| group 5 | 10 | 0.43 | 0.08 | 0.15 | 0.05 | 0.21 | 0.02 | 6.94 | 0.96 | 9.1 | 1.4 | 30.6 | 4.2 | 76 | 32 |
| group 6 | 10 | 0.24 | 0.02 | 0.03 | 0.00 | 0.17 | 0.00 | 5.31 | 0.61 | 6.8 | 0.8 | 23.2 | 2.5 | 53 | 7 |
| Control-NI | 10 | 15.42 | 3.98 | 3.33 | 1.07 | 10.66 | 2.64 | 10.07 | 0.90 | 14.0 | 1.7 | 47.3 | 3.8 | 880 | 88 |
| group 1 | 20 | 7.35 | 5.99 | 1.36 | 0.43 | 5.21 | 5.83 | 5.56 | 2.24 | 8.6 | 3.3 | 32.5 | 12.5 | 308 | 105 |
| group 2 | 20 | 13.37 | 11.37 | 5.07 | 3.62 | 6.26 | 8.21 | 6.50 | 3.08 | 8.5 | 2.4 | 36.6 | 14.7 | 349 | 119 |
| group 3 | 20 | 1.75 | 2.15 | 0.36 | 0.27 | 1.23 | 1.72 | 2.04 | 0.91 | 2.6 | 1.2 | 9.1 | 4.6 | 96 | 85 |
| group 4 | 20 | 3.37 | 2.28 | 2.10 | 3.23 | 1.60 | 0.94 | 3.12 | 2.94 | 4.7 | 4.6 | 17.1 | 16.9 | 156 | 162 |
| group 5 | 20 | 6.75 | 4.40 | 1.64 | 0.81 | 4.27 | 3.84 | 4.64 | 1.78 | 7.3 | 3.3 | 27.0 | 12.4 | 265 | 130 |
| group 6 | 20 | 2.17 | 0.50 | 0.62 | 0.13 | 1.42 | 0.50 | 3.02 | 0.82 | 4.3 | 1.2 | 15.5 | 5.2 | 174 | 36 |
| Control-NI | 20 | 18.03 | 5.06 | 4.13 | 1.27 | 12.06 | 3.59 | 10.48 | 1.12 | 14.9 | 1.1 | 49.7 | 5.6 | 901 | 198 |
| group 1 | 25 | 6.26 | 1.18 | 3.79 | 0.57 | 1.88 | 0.63 | 7.01 | 0.91 | 10.6 | 0.8 | 39.0 | 3.8 | 597 | 305 |
| group 2 | 25 | 6.20 | 2.59 | 3.45 | 0.67 | 2.12 | 2.26 | 9.46 | 5.31 | 10.1 | 1.7 | 52.2 | 27.8 | 729 | 376 |
| group 3 | 25 | 3.38 | 1.32 | 1.69 | 1.03 | 1.31 | 0.26 | 6.44 | 2.88 | 9.6 | 4.2 | 35.8 | 15.7 | 427 | 194 |
| group 4 | 25 | 3.92 | 3.02 | 1.37 | 1.12 | 2.28 | 2.93 | 3.84 | 1.98 | 5.2 | 2.3 | 21.6 | 8.4 | 381 | 143 |
| group 5 | 25 | 5.02 | 2.90 | 2.56 | 1.36 | 2.06 | 1.58 | 5.42 | 1.78 | 7.5 | 2.0 | 30.4 | 10.8 | 476 | 229 |
| group 6 | 25 | 3.06 | 1.89 | 1.26 | 0.80 | 1.49 | 1.71 | 6.03 | 2.94 | 8.7 | 4.5 | 34.6 | 15.7 | 535 | 297 |
| Control-NI | 25 | 13.12 | 3.01 | 2.35 | 1.09 | 9.88 | 1.63 | 9.14 | 2.99 | 11.0 | 4.0 | 42.5 | 14.1 | 855 | 207 |
| group 1 | 30 | 7.56 | 5.05 | 3.81 | 2.69 | 2.89 | 2.02 | 7.29 | 2.86 | 10.4 | 4.3 | 36.9 | 15.2 | 579 | 259 |
| group 2 | 30 | 6.92 | 1.67 | 4.01 | 1.09 | 1.57 | 0.50 | 8.25 | 1.52 | 11.7 | 2.1 | 43.6 | 7.6 | 762 | 238 |
| group 3 | 30 | 3.77 | 1.74 | 1.93 | 1.31 | 1.35 | 0.51 | 9.31 | 2.13 | 10.4 | 3.1 | 53.4 | 18.2 | 715 | 165 |
| group 4 | 30 | 6.17 | 1.97 | 3.79 | 2.30 | 1.81 | 0.71 | 7.50 | 1.56 | 10.6 | 2.4 | 40.0 | 6.8 | 603 | 255 |
| group 5 | 30 | 6.62 | 1.20 | 3.89 | 0.59 | 2.04 | 0.74 | 9.02 | 0.51 | 12.3 | 0.3 | 47.2 | 1.7 | 672 | 197 |
| group 6 | 30 | 3.96 | 2.26 | 1.69 | 1.51 | 1.84 | 1.81 | 6.20 | 3.11 | 8.4 | 4.5 | 35.2 | 17.6 | 714 | 416 |
| Control-NI | 30 | 19.51 | 6.91 | 3.69 | 1.30 | 13.82 | 4.66 | 10.76 | 0.81 | 13.7 | 2.9 | 50.4 | 3.7 | 906 | 242 |

Example 3: A Single Administration of PEG-G-CSF Analog BBT-015 Improves 30 Day Survival of Lethally Irradiated Mice This example demonstrates that a single administration of BBT-015 administered 24 hours following a lethal dose of radiation is capable of significantly improving 30 day survival of mice compared to vehicle solution. The data also indicate that a single administration of BBT-015 administered 24 hours following a lethal dose of radiation is capable of significantly accelerating recovery of neutrophils, white blood cells, red blood cells, platelets, and hemoglobin and hematocrit levels in irradiated mice compared to vehicle solution. Differences between test groups for these parameters were most pronounced on Days 20 and 25 following radiation exposure.

The ability of a single administration of the PEG-G-CSF analog BBT-015 to increase 30 day survival in mice after radiation exposure was tested using two different BBT-015 doses (0.3 mg/kg and 1.0 mg/kg) and at two different doses of radiation, 786 cGy and 810 cGy. The protocol for this study was similar to the study protocols described in Examples 1 and 2 and is outlined in Table 5. Groups of C57BL/6 mice (N=10 males and 10 females per group) received one of six treatments in a randomized vehicle-controlled study (Table 5). Endpoints for this study were 30 day overall survival, mean survival time and CBC analyses. The radiation dose was delivered as a single uniform total body dose of gamma radiation from a 137Cs radiation source at an exposure rate of 65-69 cGy/minute+/−2.5 cGy. BBT-015 or vehicle solution (10 mM sodium acetate, pH 4.5, 140 mM NaCl) was subcutaneously administered once to 10-12 week old mice 24+4/−0 hours after irradiation treatment. Mice were weighed during the acclimation period and an average weight of all females and all males were calculated separately. All females were dosed based on the average weight of the females, and all males dosed based on the average weight of the males. The volume of BBT-015 was adjusted to deliver a dose of approximately 6.0 µg (about 0.3 mg/kg) or 20.0 µg (about 1 mg/kg) to each mouse, slightly less than 1004, to the females, and slightly more than 100 µL to the males. These BBT-015 doses in mice (0.3 mg/kg and 1.0 mg/kg) correspond to equivalent human doses of about 0.024 mg/kg and 0.081 mg/kg, respectively, due to faster clearance of protein therapeutics in mice compared to humans. An equivalent volume of vehicle solution was administered to those mice in the control groups. Weights were not taken again during the study; mice were dosed based on the weight taken during the acclimation period.

TABLE 5

A single administration of BBT-015 improves 30 day survival of irradiated mice.

| Group | Treatment | Drug Dose | Radiation Dose | Numbers and Sex of Animals | Number of survivors on Day 30 (%) |
|---|---|---|---|---|---|
| 1 | BBT-015 | 0.3 mg/kg | 786 cGy | 10F, 10M | 19/20 (95%) |
| 2 | BBT-015 | 1.0 mg/kg | 786 cGy | 10F, 10M | 20/20 (100%) |
| 3 | Vehicle (control) | N/A | 786 cGy | 10F, 10M | 16/20 (80%) |
| 4 | BBT-015 | 0.3 mg/kg | 810 cGy | 10F, 10M | 19/20 (95%) |
| 5 | BBT-015 | 1.0 mg/kg | 810 cGy | 10F, 10M | 20/20 (100%) |
| 6 | Vehicle (control) | N/A | 810 cGy | 10F, 10M | 10/20 (50%) |

CBC with differential and peripheral smears were performed at baseline (day −4) and on study days 10, 20, 25, and 30 as described in Examples 1 and 2. CBCs with differentials and peripheral smears were also performed on four non-irradiated age-matched control mice/time point as hematology controls. Mice were monitored for survival once a day until signs of early euthanasia appear, then twice/day until day 30. Data are presented in Table 6.

As shown in Tables 5 and 6, and FIGS. 8, 9 and 10, 30 day survival of mice exposed to 786cGy and treated with 1 administration of 0.3 mg/kg or 1 mg/kg of BBT-015 was 95% and 100%, respectively, as compared to 80% survival in mice treated with vehicle solution. Thirty day survival of mice exposed to 810 cGy and treated with 1 administration of 0.3 mg/kg or 1 mg/kg of BBT-015 was 95% and 100%, respectively, as compared to 50% survival in mice treated with vehicle solution. CBC analysis indicated that BBT-015 administration was associated with accelerated recovery of neutrophils, red blood cells and platelets compared to vehicle-treated mice, i.e., BBT-015-treated mice had higher numbers of neutrophils, red blood cells and platelets on days 20-30 post-irradiation compared to vehicle-treated mice.

Figure 8:
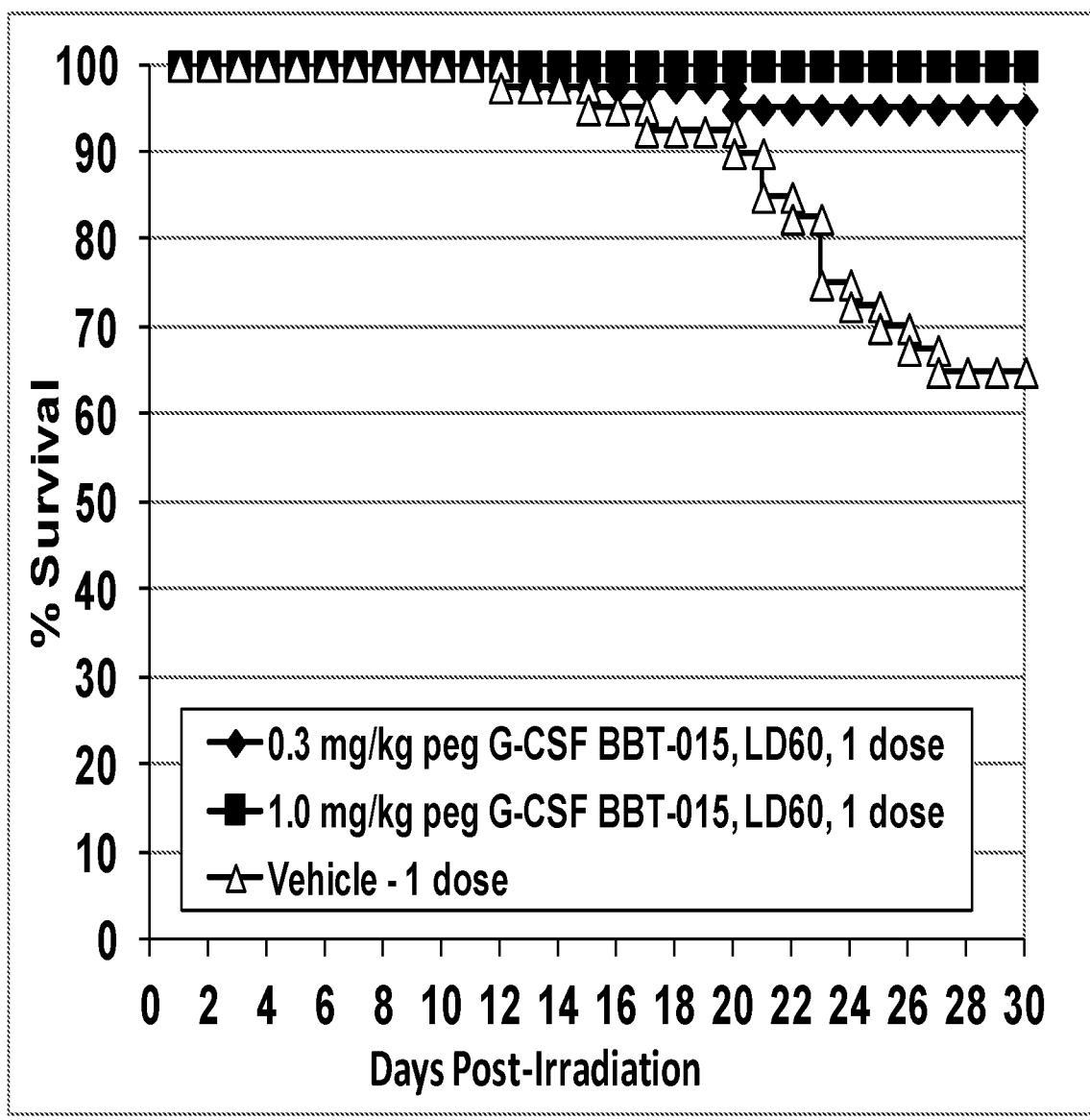
FIG. 8. Kaplan-Meier Survival Curves; 786cGy dose groups only. Mice were exposed to 786 cGy and injected subcutaneously with either 0.3 mg/kg or 1.0 mg/kg peg-G-CSF analog BBT-015 on d1 after irradiation (filled symbols). Control mice were similarly injected but with vehicle (open symbols). Mice were not treated with antibiotics. N=20 mice per group.
Figure 9:
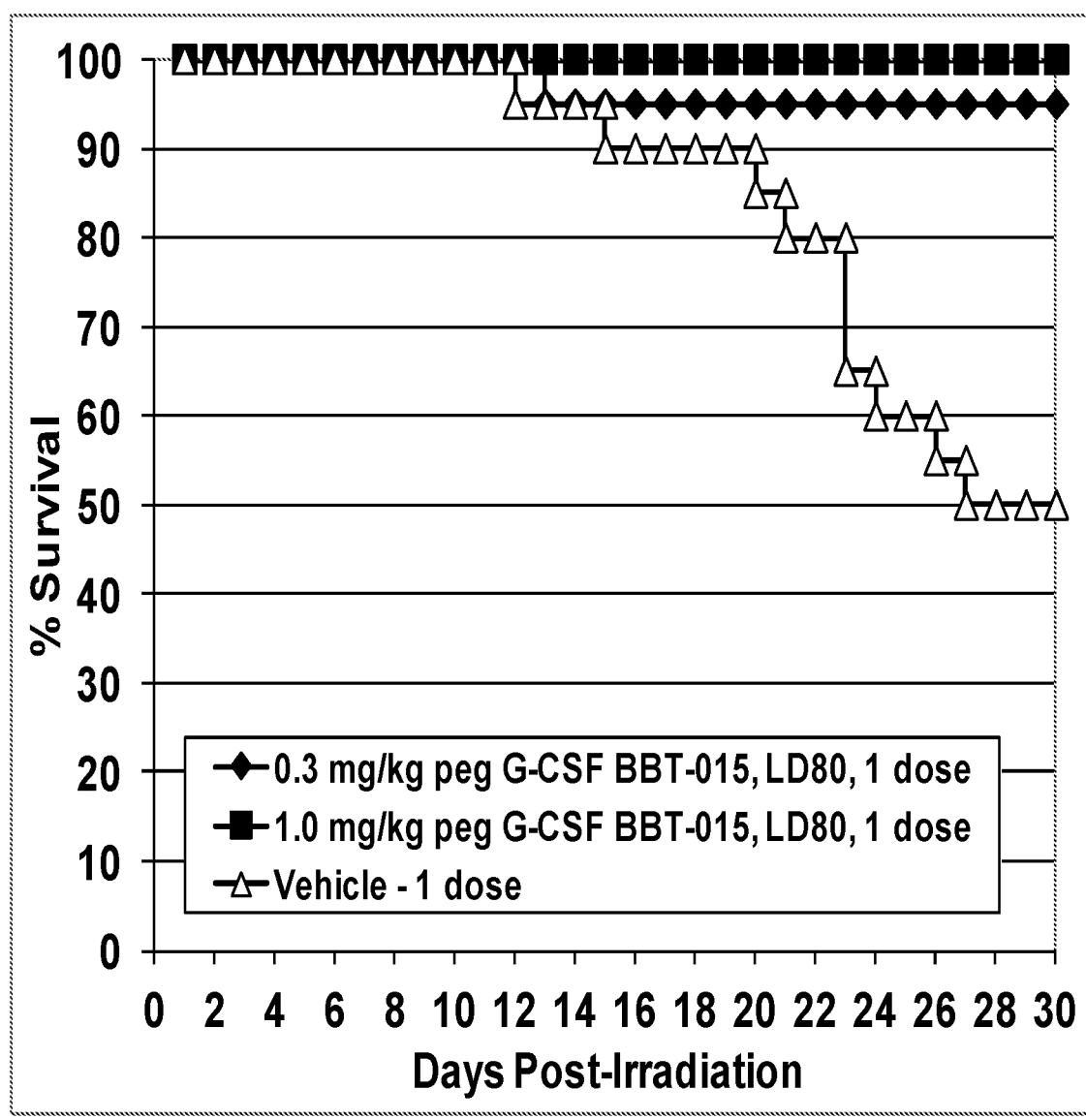
FIG. 9. Kaplan-Meier Survival Curves; 810 cGy dose groups only. Mice were exposed to 810 cGy and injected subcutaneously with either 0.3 mg/kg or 1.0 mg/kg peg-G-CSF analog BBT-015 on d1 after irradiation (filled symbols). Control mice were similarly injected but with vehicle (open symbols). Mice were not treated with antibiotics. N=20 mice per group.
Figure 10:
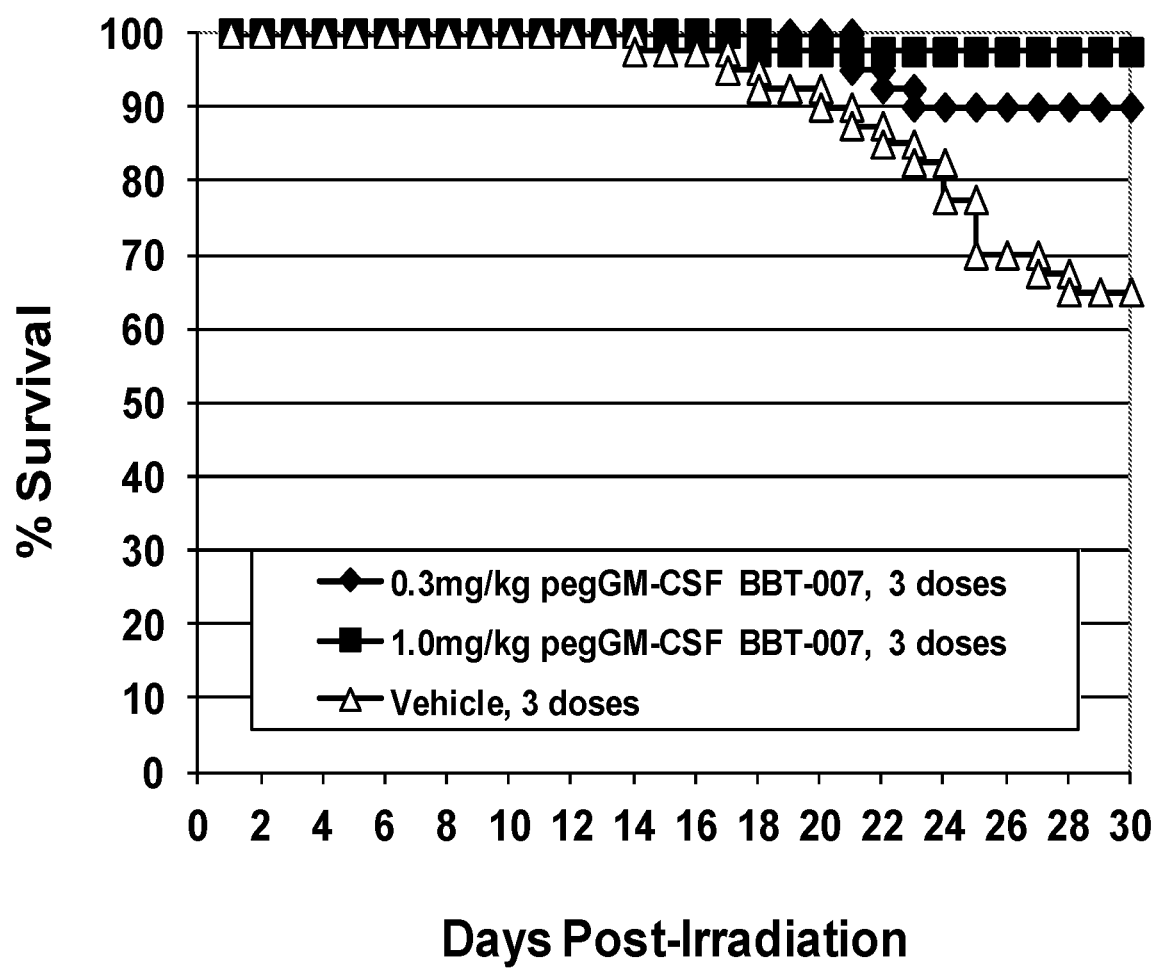
FIG. 10. Kaplan-Meier Survival Curves; pooled data from both radiation dose groups (792+806 cGy). Mice were exposed to 792 cGy or 806 cGy and injected subcutaneously with either 0.3 mg/kg or 1.0 mg/kg PEG-GM-CSF analog BBT-007 on days 1, 3 and 5 after irradiation (filled symbols). Control mice were similarly injected but with vehicle (open symbols). Thirty-day survival was significantly increased in both groups of mice treated with 0.3 mg/kg or 1.0 mg/kg of PEG-GM-CSF analog BBT-007. N=40 mice per group.

Thirty Day Survival (Table 6 and FIGS. 8, 9 and 10)

Pooled Data from Both Radiation Dose Groups Combined (786+810cGy):

Thirty day survival of mice exposed to 786 or 810 cGy irradiation and treated with 1 dose of 0.3 mg/kg of PEG-G-CSF analog BBT-015 on day 1 after irradiation was significant increased (95% survival) compared to vehicle-treated mice (65% survival, p=0.001). Thirty day survival of mice exposed to 786 or 810 cGy and treated with 1 dose of 1.0 mg/kg of PEG-G-CSF analog BBT-015 on day 1 after irradiation was significant increased (100% survival) compared to vehicle-treated mice (65% survival, p<0.001).

CBC Analyses: Days −3, 10, 20, 25, and 30 Days Post-Exposure (Table 7).

Peripheral blood was obtained from the mice on days −3, 10, 20, 25, and 30, and was analyzed for Complete Blood Count (CBC) by HEMAVET. Blood from age-matched non-irradiated mice was likewise analyzed. Many CBC parameters were significantly increased in mice treated with PEG-G-CSF analog BBT-015 compared to controls, as described below and shown in Table 7.

There were significant overall treatment group differences in the white blood cell count (p=0.006), neutrophils (p<0.001), percent neutrophils (p<0.001, data not shown), percent lymphocytes (p<0.001, data not shown), red blood cell counts (p<0.001), hemoglobin (p<0.001), hematocrit (p<0.001), and platelet count (p<0.001). The mean lymphocyte count was not different between the control group and either 0.3 mg/kg or 1.0 mg/kg peg-G-CSF analog BBT-015 groups (p=0.808).

The mean white blood cell count was significantly higher for the Test Article, 1.0 mg/kg compared to the Control article (p=0.002). The mean neutrophil count for the Control Article was significantly lower compared to Test Article, 0.3 mg/kg and Test Article, 1.0 mg/kg (p=0.002, p<0.001, respectively). The mean red blood cell count for the Control Article was significantly lower compared to Test Article, 0.3 mg/kg and Test Article, 1.0 mg/kg (p<0.001 for both). The mean hemoglobin for the Control Article was significantly lower compared to Test Article, 0.3 mg/kg and Test Article,

TABLE 6

Thirty Day Survival, Mean Survival Time (MST), and Overall Survival Time

| Group Description | Rad Dose in cGy | No. of Survivors/ Total | 30 day Survival (%) | | MST of Decedents (days) | | p value vs. vehicle | | |
|---|---|---|---|---|---|---|---|---|---|
| | | | | | | | 30 d Survival | MST | Overall Survival Time |
| PEG-G-CSF analog BBT-015 (0.3 mg/kg on day 1) | 786 810 | 19/20 19/20 | 95 95 | 95 | 20 13 | 16.5 | 0.001 | * | ** |
| PEG-G-CSF analog BBT-015 (1.0 mg/kg on d 1) | 786 810 | 20/20 20/20 | 100 100 | 100 | N/A N/A | N/A | <0.001 | * | ** |
| Sodium acetate/NaCl control (day 1) | 786 810 | 16/20 10/20 | 80 50 | 65 | 21.3 21.4 | 21.4 | | | |

*Due to the sparseness of data in the 0.3 mg/kg groups and 100% survival in the 1.0 mg/kg groups, a comparison of mean survival times of decedents was not possible.
**An accurate comparison of the overall survival between treatment groups was not possible due to 100% survival in the 1.0 mg/kg treatment group.

Mean Survival Time (MST) of Decedent Mice; Pooled Data from Both Radiation Dose Groups Combined (786+810 cGy, Table 6):

MST of decedent mice exposed to 786 or 810 cGy irradiation and treated with 1 dose of 0.3 mg/kg PEG-G-CSF analog BBT-015 on day 1 after irradiation was 16.5 days, whereas, for mice similarly irradiated and treated with vehicle, was 21.4 days. MST of decedent mice exposed to 786 or 810 cGy irradiation and treated with 1 dose of 1.0 mg/kg PEG-G-CSF analog BBT-015 on day 1 after irradiation was not calculated due to no decedent mice in that treatment group.

Overall Survival Time; Pooled Data from Both Radiation Dose Groups Combined (786+810 cGy, Table 1)

An accurate comparison of the overall survival between treatment groups was not possible due to 100% survival in the 1.0 mg/kg treatment group.

1.0 mg/kg (p<0.001 for both). The mean platelet count for the Control Article was significantly lower compared to Test Article, 0.3 mg/kg and Test Article, 1.0 mg/kg (p<0.001). The mean hematocrit for the Control Article was lower compared to Test Article, 0.3 mg/kg and Test Article, 1.0 mg/kg. Bleed day was significant for every complete blood count variable (p<0.01 for every variable).

Similar studies can be performed using different doses, dosing regimens and routes of administration of BBT-015. Examples provided above teach how to determine whether 1 to 9 administrations of the protein are effective at improving survival and accelerating blood cell recovery (hemapoeitic recovery) following different radiation doses. Timing of the first administration of the protein also can be altered (e.g., first dosing can begin at various times from 1-30 days following radiation exposure, or prior to 24 hours post-radiation exposure).

The Complete Blood Cell (CBC) parameters for this example are shown in Table 7. CBC were performed at baseline (day −3) and on study days 10, 20, 25, and 30 from randomly selected male and female mice exposed to 786 or 810cGy ionizing radiation and treated once with 0.3 or 1.0 mg/kg peg-G-CSF analog BBT-015 on Day 1. Data are presented as mean±SD. Four non-irradiated control mice were analyzed on each day as well. Abbreviations used are WBC (white blood cells; thousands per microliter); NE (neutrophils; thousands per microliter); Ly (lymphocytes; thousands per microliter); RBC (red blood cells; millions per microliter); Hb (hemoglobin, g/dL); Hct (hematocrit; percent); Plt (platelet, thousand per microliter). Control-NI are non-irradiated control mice.

expected to be an LD50/30 dose based upon prior studies, and 806 cGy, which was expected to be an LD70/30 dose based upon prior studies. Groups of C57BL/6 mice (N=10 males and 10 females per group) received one of six treatments in a randomized vehicle-controlled study (Table 8). Endpoints for this study was 30 day overall survival, mean survival time and CBC analyses. The radiation dose was delivered as a single uniform total body dose of gamma radiation from a 137Cs radiation source at an exposure rate of 65-69 cGy/minute+/−2.5 cGy. BBT-007 or vehicle solution (10 mM sodium acetate, pH 4.8, 140 mM NaCl) was subcutaneously administered three times (on days 1, 3 and 5) to 10-12 week old mice beginning 24+4/−0 hours after irradiation treatment. Mice were weighed during the accli-

CBC PARAMETERS TABLE 7

| | | WBC | | NE | | Ly | | RBC | | Hb | | Hct | | Plt | |
|---|---|---|---|---|---|---|---|---|---|---|---|---|---|---|---|
| Group | Day | mean | SD | mean | SD | mean | SD | mean | SD | mean | SD | mean | SD | mean | SD |
| Control-NI | −4 | 16.64 | 5.55 | 2.94 | 1.24 | 12.63 | 3.81 | 10.36 | 2.06 | 15.0 | 3.1 | 53.4 | 10.8 | 827 | 168 |
| group 1 | 10 | 0.26 | 0.03 | 0.03 | 0.00 | 0.22 | 0.01 | 6.31 | 1.00 | 8.2 | 1.4 | 30.8 | 5.2 | 78 | 19 |
| group 2 | 10 | 0.34 | 0.13 | 0.11 | 0.07 | 0.24 | 0.05 | 6.04 | 0.34 | 8.1 | 0.4 | 29.8 | 1.7 | 90 | 35 |
| group 3 | 10 | 0.22 | 0.03 | <0.22 | | <0.22 | | 5.83 | 0.72 | 7.7 | 1.0 | 28.4 | 3.3 | 47 | 7 |
| group 4 | 10 | 0.32 | 0.11 | 0.08 | 0.03 | 0.27 | 0.07 | 6.29 | 0.54 | 8.4 | 0.8 | 30.8 | 3.0 | 76 | 15 |
| group 5 | 10 | 0.28 | 0.06 | 0.08 | 0.04 | 0.22 | 0.01 | 5.71 | 0.80 | 7.4 | 1.2 | 27.6 | 4.4 | 62 | 29 |
| group 6 | 10 | 0.32 | 0.17 | 0.08 | 0.08 | 0.26 | 0.11 | 5.58 | 1.32 | 7.3 | 1.9 | 26.8 | 6.5 | 48 | 12 |
| Control-NI | 10 | 13.31 | 5.43 | 2.37 | 1.03 | 10.44 | 4.28 | 12.41 | 3.37 | 13.3 | 3.5 | 64.2 | 17.6 | 947 | 149 |
| group 1 | 20 | 2.83 | 2.08 | 1.64 | 1.70 | 1.01 | 0.52 | 7.39 | 1.32 | 11.6 | 1.4 | 44.2 | 6.1 | 550 | 258 |
| group 2 | 20 | 4.10 | 0.48 | 2.72 | 0.35 | 1.12 | 0.23 | 8.91 | 0.35 | 13.5 | 0.4 | 50.4 | 1.7 | 627 | 104 |
| group 3 | 20 | 4.79 | 7.29 | 0.67 | 1.01 | 3.81 | 5.81 | 2.74 | 0.91 | 3.8 | 1.4 | 13.4 | 5.1 | 122 | 68 |
| group 4 | 20 | 3.79 | 1.32 | 1.75 | 0.36 | 1.85 | 1.66 | 7.90 | 1.34 | 11.8 | 1.1 | 45.5 | 5.9 | 519 | 143 |
| group 5 | 20 | 3.15 | 1.37 | 1.36 | 0.49 | 1.54 | 0.85 | 7.70 | 1.28 | 12.1 | 1.5 | 44.8 | 5.4 | 574 | 19 |
| group 6 | 20 | 3.96 | 6.53 | 1.31 | 1.92 | 3.35 | 4.55 | 2.00 | 0.98 | 2.4 | 0.9 | 9.9 | 6.2 | 73 | 54 |
| Control-NI | 20 | 20.27 | 5.59 | 4.10 | 1.15 | 14.68 | 4.52 | 10.98 | 0.31 | 15.9 | 0.4 | 58.1 | 1.6 | 762 | 126 |
| group 1 | 25 | 4.22 | 0.89 | 2.29 | 0.41 | 1.62 | 0.48 | 10.19 | 2.10 | 13.2 | 0.3 | 56.6 | 11.0 | 505 | 127 |
| group 2 | 25 | 4.36 | 1.11 | 2.88 | 1.07 | 1.31 | 0.14 | 8.64 | 0.92 | 12.6 | 2.0 | 47.5 | 5.8 | 602 | 69 |
| group 3 | 25 | 3.26 | 2.25 | 0.80 | 0.31 | 2.27 | 1.95 | 4.32 | 1.18 | 6.2 | 2.3 | 28.0 | 8.7 | 311 | 44 |
| group 4 | 25 | 3.91 | 1.42 | 2.02 | 0.92 | 1.54 | 0.52 | 8.17 | 2.29 | 11.6 | 3.8 | 44.5 | 13.1 | 439 | 119 |
| group 5 | 25 | 4.30 | 1.05 | 2.59 | 0.59 | 1.43 | 0.35 | 8.81 | 0.60 | 12.8 | 0.5 | 48.3 | 2.4 | 623 | 49 |
| group 6 | 25 | 1.22 | 0.56 | 0.14 | 0.06 | 1.02 | 0.50 | 2.36 | 0.56 | 3.4 | 1.0 | 13.9 | 5.2 | 143 | 18 |
| Control-NI | 25 | 17.31 | 7.06 | 3.34 | 1.80 | 13.01 | 5.18 | 9.76 | 2.45 | 14.1 | 4.0 | 50.0 | 13.2 | 785 | 234 |
| group 1 | 30 | 4.19 | 1.34 | 1.98 | 1.24 | 1.92 | 0.33 | 9.11 | 1.72 | 13.0 | 2.9 | 49.9 | 10.4 | 600 | 161 |
| group 2 | 30 | 6.42 | 1.65 | 2.46 | 0.78 | 3.31 | 0.71 | 8.50 | 1.38 | 12.2 | 2.2 | 46.7 | 8.0 | 570 | 105 |
| group 3 | 30 | 5.54 | 5.40 | 2.78 | 3.13 | 1.97 | 1.32 | 7.89 | 0.93 | 11.7 | 2.7 | 47.5 | 10.0 | 598 | 82 |
| group 4 | 30 | 3.91 | 1.91 | 1.97 | 1.30 | 1.65 | 0.49 | 8.69 | 2.35 | 11.9 | 4.5 | 48.3 | 13.3 | 507 | 178 |
| group 5 | 30 | 5.00 | 2.36 | 2.63 | 1.42 | 2.04 | 0.85 | 9.63 | 0.86 | 14.2 | 0.8 | 54.4 | 3.3 | 674 | 151 |
| group 6 | 30 | 2.61 | 1.40 | 0.93 | 0.63 | 1.43 | 0.71 | 5.73 | 3.40 | 9.1 | 5.4 | 36.6 | 20.5 | 383 | 326 |
| Control-NI | 30 | 17.75 | 2.21 | 3.25 | 0.80 | 13.22 | 2.02 | 10.40 | 1.73 | 14.3 | 2.5 | 54.6 | 10.4 | 704 | 238 |

Example 4. Three Every Other Day Administrations of PEG-GM-CSF Analog BBT-007 Improves 30 Day Survival of Lethally Irradiated Mice This example demonstrates that three every other day subcutaneous administrations of BBT-007 administered beginning 24+4/−0 hours following a lethal dose of radiation is capable of significantly improving 30 day survival of mice compared to vehicle solution. The data also indicate that three every other day administrations of BBT-007 administered beginning 24 hours following a lethal dose of radiation is capable of significantly increasing numbers of neutrophils, red blood cells, lymphocytes, white blood cells and platelets in irradiated mice compared to vehicle solution, indicating an acceleration of hematopoietic recovery for these cell types.

The ability of three every other day administrations of PEG-GM-CSF analog BBT-007 to increase 30 day survival in mice after radiation exposure was tested using two different BBT-007 doses (0.3 mg/kg and 1.0 mg/kg) and at two different doses of radiation, 792 cGy, which was mation period and an average weight of all females and all males were calculated separately. All females were dosed based on the average weight of the females, and all males dosed based on the average weight of the males. The volume of BBT-007 was adjusted to deliver a dose of approximately 6.0 μg (about 0.3 mg/kg) or 20.0 μg (about 1 mg/kg) to each mouse, slightly less than 100 μL to the females, and slightly more than 100 μL to the males. These BBT-007 doses in mice (0.3 and 1.0 mg/kg) correspond to equivalent human doses of about 0.024 and 0.081 mg/kg, respectively, due to faster clearance of protein therapeutics in mice compared to humans. An equivalent volume of vehicle solution was administered to those mice in the control groups. Weights were not taken again during the study; mice were dosed based on the weight taken during the acclimation period.

Figure 11:
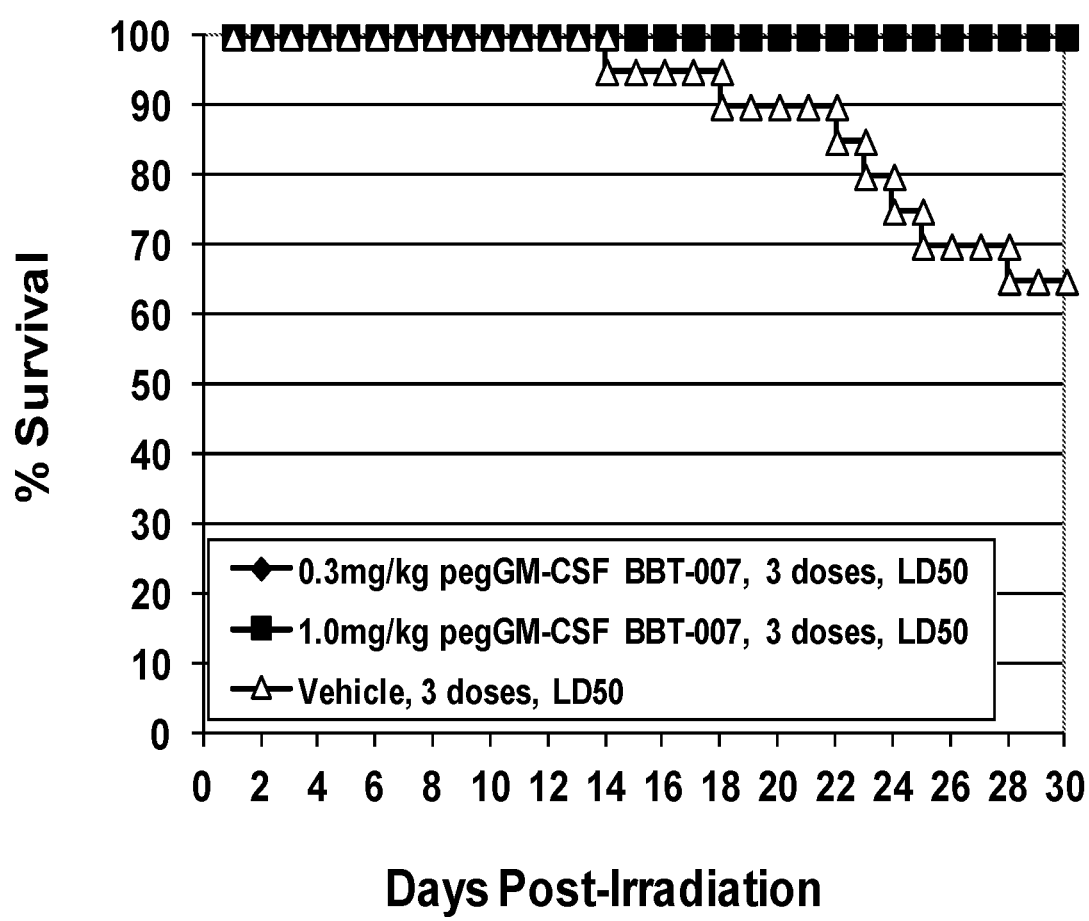
FIG. 11. Kaplan-Meier Survival Curves; 792 cGy dose groups only. Mice were exposed to 792 cGy and injected subcutaneously with either 0.3 mg/kg or 1.0 mg/kg peg-GM-CSF analog BBT-007 on days 1, 3 and 5 after irradiation (filled symbols). Control mice were similarly injected but with vehicle (open symbols). N=20 mice per group.
Figure 12:
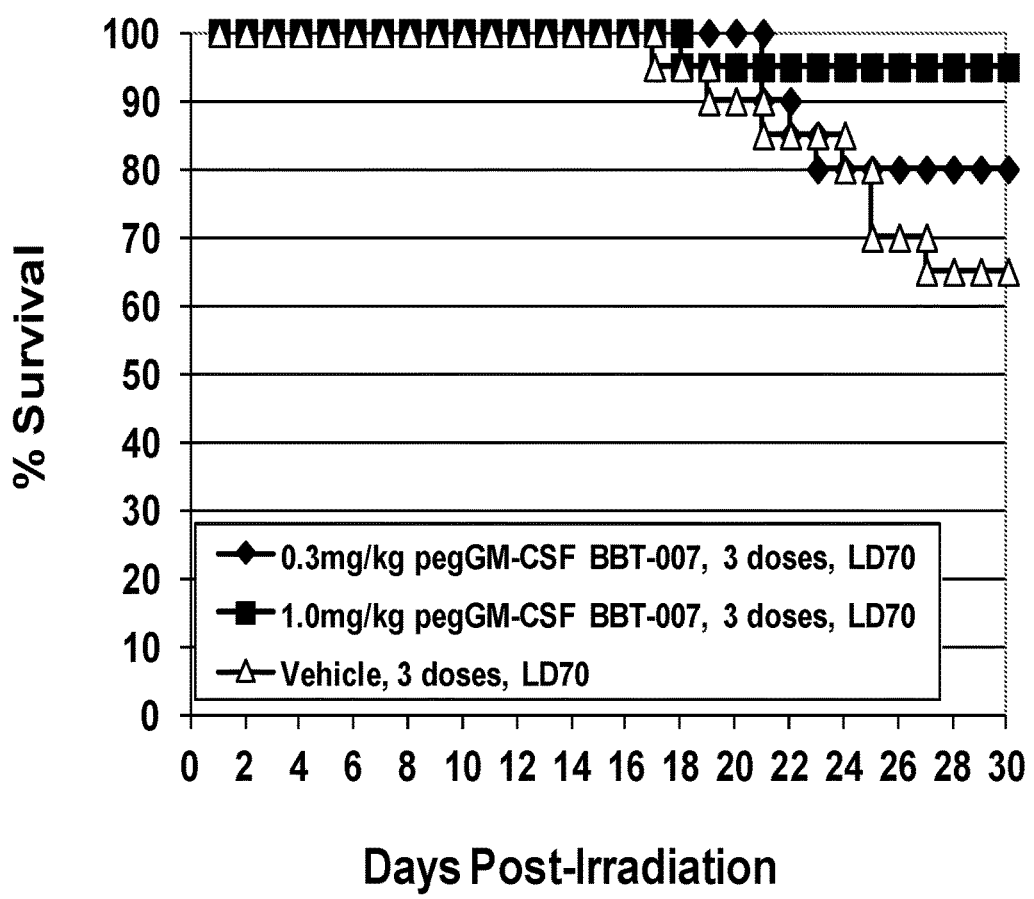
FIG. 12. Kaplan-Meier Survival Curves; 806 cGy dose groups only. Mice were exposed to 806 cGy and injected subcutaneously with either 0.3 mg/kg or 1.0 mg/kg peg-GM-CSF analog BBT-007 on days 1, 3 and 5 after irradiation (filled symbols). Control mice were similarly injected but with vehicle (open symbols). N=20 mice per group.

As shown in Table 8 and FIGS. 11, 12 and 13, thirty day survival of mice exposed to 792 cGy and treated with three every other day administrations of 0.3 mg/kg or 1 mg/kg of BBT-007 was 100% and 100%, respectively, as compared to 65% survival in mice treated with vehicle solution. Thirty day survival of mice exposed to 806 cGy and treated with three every other day administration of 0.3 mg/kg or 1 mg/kg of BBT-007 was 80% and 95%, respectively, as compared to 65% survival in mice treated with vehicle solution. Whether or not a mouse was going to live at least 30 days was analyzed from pooled data from the two radiation doses with an exact logistic model using treatment group, radiation dose, and gender as predictors. After controlling for gender and radiation dose BBT-007 at a dose of 1 mg/kg was a protective factor compared to the Vehicle ($p<0.001$, odds ratio=0.05) and BBT-007 at a dose of 0.3 mg/kg was a protective factor compared to Vehicle ($p=0.006$, odds ratio=0.20).

TABLE 8

Three every other day administrations of PEG-GM-CSF analog BBT-007 improve 30 day survival of irradiated mice.

| Group | Treatment | Drug Dose | Radiation Dose | Numbers and Sex of Animals | Number of survivors on Day 30 (%) |
|---|---|---|---|---|---|
| 1 | BBT-007 | 0.3 mg/kg | 792 cGy | 10F, 10M | 20/20 (100%) |
| 2 | BBT-007 | 1.0 mg/kg | 792 cGy | 10F, 10M | 20/20 (100%) |
| 3 | Vehicle control | N/A | 792 cGy | 10F, 10M | 13/20 (65%) |
| 4 | BBT-007 | 0.3 mg/kg | 806 cGy | 10F, 10M | 16/20 (80%) |
| 5 | BBT-007 | 1.0 mg/kg | 806 cGy | 10F, 10M | 19/20 (95%) |
| 6 | Vehicle control | N/A | 806 cGy | 10F, 10M | 13/20 (65%) |

CBCs with differential and peripheral smears were performed as described in the other Examples. CBC data are presented in Table 9. There was a significant bleed day by treatment group interaction for white blood cell counts ($p=0.002$), neutrophils ($p=0.050$), lymphocytes ($p=0.078$), red blood cell counts ($p=0.005$), hemoglobin ($p=0.004$), hematocrit ($p=0.004$), platelet count ($p=0.098$), and mean corpuscular volume ($p=0.079$). Within bleed day 20, the vehicle group had a significantly lower mean white blood cell count when compared to BBT-007, 0.3 mg/kg and BBT-007, 1 mg/kg (both $p<0.001$). Within bleed day 20, the vehicle group had a significantly lower mean neutrophil count when compared to BBT-007, 0.3 mg/kg and BBT-007, 1 mg/kg (both $p<0.001$). Within bleed day 25, the vehicle group had a significantly lower mean neutrophil count when compared to BBT-007, 0.3 mg/kg ($p=0.050$) and a marginally lower mean neutrophil count when compared to muBBT-007, 1 mg/kg ($p=0.073$). Within bleed day 20, the vehicle group had a significantly lower mean lymphocyte count when compared to BBT-007, 0.3 mg/kg ($p<0.001$) and BBT-007, 1 mg/kg ($p=0.002$). Within bleed days 20 and 25, the vehicle group had a significantly lower mean red blood cell count when compared to BBT-007, 0.3 mg/kg and BBT-007, 1 mg/kg (all $p<0.001$). Within bleed days 20 and 25, the vehicle group had a significantly lower mean hemoglobin count when compared to BBT-007, 0.3 mg/kg and BBT-007, 1 mg/kg (all $p<0.001$). Within bleed days 20 and 25, the vehicle group had a significantly lower mean hematocrit count when compared to BBT-007, 0.3 mg/kg and BBT-007, 1 mg/kg (all $p<0.001$). Within bleed day 20, the vehicle group had a significantly lower mean platelet count when compared to BBT-007, 0.3 mg/kg and BBT-007, 1 mg/kg (both $p<0.001$). Within bleed day 25, the vehicle group had a significantly lower mean platelet count when compared to BBT-007, 0.3 mg/kg ($p=0.009$) and BBT-007, 1 mg/kg ($p=0.003$).

In summary, there were no significant differences at days 10 or 30 for any of the variables between the BBT-007 and vehicle groups. There were significant differences between the vehicle group and both BBT-007 treatment groups and for all variables at day 20. At day 25, both BBT-007 treatment groups had significantly higher red blood cell counts, hemoglobin, hemocrit, and platelets than the vehicle group. There were borderline differences in neutrophil numbers between the two BBT-007 treatment groups and the vehicle group at day 25.

Similar studies can be performed using different doses, dosing regimens and routes of administration of BBT-007. Examples provided above teach how to determine whether 1 to 9 administrations of the protein are effective at improving survival and accelerating blood cell recovery (hemapoeitic recovery) following different radiation doses. Timing of the first administration of the protein also can be altered (e.g., first dosing can begin at various times from 1-30 days following radiation exposure, or prior to 24 hours post-radiation exposure).

The Complete Blood Cell (CBC) parameters for this example are shown in Table 9. CBC were performed at baseline (day −3) and on study days 10, 20, 25, and 30 from randomly selected male and female mice exposed to 792 or 806cGy ionizing radiation and treated with 0.3 or 1.0 mg/kg peg-GM-CSF analog BBT-007 on Days 1, 3 and 5. Data are presented as mean±SD. Four non-irradiated control mice were analyzed on each day as well. Abbreviations used are WBC (white blood cells; thousands per microliter); NE (neutrophils; thousands per microliter); Ly (lymphocytes; thousands per microliter); RBC (red blood cells; millions per microliter); Hb (hemoglobin, g/dL); Hct (hematocrit; percent); Plt (platelet, thousand per microliter). Control-NI are non-irradiated control mice.

CBC PARAMETERS TABLE 9

| | | WBC | | NE | | Ly | | RBC | | Hb | | Hct | | Plt | |
|---|---|---|---|---|---|---|---|---|---|---|---|---|---|---|---|
| Group | Day | mean | SD | mean | SD | mean | SD | mean | SD | mean | SD | mean | SD | mean | SD |
| Control-NI | −3 | 13.37 | 3.48 | 2.14 | 0.61 | 10.42 | 3.03 | 10.98 | 0.68 | 15.52 | 0.84 | 58.33 | 3.78 | 934 | 218 |
| group 1 | 10 | 0.26 | 0.03 | 0.07 | 0.02 | 0.18 | 0.03 | 7.21 | 0.33 | 9.60 | 0.44 | 33.70 | 1.49 | 113 | 34 |
| group 2 | 10 | 0.34 | 0.07 | 0.08 | 0.02 | 0.22 | 0.07 | 6.65 | 0.48 | 8.83 | 1.01 | 31.03 | 2.31 | 110 | 29 |
| group 3 | 10 | 0.26 | 0.03 | 0.04 | 0.00 | 0.23 | 0.00 | 5.88 | 0.65 | 7.75 | 0.49 | 27.18 | 2.68 | 74 | 28 |
| group 4 | 10 | 0.29 | 0.05 | 0.06 | 0.01 | 0.25 | 0.04 | 6.20 | 0.89 | 8.25 | 1.29 | 28.75 | 4.47 | 93 | 36 |
| group 5 | 10 | 0.29 | 0.04 | 0.07 | 0.01 | 0.20 | 0.02 | 6.97 | 0.40 | 9.28 | 0.45 | 32.13 | 2.09 | 103 | 11 |
| group 6 | 10 | 0.23 | 0.03 | <0.23 | | <0.23 | | 5.59 | 0.84 | 7.30 | 1.10 | 25.88 | 3.62 | 73 | 28 |
| Control-NI | 10 | 13.84 | 2.53 | 4.63 | 4.85 | 8.14 | 3.22 | 11.08 | 0.47 | 15.75 | 0.64 | 54.80 | 2.15 | 1034 | 132 |
| group 1 | 20 | 5.02 | 3.75 | 0.98 | 1.15 | 3.79 | 3.74 | 5.34 | 2.44 | 8.25 | 4.21 | 29.45 | 14.42 | 362 | 242 |
| group 2 | 20 | 9.51 | 6.14 | 0.87 | 0.42 | 8.24 | 5.56 | 4.81 | 0.13 | 7.88 | 0.75 | 28.00 | 1.81 | 396 | 59 |
| group 3 | 20 | 1.85 | 2.32 | 0.30 | 0.25 | 1.45 | 1.98 | 2.50 | 1.30 | 3.53 | 2.28 | 12.03 | 8.45 | 133 | 109 |
| group 4 | 20 | 7.41 | 6.13 | 0.92 | 0.61 | 6.06 | 5.23 | 4.80 | 2.84 | 7.68 | 4.77 | 27.70 | 17.49 | 395 | 231 |

CBC PARAMETERS TABLE 9-continued

| Group | Day | WBC mean | WBC SD | NE mean | NE SD | Ly mean | Ly SD | RBC mean | RBC SD | Hb mean | Hb SD | Hct mean | Hct SD | Plt mean | Plt SD |
|---|---|---|---|---|---|---|---|---|---|---|---|---|---|---|---|
| group 5 | 20 | 2.59 | 2.16 | 0.73 | 0.52 | 1.64 | 1.53 | 4.91 | 3.72 | 9.53 | 6.74 | 28.23 | 23.49 | 350 | 292 |
| group 6 | 20 | 0.49 | 0.20 | 0.11 | 0.06 | 0.42 | 0.11 | 1.64 | 0.59 | 1.98 | 0.81 | 6.93 | 2.54 | 67 | 20 |
| Control-NI | 20 | 17.52 | 7.63 | 2.94 | 1.56 | 13.54 | 5.64 | 9.15 | 3.33 | 13.18 | 5.12 | 45.35 | 17.06 | 811 | 392 |
| group 1 | 25 | 11.02 | 8.66 | 2.33 | 0.42 | 7.91 | 8.28 | 7.48 | 1.46 | 12.08 | 1.48 | 44.95 | 4.58 | 725 | 161 |
| group 2 | 25 | 3.96 | 1.22 | 2.01 | 0.86 | 1.57 | 0.47 | 8.02 | 0.80 | 12.40 | 0.76 | 46.18 | 2.81 | 888 | 295 |
| group 3 | 25 | 8.00 | 7.59 | 1.89 | 1.18 | 5.38 | 5.82 | 4.66 | 2.62 | 7.28 | 4.61 | 27.95 | 16.59 | 504 | 175 |
| group 4 | 25 | 6.25 | 5.08 | 1.78 | 0.59 | 4.04 | 5.14 | 8.04 | 1.93 | 12.08 | 2.46 | 44.00 | 7.81 | 615 | 154 |
| group 5 | 25 | 4.33 | 0.20 | 1.95 | 0.63 | 1.95 | 0.42 | 8.54 | 0.88 | 12.75 | 1.54 | 44.95 | 5.31 | 608 | 36 |
| group 6 | 25 | 4.66 | 3.25 | 0.68 | 0.39 | 3.67 | 2.76 | 4.15 | 2.51 | 6.75 | 4.52 | 26.38 | 17.69 | 406 | 218 |
| Control-NI | 25 | 21.48 | 3.54 | 4.36 | 0.97 | 15.42 | 2.71 | 10.93 | 0.72 | 15.55 | 1.10 | 52.85 | 2.92 | 952 | 191 |
| group 1 | 30 | 8.32 | 4.43 | 4.41 | 2.00 | 3.24 | 1.98 | 8.78 | 0.97 | 13.65 | 1.11 | 46.93 | 4.59 | 822 | 146 |
| group 2 | 30 | 6.74 | 1.27 | 4.14 | 0.82 | 2.61 | 0.15 | 8.53 | 0.63 | 13.05 | 0.93 | 47.38 | 2.66 | 732 | 231 |
| group 3 | 30 | 5.44 | 1.12 | 2.79 | 1.05 | 2.19 | 0.42 | 8.21 | 0.85 | 12.88 | 1.35 | 47.13 | 3.10 | 810 | 264 |
| group 4 | 30 | 11.31 | 9.31 | 2.64 | 1.38 | 8.03 | 9.77 | 8.13 | 2.05 | 12.40 | 2.74 | 45.67 | 6.75 | 753 | 97 |
| group 5 | 30 | 6.63 | 2.64 | 2.75 | 2.61 | 3.40 | 1.79 | 7.83 | 1.98 | 11.20 | 0.14 | 46.83 | 4.65 | 961 | 82 |
| group 6 | 30 | 10.18 | 9.10 | 7.54 | 8.45 | 1.88 | 0.40 | 8.82 | 0.82 | 13.55 | 0.38 | 49.05 | 2.22 | 776 | 177 |
| Control-NI | 30 | 18.82 | 5.48 | 3.45 | 1.11 | 14.38 | 4.26 | 10.40 | 0.55 | 15.20 | 0.96 | 50.93 | 3.30 | 1024 | 188 |

Example 5. Experiment to Determine Whether Three Every Other Day Administrations of PEG-IL-11 Analog BBT-059 Improves 30 Day Survival of Lethally Irradiated Mice The ability of PEG-IL-11 analog BBT-059 to increase 30 day survival in mice after radiation exposure can be tested using experimental protocols described above in the other Examples. For example, the ability of three every other day subcutaneous administrations of PEG-IL-11 analog BBT-059 to increase survival and hematopoietic recovery in irradiated mice can be tested using two different BBT-059 doses (0.3 mg/kg and 1.0 mg/kg) and at two different doses of radiation, 792 cGy, which is expected to be an LD50/30 dose based upon prior studies, and 806 cGy, which is expected to be an LD70/30 dose based upon prior studies. Groups of C57BL/6 mice (N=10 males and 10 females per group) can receive one of six treatments in a randomized vehicle-controlled study (Table 10). Endpoints of this study can be 30 day overall survival, mean survival time and CBC analyses. The radiation doses can be delivered as a single uniform total body dose of gamma radiation from a 137Cs radiation source at an exposure rate of 65-69 cGy/minute+/− 2.5 cGy. BBT-059 or vehicle solution (20 mM Tris, pH 7.5, 200 mM NaCl, 10% glycerol, 0.05% Tween-20) can be subcutaneously administered three times (on days 1, 3 and 5) to 10-12 week old mice beginning 24+4/−0 hours after irradiation treatment. Mice can be weighed during the acclimation period and an average weight of all females and all males can be calculated separately. All females can be dosed based on the average weight of the females, and all males can be dosed based on the average weight of the males. The volume of BBT-059 can be adjusted to deliver a dose of approximately 6.0 μg (about 0.3 mg/kg) or 20.0 μg (about 1 mg/kg) to each mouse, slightly less than 100 μL to the females, and slightly more than 100 μL to the males. These BBT-059 doses in mice (0.3 mg/kg and 1.0 mg/kg) correspond to equivalent human doses of about 0.024 mg/kg and 0.081 mg/kg, respectively, due to faster clearance of protein therapeutics in mice compared to humans. An equivalent volume of vehicle solution can be administered to those mice in the control groups. Mice can be dosed based on the weight taken during the acclimation period. Survival and CBC data can be complied as described in the other examples. It is expected that both doses of BBT-059 will improve 30 day survival of mice exposed to these radiation doses compared to vehicle. It is also expected that BBT-059 will cause accelerated recovery of blood cell types such as platelets, neutrophils, white blood cells, red blood cells, and lymphocytes compared to vehicle solution, as evidenced by higher circulating levels of these cells on days 20 and possibly on days 25 and 30 in the BBT-059-treated mice compared to vehicle-treated mice. It is also possible that higher nadirs for these cell types on day 10 post-irradiation will be detected.

Similar studies can be performed using different doses, dosing regimens and routes of administration of BBT-059. The Examples provided above teach how to determine whether 1 to 9 administrations of the protein are effective at improving survival and accelerating hematopoietic blood cell recovery following different radiation doses. Timing of the first administration of the protein also can be altered (e.g., first dosing could begin at various times from 1-15 days following radiation exposure, or prior to 24 h post-radiation exposure) to identify the optimum time of administration.

TABLE 10

Outline of treatment groups for determining whether three every other day administrations of BBT-059 improve 30 day survival of irradiated mice.

| Group | Treatment | Drug Dose | Radiation Dose | Numbers and Sex of Animals |
|---|---|---|---|---|
| 1 | BBT-059 | 0.3 mg/kg | 792 cGy (LD50/30) | 10F, 10M |
| 2 | BBT-059 | 1.0 mg/kg | 792 cGy (LD50/30) | 10F, 10M |
| 3 | Vehicle | N/A | 792 cGy (LD50/30) | 10F, 10M |
| 4 | BBT-059 | 0.3 mg/kg | 806 cGy (LD70/30) | 10F, 10M |
| 5 | BBT-059 | 1.0 mg/kg | 806 cGy (LD70/30) | 10F, 10M |
| 6 | Vehicle | N/A | 806 cGy (LD70/30) | 10F, 10M |

Example 6. Determining how Long after Irradiation BBT-015, BBT-007 and BBT-059 can be Administered and Still Improve 30 Day Survival in Irradiated Mice How long after irradiation BBT-015, BBT-007 and BBT-059 (the "Test Articles") can be administered and still improve survival of lethally irradiated mice can be determined using the following protocol. Mice can be exposed to an LD50/30 radiation dose and randomized into test groups.

One group of control mice can receive from 1 to 9 subcutaneous injections of vehicle solution beginning 24+4/−0 h post irradiation. A second control group can receive 1 (or 3) subcutaneous injections of 1 mg/kg of the Test Articles beginning 24+4/−0 h post-irradiation. Additional test groups of mice can receive from 1 to 9 subcutaneous injections of 1 mg/kg of the Test Articles beginning at 48 h (day 2), 72 h (day 3), 96 h (day 4), 120 h (day 5), 144 h (day 6), 168 h (day 7), up through day 30, etc. post-irradiation. Survival of mice can be followed for 30 days. CBC analyses can be performed at different times post-irradiation, as described in the other Examples to determine whether the Test Articles accelerate recovery of white blood cells, neutrophils, red blood cells, lymphocytes, platelets, hemoglobin levels and hematocrits compared to vehicle-treated mice.

Similar studies can be performed using different doses and different dosing regimens as well as different routes of administration of the Test Articles.

Example 7. Determining Whether BBT-015, BBT-007 and BBT-059 Administration Improves Survival of Other Animal Species Such as Dogs and Monkeys Experiments similar to those described here can be used to determine whether BBT-015, BBT-007 and BBT-059 administration improves survival and accelerates hematopoietic recovery in other animal species such as dogs and monkeys following lethal irradiation. Radiation doses can be determined that correspond to LD50 to LD70 doses. Survival can be followed for 30-60 days following irradiation. Circulating half-lives of BBT-015 and BBT-007 are expected to be longer in dogs and monkeys compared to mice, so the dosing frequency and/or dose of the proteins can be adjusted to reflect the differences in clearance rates of the proteins between species, for example dosing once per week instead of every other day. The optimum dose and dosing regimen can be determined for each protein.

Example 8. Determining Whether Administration of BBT-015, BBT-007 and BBT-059 Prior to Radiation Exposure Will Improve 30 Day Survival of a Subject Whether administration of BBT-015, BBT-007 and BBT-015 (the "Test Articles") prior to irradiation will improve survival of lethally irradiated mice can be determined using the using the following protocol. Different groups of mice can be treated with one or more of the Test Articles or Control Article (vehicle) from about 7 days prior to radiation exposure to immediately prior to radiation exposure. Preferably the Test Article will be administered less than 48 hours prior to irradiation and most preferably less than 24 hours prior to irradiation. Survival of mice can be followed for 30 days. CBC analysis can be performed at different times post-irradiation, as described in the previous examples to determine whether the Test Articles accelerate recovery of white blood cells, neutrophils, red blood cells, lymphocytes, platelets, hemoglobin levels and hematocrits compared to vehicle-treated mice. Similar studies can be performed using different doses, dosing regimens, and routes of administration of the Test Articles.

All documents cited herein are incorporated herein by reference.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

REFERENCES

Abdel-Meguid, S. S., Shieh, h.-S., Smith W. W., Dayringer, H. E., Violand, B. N. and Bentle, L. A. (1987) Proc. Natl. Acad. Sci. USA 84: 6434-6437.

Arakawa, T. Prestrelski, S. J., Narhi, L., Boone, T. and Kenney, W. (1993) Cysteine 17 of recombinant human granulocyte colony-stimulating factor is partially solvent-exposed. J. Protein Chem. 12, 525-531.

Bazan, F. (1990) Haemopoietic receptors and helical cytokines. Immunology Today 11, 350-354.

Blumberg, H., Conklin, D., Xu, W., Grossmann A. et al. (2001) Cell 104: 9-19.

Boerma M., Wang J. Burnett A. F. et al. (2007) Local administration of interleukin-11 ameliorates intestinal radiation injury in rats. 67: 9501-9506.

Bowen, S., Tare, N., Inoue, T., Yamasaki, M., Okabe, M., Horii, I. And Eliason, J. (1999) Relationship between molecular mass and duration of activity of polyethylene glycol conjugated granulocyte colony-stimulating factor mutein. Exp. Hematol. 27, 425-432.

Cantrell, M. A., Anderson, D., Cerretti, D. P., Price, V., McKereghan, K., Tushinski, R. J., Mochizuki, D. Y., Larsen, A., Grabstein, K., Gillis, S. and Cosman, D. Proc. Natl. Acad. Sci. USA 82: 6250-6254 (1985).

Carlo-Stella C, Di Nicola M, Milani R et al (2004) Use of recombinant human growth hormone (rhGH) plus recombinant human granulocyte colony-stimulating factor (rhG-CSF) for the mobilization and collection of CD34+ cells in poor mobilizers. Blood 103: 3287-3295.

Cox, G. N., Smith, D. J., Carlson, S. J., Bendele, A. M., Chlipala, E. A. and Doherty, D. H. (2004) Enhanced circulating half-life and hematopoietic properties of a human granulocyte colony-stimulating factor (G-CSF)-immunoglobulin fusion protein. Exp. Hematol. 32, 441-449. de Vos, A. M., Ultsch, M. and Kossiakoff, A. A. (1992) Science 255: 306-312.

Ersoy B, Ozbililgin K, Kasirga E et al. (2009) Effect of Growth Hormone o small intestinal homeostasis relation to cellular mediators IGF-I and IGFBP-3. World J Gastroenterol 15: 5418-5424.

Glaspy G A (2003) Hematopoietic management in oncology practice. Part 1. Myeloid growth factors. Oncology (Williston Park) 17: 1593-1603.

Goeddel, D. V., Heyneker, H. L., Hozumi, T. et al., (1979) Nature 281: 544-548.

Goldman S J. (1995) Preclinical biology of interleukin-11: a multifunctional hematopoietic cytokine with potent thrombopoietic activity. Stem Cells 13: 462-71. of recombinant interleukin-2 at its glycosylation site. Biotechnology 8, 343-346.

Goodson, R. J. and Katre, N. V. (1990) Biotechnology 8: 343-346.

Howarth G S (2003) Insulin-like growth factor-I and the gastrointestinal system: therapeutic indications and safety implications. J. Nutr. 133: 2109-2112.

Howarth G S, Fraser R, Frisby C L et al. (1997) Effects of insulin-like growth factor-I administration on radiation enteritis in rats. Scand J Gastroenterol 32: 1118-1124.

Kawashima, I., Ohsumi, J., Mita-Honjo, K., Shimoda-Takano, Ishikawa, H., Sakakibara, S., Miyadai, K. and Takiguchi, Y. (1991) FEBS Letts. 283: 199-202.

Lee, F., Yokota, T., Otsuka, T., Gemmell, L., Larson, N., Luh, J., Arai, K.-I. and Rennick, D. (1985) Proc. Natl. Acad. Sci. USA 82: 4360-4364.

Lu, H. S., Boone, T. C., Souza, L. M. and Lai, P. H. (1989) Disulfide and secondary structures of recombinant human granulocyte colony-stimulating factor. Arch. Biochem. Biophys. 268, 81-92.

Martial, J. A., Hallewell, R. A., Baxter, J. D. and Goodman, H. M. (1979) Science 205: 602-606.

Mott, H. R. and Campbell, I. D. (1995) Current Opinion in Structural Biology 5: 114-121.

Mylonas P G, Matsouka P T, Papandoniou E V et al (2000) Growth Hormone and insulin-like growth factor I protect intestinal cells from radiation induced apoptosis. Mol Cell Endocrinol 160: 115-122.

Nagata, S., Tsuchiya, M., Asano, S., Kziro, Y., Yamazaki, T., Yamamoto, O., Hirata, Y., Kubota, N., Oh-eda, M., Nomura, H. and Ono, M. (1986a) Nature 319: 415-418.

Nagata, S., Tsuchiya, M., Asano, S., Yamamoto, O., Hirata, Y., Kubota, N., Oh-eda, M., Nomura, H. and Yamazaki, T. (1986b) EMBO J. 5: 575-581.

Paul, S. R., Bennett, F., Calvetti, J. A., Kelleher, K., Wood, C. R., O'Hara, R. M., Leary, A. C., Sibley, B., Clark, S. C., William, D. A. and Yang, Y.-C. (1990) Proc. Natl. Acad. Sci. USA 87: 7512-7516.

Raguso C A, Leverve X and Pichard C (2002) Protective effects of recombinant growth hormone on intestinal mucosa in rats receiving abdominal radiotherapy. Clin Nutr 21: 487-490.

Silvennoinen, O. and Ihle, J. N. (1996) Signalling by the Hematopoietic Cytokine Receptors, R. G. Landes, Company, Austin, Tex.

Sirohi B, Powles R, Morgan G et al. (2007) Use of physiological doses of human growth hormone in haematological patients receiving intensive chemotherapy promotes haematopoietic recovery: a double blind randomized, placebo-controlled study. Bone Marrow Transplant. 39: 115-120.

Sitaraman S V and Gewirtz A T (2001) Oprelvekin. Genetics Institute. Curr. Opin. Investig. Drugs 2: 1395-400.

Souza, L. M., Boone, T. C., Gabrilove, J., Lai, P. H., Zsebo, K. M., Murdock, D. C., Chazin, V. R., Bruszewski, J., Lu, H., Chen, K. K., Barendt, J., Platzer, E., Moore, M. A. S., Mertelsmann, R. and Welte, K. (1986) Science 232: 61-65.

Van der Meeren A., Mouthon M. A., Gaugler M. H., Vandamme M. Gourmelon P. (2002) Administration of recombinant human interleukin-11 after supralethal radiation exposure promotes survival in mice: interactive effect with thrombopoietin. Radiat. Res. 157: 642-649.

Wen, D., Boissel, J. P., Showers, M., Ruch, B. C. and Bunn, H. F. (1994) J. Biol. Chem. 269: 22839-22846.

Yang Y-C. Interleukin-11 (IL-11) and its receptor: Biology and potential clinical applications in thrombocytopenic states. In: Kurzrock R, Talpaz M, editors. Cytokines: interleukins and their receptors, Norwell, Mass.: Academic Publishers; 1995, Chapter 13, p. 321-340.

Zhang Y., Chen J, Liang, D., Yuan Y and Wu X (2008) Effects of human growth hormone on hematopoietic recovery of rats receiving chemotherapy. Chemotherapy 54: 447-455.

---

What is claimed is:

1. A method for improving survival from radiation exposure in a subject who has been exposed to radiation and has been diagnosed as having Acute Radiation Syndrome (ARS) by administering to the subject an effective dose of a long-acting human granulocyte-macrophage colony-stimulating factor (GM-CSF) protein analog comprising a cysteine residue substituted for alanine-3 of SEQ ID NO: 2, and wherein the long-acting human GM-CSF protein analog is modified with a single polyethylene glycol (PEG).

2. The method of claim 1, wherein the improved survival correlates with accelerated recovery of the subject's blood cell types selected from the group consisting of neutrophil levels, white blood cell levels, platelet levels, red blood cell levels, lymphocyte levels, and combinations thereof.

3. The method of claim 2, wherein the improved survival correlates with accelerated recovery of the subject's neutrophil levels.

4. The method of claim 2, wherein the improved survival correlates with accelerated recovery of the subject's platelet levels.

5. The method of claim 2, wherein the improved survival correlates with accelerated recovery of the subject's red blood cell levels.

6. The method of claim 2, wherein the improved survival correlates with accelerated recovery of the subject's neutrophil levels and platelet levels.

7. The method of claim 2, wherein the improved survival correlates with accelerated recovery of the subject's platelet levels, red blood levels and neutrophil levels.

8. The method of claim 1, wherein the long-acting GM-CSF protein analog is fused to a second protein selected from the group consisting of immunoglobulin domains, albumin, transferrin, transferrin receptors, elastin and elastin-like proteins.

9. The method of claim 1, wherein the long-acting GM-CSF protein analog is a recombinant human GM-CSF protein analog.

10. The method of claim 9, wherein the recombinant human GM-CSF protein analog is modified with a 40 kDa polyethylene glycol (PEG).

11. The method of claim 1, wherein the effective dose is a single dose of the long-acting GM-CSF protein analog of at least about 0.1 µg to about 5 mg per kg of the subject to which the dose is administered to.

12. The method of claim 1, wherein the subject is administered one or more doses of the long-acting GM-CSF protein analog.

13. The method of claim 12, wherein the subject is administered a single effective dose of the long-acting GM-CSF protein analog one to nine times following the subject's exposure to radiation.

14. The method of claim 12, wherein the subject is administered one single effective dose of the long acting GM-CSF protein analog.

15. The method of claim 12, wherein the subject is administered one or more doses of the long-acting GM-CSF protein analog at least about 24 hours following the subject's exposure to the radiation.

16. The method of claim 12, wherein the subject is administered one or more doses of the long-acting GM-CSF protein analog using an every other day dosing regimen.

17. The method of claim 12, wherein the subject is administered one or more doses of the long-acting GM-CSF factor beginning at least 24 hours following the subject's exposure to the radiation followed by an every other day dosing regimen.

18. The method of claim 12, wherein the subject is administered one or more doses of the long-acting GM-CSF protein analog beginning within about 24 hours following the subject's exposure to the radiation.

19. The method of claim 12, wherein the subject is administered a single effective dose of the long-acting GM-CSF protein analog one to three times following the subject's exposure to radiation.

20. The method of claim 1, further comprising administering to the subject an effective dose of one or more long-acting protein analogs selected from the group consisting of a long-acting G-CSF analog, a long-acting interleukin-11 (IL-11) analog and combinations thereof.

* * * * *

SEQUENCE LISTING

<160> NUMBER OF SEQ ID NOS: 6

<210> SEQ ID NO 1
<211> LENGTH: 174
<212> TYPE: PRT
<213> ORGANISM: Homo sapiens

<400> SEQUENCE: 1

```
Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160
```

```
Leu Glu Val Ser Tyr Arg Val Leu Arg His Leu Ala Gln Pro
                165                 170

<210> SEQ ID NO 2
<211> LENGTH: 127
<212> TYPE: PRT
<213> ORGANISM: Homo sapiens

<400> SEQUENCE: 2

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 3
<211> LENGTH: 199
<212> TYPE: PRT
<213> ORGANISM: Homo sapiens

<400> SEQUENCE: 3

Met Asn Cys Val Cys Arg Leu Val Leu Val Val Leu Ser Leu Trp Pro
1               5                   10                  15

Asp Thr Ala Val Ala Pro Gly Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
            180                 185                 190
```

```
Leu Leu Leu Lys Thr Arg Leu
        195

<210> SEQ ID NO 4
<211> LENGTH: 191
<212> TYPE: PRT
<213> ORGANISM: Homo sapiens

<400> SEQUENCE: 4

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 5
<211> LENGTH: 166
<212> TYPE: PRT
<213> ORGANISM: homo sapiens

<400> SEQUENCE: 5

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125
```

```
Pro Leu Arg Thr Ile Thr Ala Asp Thr Phe Arg Lys Leu Phe Arg Val
    130             135                 140

Tyr Ser Asn Phe Leu Arg Gly Lys Leu Lys Leu Tyr Thr Gly Glu Ala
145             150                 155                 160

Cys Arg Thr Gly Asp Arg
                165

<210> SEQ ID NO 6
<211> LENGTH: 124
<212> TYPE: PRT
<213> ORGANISM: Mus musculus

<400> SEQUENCE: 6

Ala Pro Thr Arg Ser Pro Ile Ile Val Thr Arg Pro Trp Lys His Val
1               5                   10                  15

Glu Ala Ile Lys Glu Ala Leu Asn Leu Leu Asp Asp Met Pro Val Thr
                20                  25                  30

Leu Asn Glu Glu Val Glu Val Val Ser Asn Glu Phe Ser Phe Lys Lys
            35                  40                  45

Leu Thr Cys Val Gln Thr Arg Leu Lys Ile Phe Glu Gln Gly Leu Arg
    50                  55                  60

Gly Asn Phe Thr Lys Leu Lys Gly Ala Leu Asn Met Thr Ala Ser Tyr
65                  70                  75                  80

Tyr Gln Thr Tyr Cys Pro Pro Thr Pro Glu Thr Asp Cys Glu Thr Gln
                85                  90                  95

Val Thr Thr Tyr Ala Asp Phe Ile Asp Ser Leu Lys Thr Phe Leu Thr
                100                 105                 110

Asp Ile Pro Phe Glu Cys Lys Lys Pro Ser Gln Lys
            115                 120
```